US012285464B2

(12) United States Patent
Tabas et al.

(10) Patent No.: US 12,285,464 B2
(45) Date of Patent: Apr. 29, 2025

(54) THERAPEUTIC TARGETS INVOLVED IN THE PROGRESSION OF NONALCOHOLIC STEATOHEPATITIS (NASH)

(71) Applicants: The Trustees of Columbia University in the City of New York, New York, NY (US); The Brigham and Women's Hospital, Inc., Boston, MA (US)

(72) Inventors: Ira Tabas, New City, NY (US); Xiaobo Wang, Fort Lee, NJ (US); Omid Farokhzad, Waban, MA (US); Xiaoding Xu, Malden, MA (US)

(73) Assignees: The Trustees of Columbia University in the City of New York, New York, NY (US); The Brigham and Women's Hospital, Inc., Boston, MA (US)

( * ) Notice: Subject to any disclaimer, the term of this patent is extended or adjusted under 35 U.S.C. 154(b) by 496 days.

(21) Appl. No.: 16/094,111

(22) PCT Filed: Apr. 18, 2017

(86) PCT No.: PCT/US2017/028109
§ 371 (c)(1),
(2) Date: Oct. 16, 2018

(87) PCT Pub. No.: WO2017/184586
PCT Pub. Date: Oct. 26, 2017

(65) Prior Publication Data
US 2019/0255143 A1 Aug. 22, 2019

Related U.S. Application Data

(60) Provisional application No. 62/323,903, filed on Apr. 18, 2016.

(51) Int. Cl.
| | |
|---|---|
| *C12N 15/113* | (2010.01) |
| *A61K 9/1271* | (2025.01) |
| *A61K 9/50* | (2006.01) |
| *A61K 31/4178* | (2006.01) |
| *A61K 31/4439* | (2006.01) |
| *A61K 31/7105* | (2006.01) |
| *A61K 31/713* | (2006.01) |
| *A61K 38/17* | (2006.01) |
| *A61K 47/69* | (2017.01) |
| *A61K 48/00* | (2006.01) |
| *A61P 1/16* | (2006.01) |
| *G01N 33/50* | (2006.01) |
| *G01N 33/68* | (2006.01) |
| *A61K 45/06* | (2006.01) |

(52) U.S. Cl.
CPC ............ *A61K 38/17* (2013.01); *A61K 9/1271* (2013.01); *A61K 9/5073* (2013.01); *A61K 31/4178* (2013.01); *A61K 31/4439* (2013.01); *A61K 31/7105* (2013.01); *A61K 31/713* (2013.01); *A61K 47/6929* (2017.08); *A61P 1/16* (2018.01); *C12N 15/113* (2013.01); *G01N 33/50* (2013.01); *G01N 33/6893* (2013.01); *A61K 45/06* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | |
|---|---|---|
| 2005/0019801 A1 | 1/2005 | Rubin et al. |
| 2006/0056948 A1 | 3/2006 | Hossain et al. |
| 2008/0050393 A1 | 2/2008 | Tang et al. |
| 2008/0081074 A1 | 4/2008 | Gu et al. |
| 2008/0193536 A1 | 8/2008 | Khademhosseini |
| 2009/0074828 A1 | 3/2009 | Alexis et al. |
| 2009/0298710 A1 | 12/2009 | Farokhzad |
| 2010/0022680 A1 | 1/2010 | Karnik et al. |
| 2010/0092425 A1 | 4/2010 | Von Andrian et al. |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang et al. |
| 2010/0233251 A1 | 9/2010 | Von Andrian et al. |
| 2010/0303723 A1 | 12/2010 | Farokhzad et al. |
| 2010/0323199 A1 | 12/2010 | Gu et al. |
| 2011/0027172 A1 | 2/2011 | Wang et al. |
| 2011/0052697 A1 | 3/2011 | Farokhzad et al. |
| 2011/0065807 A1 | 3/2011 | Radovic-Moreno et al. |
| 2011/0092592 A1 | 4/2011 | Yano |

(Continued)

FOREIGN PATENT DOCUMENTS

| | | |
|---|---|---|
| WO | 2014197738 | 12/2014 |
| WO | 2015190760 | 12/2015 |
| WO | 2015198077 | 12/2015 |

OTHER PUBLICATIONS

Uno et al., Hepatology, 2008, 48: 109-118.*
Wang et al., J. Control. Rel., 2013, 166: 106-114.*
Black, Biochimie, 2007, 89: 1464-1473.*
Breitkopf et al., Alcohol. Clin. Rxp. Res., 2005, 29: 121S-131S.*
Miranda et al., FASEB J., Apr. 1, 2015, 29, 558.12; Abstract.*
Hong et al., Science, 2005, 309: 1074-1078.*
Cheng et al., Mol. Pharm., 2009, 6: 772-779.*

(Continued)

*Primary Examiner* — Ileana Popa
(74) *Attorney, Agent, or Firm* — Bryan Cave Leighton Paisner LLP

(57) ABSTRACT

The present invention relates to methods and compositions for specifically modulating the Hippo pathway transcription factor TAZ (WWTR1), as a therapeutic target for inhibiting or preventing liver conditions including the progression of steatosis-to-NASH in a patient.

7 Claims, 38 Drawing Sheets

Specification includes a Sequence Listing.

(56) References Cited

U.S. PATENT DOCUMENTS

| | | |
|---|---|---|
| 2011/0143993 A1 | 6/2011 | Langer et al. |
| 2011/0196187 A1 | 8/2011 | Ludwig et al. |
| 2011/0268804 A1 | 11/2011 | Shi et al. |
| 2011/0268805 A1 | 11/2011 | Alexis et al. |
| 2011/0300219 A1 | 12/2011 | Lippard |
| 2012/0087890 A1 | 4/2012 | Iannacone |
| 2012/0156135 A1 | 6/2012 | Farokhzad |
| 2012/0266491 A1 | 10/2012 | May |
| 2013/0017265 A1 | 1/2013 | Farokhzad et al. |
| 2013/0129790 A1 | 5/2013 | Alexis |
| 2013/0130348 A1 | 5/2013 | Gu et al. |
| 2013/0236533 A1 | 9/2013 | Von Andrian et al. |
| 2013/0287857 A1 | 10/2013 | Von Andrian et al. |
| 2013/0315831 A1 | 11/2013 | Shi |
| 2014/0017327 A1 | 1/2014 | Cheng et al. |
| 2014/0037736 A1 | 2/2014 | Shi et al. |
| 2014/0079776 A1 | 3/2014 | Lippard et al. |
| 2014/0127301 A1 | 5/2014 | Alexis et al. |
| 2014/0314864 A1 | 10/2014 | Cheng et al. |
| 2014/0314865 A1 | 10/2014 | Von Andrian et al. |
| 2015/0023875 A1 | 1/2015 | Farokhzad et al. |
| 2015/0125391 A1 | 5/2015 | Swami et al. |
| 2015/0157584 A1 | 6/2015 | Guan et al. |
| 2015/0157737 A1 | 6/2015 | Gu et al. |
| 2015/0174549 A1 | 6/2015 | Lim |
| 2015/0182461 A1 | 7/2015 | Kim et al. |
| 2015/0265716 A1 | 9/2015 | Valencia et al. |
| 2015/0342943 A1 | 12/2015 | Bornstein et al. |
| 2015/0377910 A1 | 12/2015 | McCreedy et al. |
| 2016/0008451 A1 | 1/2016 | Stary et al. |
| 2016/0017335 A1 | 1/2016 | Borodovsky et al. |
| 2016/0022835 A1 | 1/2016 | Farokhzad et al. |
| 2016/0187323 A1 | 6/2016 | Farokhzad et al. |
| 2016/0228574 A1 | 8/2016 | Farokhzad et al. |
| 2016/0338970 A1 | 11/2016 | Farokhzad et al. |
| 2016/0339113 A1 | 11/2016 | Von Andrian et al. |

OTHER PUBLICATIONS

Wang et al., Radiation Research. 2013, 179: 69-75.*
Sequence alignment, 2021.*
Inazaki, Kidney Int., 2004, 66: 597-604.*
Wang, Lipids in Health and Disease, 2013, 12: 1-8.*
Carmona-Cuenca, J. Hepatol., 2006, 49: 965-976.*
International Search Report and Written Opinion dated Aug. 7, 2017 corresponding to International Patent Application No. PCT/US2017/028109; 2 pages.
Bertero et al. "A YAP/TAZ-miR-130/301 molecular circuit exerts systems-level control of fibrosis in a network of human diseases and physiologic conditions," Scientific Reports, Dec. 15, 2015 (Dec. 15, 2015), vol. 5, pp. 1-15.
Sanyal et al., Pioglitazone, vitamin E, or placebo for nonalcoholic steatohepatitis. N Engl J Med. May 6, 2010;362(18):1675-85.
Paul Angulo. Nonalcoholic Fatty Liver Disease. N Engl J Med 2002; 346:1221-1231.
Angulo et al., Fibrosis in nonalcoholic Fatty liver disease: mechanisms and clinical implications, Semin Liver Dis. 2015;35(2):132-45.
Fitzgerald et al. "A Highly Durable RNAi Therapeutic Inhibitor of PCSK9", N. Engl. J. Med. 2017; 376:41-51.
Anastasia Khvorova, Oligonucleotide Therapeutics—A New Class of Cholesterol-Lowering Drugs, N Engl J Med. 2017; 376(1):4-7.
Zuckerman et al.,"Clinical experiences with systemically administered siRNA-based therapeutics in cancer", Nat. Rev. Drug Discov. 2015;14(12):843-56.
Lutz et al., Cooperative function of YAP and TAZ in hepatocytes and hepatocarcinogenesis, Zeitschrift Fur Gastroenterologie, 2015, vol. 53, No. 1, pp. A4-A10.
Machado et al, Accumulation of duct cells with activated YAP parallels fibrosis progression in non-alcoholic fatty liver disease, Journal of Hepatology, 2015, vol. 63, No. 4, pp. 962-970.
Johnson et al, The two faces of Hippo: Targeting the Hippo pathway for regenerative medicine and cancer treatment, Nature Reviews. Drug Discovery, 2014, vol. 13, No. 1, pp. 63-79.
Wang et al, Hepatocyte TAZ/WWTRI Promotes Inflammation and Fibrosis in Nonalcoholic Steatohepatitis, Cell Metabolism, 2016, vol. 24, No. 6, pp. 848-862.
Supplementary European Search Report dated Oct. 23, 2019 in European Patent Application EP 17786458.
Day et al: "Steatohepatitis: A tale of two "hits" ? ", Gastroenterology, vol. 114, No. 4, 1998, pp. 842-845.
Hideki Fujii et al: "Inflammation and fibrogenesis in steatohepatitis", Journal of Gastroenterology, vol. 47, No. 3, 2012, pp. 215-225.

* cited by examiner

Mouse Ihh intron 1

| | | | | |
|---|---|---|---|---|
| Mouse | SEQ ID NO: 73 | GGCCGGGCCGGGCTGGGCGCCG | AGGAATGC | AG |
| Human | SEQ ID NO: 74 | GGCCGGGCCGGGCCGGGCGCCG | AGGAATGC | AG |
| Chimp | SEQ ID NO: 75 | GGCCGGGCCGGGCCGGGCGCCG | AGGAATGC | AG |
| Dolphin | SEQ ID NO: 76 | GGCCGGGCCGGGCCGGGCGCCG | AGGAATGC | AG |
| Pig | SEQ ID NO: 77 | GGCCGGGCCGGGCCGGGCGCCG | AGGAATGC | AG |
| Rabbit | SEQ ID NO: 78 | GGCCGGGCCGGGCCGGGCGCCG | AGGAATGC | AG |
| Rat | SEQ ID NO: 79 | GGCCGGGCCGGGCTGGGCGCCG | AGGAATGC | AG |
| | SEQ ID NO: 80 | | TCCTTACG | |

TAZ/TEAD

FIG.7A

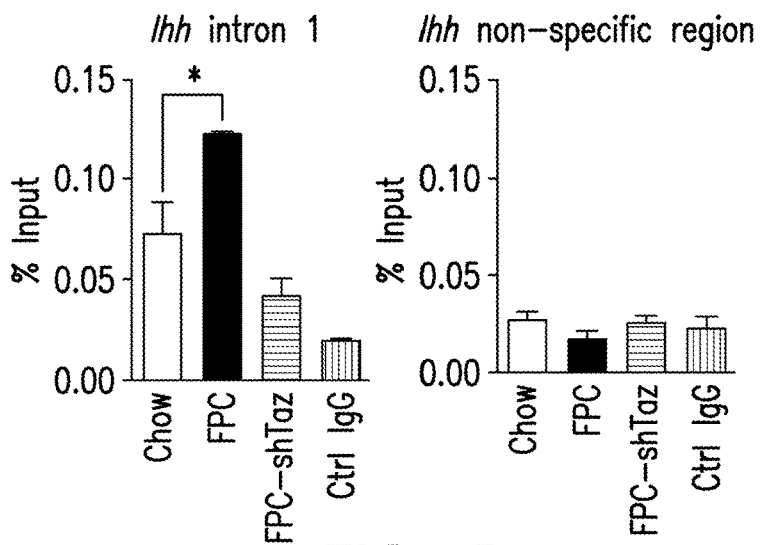

FIG.7B

FIG.7C

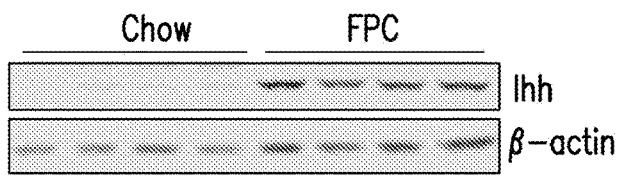

FIG.7D

```
                       SEQUENCE LISTING

<160> NUMBER OF SEQ ID NOS: 84

<210> SEQ ID NO 1
    <211> LENGTH: 53
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 1
caccacagcc gaatctcgca atgaatctcg agattcattg cgagattcgg ctg         53

<210> SEQ ID NO 2
    <211> LENGTH: 25
    <212> TYPE: RNA
    <213> ORGANISM: Artificial Sequence
    <220> FEATURE:
    <223> OTHER INFORMATION: Description of Artificial Sequence: Synthetic
          oligonucleotide

<400> SEQUENCE: 2
acauggacga gauggauaca gguga                                        25

<210> SEQ ID NO 3
    <211> LENGTH: 21
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 3
tcagtcaacg ggggacataa a                                            21

<210> SEQ ID NO 4
    <211> LENGTH: 21
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 4
ggggctgtac tgcttaacca g                                            21

<210> SEQ ID NO 5
    <211> LENGTH: 21
    <212> TYPE: DNA
    <213> ORGANISM: Artificial Sequence
```

```
<220> FEATURE:
<223> OTHER INFORMATION: Description of Artificial Sequence: Synthetic
      primer

<400> SEQUENCE: 5
catggcggaa aaagatcctc c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcggtcacg tcataggact g                                              21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctcccgtggc ttctagtgc                                                 19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccttagttt ggacaggatc tg                                             22

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgctcccag ggctgttttc ccat                                           24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtggtgccag atcttttcca tgtcg                                          25

<210> SEQ ID NO 11
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 11
tttctctgcc tctgccaac                                                19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctcattgat cacctgtcca tc                                            22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctaaaggatg agatggcccg                                               20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaaggtctgg ataggaaggt tg                                            22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctcctctta ggggccact                                                19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccacgtctca ccattgggg                                                19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 17
gtaacttcgt gcctagcaac a                                              21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cctttgtcag aatactgagc agc                                            23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgtaacatg gaaactgggg aaa                                            23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccatagctga actgaaaacc acc                                            23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
accacaatac ctacatgcac c                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagcaggcga ggaaaagata g                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 23
cttctgtcta ctgaacttcg gg                                             22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggcttgtc actcgaattt tg                                             22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttaaaaacct ggatcggaac caa                                            23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcattagctt cagatttacg ggt                                            23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctcttgccta caagcagttc a                                              21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgtgttctc ctcgtcctt                                                 19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 29
caacgcctac tctcccagac                                              20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagccttgat gtactgtacc ac                                           22

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cacagctcta cggcgactg                                               19

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgcatagtg attgcgtttc ttc                                          23

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgacccatc tcagaagcag aatct                                        25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tccatgtggt catggctttc attgg                                        25

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
```
ctcaaagacc tatagtgctg gc 22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caaagtgacg gctctggtag 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcacaccagg cagtagcttt 20

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caggagttga ttccagacag gta 23

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcgctgatgc actgcctatg 20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagaggtcca cagagctgat t 21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctgacctgaa agccgagaag                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agaaggtgct aacgaacagg                                                20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aagtcccaga aatcgcctat g                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtatggttt cacgactgga g                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atgggcggaa tggtctcttt c                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tggggacctt gtcttcatca t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atgcggtgga acactttctg g                                              21

```
<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcacgtcaac tctacactgg t                                            21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aacctgctcc aaaagtgaac c                                            21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cccagggtaa tatggaagag gc                                           22

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caatcattga cagcgagggc                                              20

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtgtagctc ggttctggta g                                            21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggtgtagctc ggttctggta g                                            21
```

```
<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcacctggga ctccatttgc                                               20

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcattgcgag attcggctg                                                19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gatgaatccg tcctcggtg                                                19

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gaggcaagtt gaaaggtcag aggca                                         25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gctgcaccac gttctgcctt tgtac                                         25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggcaatgacg tccttagctg tttag                                         25
```

-continued

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aggcagcttg gtccaggaag tgatt                                              25

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acctcttcaa ctctgtcatg aa                                                 22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgccctttct aacctggctg ta                                                 22

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgccaccgtt catcattttc ctgct                                              25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tccccgagtc cccagaaaga tgaat                                              25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccagctcatg gcggaaaaag atcct                                              25

<210> SEQ ID NO 66

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
accccaggaa ggtgatgaat cagcc                                          25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gggccttgcg gaccaagtga tgagg                                          25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcccttgact gtttactaat agata                                          25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccaaatccat cagatgaaac cattt                                          25

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gcctgcattt ctgtggcaga ta                                             22

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gccatgagca cagatatgag atct                                           24

<210> SEQ ID NO 72
<211> LENGTH: 21
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tcccagccaa atctcgtgat g                                              21

<210> SEQ ID NO 73
<211> LENGTH: 32
<212> TYPE: DNA
<213> ORGANISM: Mus sp.

<400> SEQUENCE: 73
ggccgggccg ggctgggcgc cgaggaatgc ag                                  32

<210> SEQ ID NO 74
<211> LENGTH: 32
<212> TYPE: DNA
<213> ORGANISM: Homo sapiens

<400> SEQUENCE: 74
ggccgggccg ggccgggcgc cgaggaatgc ag                                  32

<210> SEQ ID NO 75
<211> LENGTH: 32
<212> TYPE: DNA
<213> ORGANISM: Pan troglodytes

<400> SEQUENCE: 75
ggccgggccg ggccgggcgc cgaggaatgc ag                                  32

<210> SEQ ID NO 76
<211> LENGTH: 32
<212> TYPE: DNA
<213> ORGANISM: Tursiops sp.

<400> SEQUENCE: 76
ggccgggccg ggccgggcgc cgaggaatgc ag                                  32

<210> SEQ ID NO 77
<211> LENGTH: 32
<212> TYPE: DNA
<213> ORGANISM: Sus sp.

<400> SEQUENCE: 77
ggccgggccg ggccgggcgc cgaggaatgc ag                                  32

<210> SEQ ID NO 78
<211> LENGTH: 32
<212> TYPE: DNA
<213> ORGANISM: Oryctolagus cuniculus

<400> SEQUENCE: 78
ggccgggccg ggccgggcgc cgaggaatgc ag                                  32

<210> SEQ ID NO 79
<211> LENGTH: 32
<212> TYPE: DNA
<213> ORGANISM: Rattus sp.

<400> SEQUENCE: 79
ggccgggccg ggctgggcgc cgaggaatgc ag                                  32

<210> SEQ ID NO 80
<211> LENGTH: 8
<212> TYPE: DNA
<213> ORGANISM: Artificial Sequence
<220> FEATURE:
<223> OTHER INFORMATION: Description of Artificial Sequence: Synthetic
      consensus oligonucleotide

<400> SEQUENCE: 80 gcattcct                                                                    8

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agcgcattgg gcatactcat                                                      20

<210> SEQ ID NO 82
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ugcggacaau cauacagaac cagca                                                25

<210> SEQ ID NO 83
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
accaccuuca gugaugugcu ua                                                   22

<210> SEQ ID NO 84
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ggauacuagu ugugaaaugg aaaga                                                25

THERAPEUTIC TARGETS INVOLVED IN THE PROGRESSION OF NONALCOHOLIC STEATOHEPATITIS (NASH)

CROSS-REFERENCE TO RELATED APPLICATIONS

This present application is a 371 national stage application of International Application No. PCT/US2017/028109 filed on Apr. 18, 2017, which claims priority to U.S. Provisional Patent Application Ser. No. 62/323,903 filed Apr. 18, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 16, 2018, is named 01001_004648-US1_ST25.txt and is 18,847 bytes in size.

FIELD OF THE INVENTION

The present invention relates to methods and compositions for specifically modulating the Hippo pathway transcription factor TAZ (WWTR1), as a therapeutic target for inhibiting or preventing liver conditions including the progression of steatosis-to-NASH.

GOVERNMENT SUPPORT

This invention was made with government support under NHL087123, HL127464, EB015419; and CA151884 awarded by the National Institutes of Health. The government has certain rights in the invention.

BACKGROUND

Nonalcoholic steatohepatitis (NASH) has emerged as the leading cause of chronic liver disease worldwide. However, there is a dearth of treatment options, which is due in large part to a poor understanding of how benign steatosis progresses to NASH. NASH is a common and serious complication of obesity and type 2 diabetes, but many gaps remain in our understanding of its pathophysiology, leading to a lack of treatment options (White et al., 2012). NASH most likely develops as a result of multiple hits (Day and James, 1998), including steatosis, driven by hyperinsulinemia and elevated free fatty acid delivery to the liver, in combination with insults that promote inflammation, fibrosis, and hepatocyte death (Singh et al., 2015). However, the molecular mechanisms corresponding to these pathogenic processes and their integration are poorly understood. The incomplete understanding of NASH can be explained in part by the paucity of animal models that combine steatosis, obesity/insulin resistance, and key features of NASH, such as inflammation and fibrosis, as well as by insufficient integration of experimental results with human NASH findings.

There is a great need for improved models that mimic the relevant human disease conditions, as well as for new therapeutic targets for treating or preventing NASH and related conditions.

SUMMARY OF THE INVENTION

In certain embodiments, the present invention relates to methods for treating or preventing a liver condition in patient, selected from the group consisting of fatty liver disease, non-alcoholic fatty liver disease, adiposity, and combinations thereof, comprising administering to the patient in need thereof, a therapeutically effective amount of an inhibitor of TAZ.

In certain embodiments, the inhibitor of TAZ is administered to at least one hepatocyte of said patient. In additional embodiments, the liver disease is associated with imbalanced liver lipid metabolism and/or increased fat deposits.

In certain embodiments, the non-alcoholic fatty liver disease is non-alcoholic Steatosis hepatis or non-alcoholic Steatohepatitis (NASH). In certain embodiments, the fatty liver disease is Steatosis hepatis or Steatohepatitis. In certain embodiments, one or more symptoms selected from the group consisting of hepatic inflammation, hepatocyte death, insulin resistance, weight gain, and fibrosis is decreased in the patient.

In certain embodiments, the methods further comprise administering a therapeutically effective amount of an inhibitor of Indian hedgehog (Ihh), an inhibitor of YAP, an inhibitor of TEAD1, and inhibitor of TEAD2, an inhibitor of TEAD3, an inhibitor of TEAD4, or any combination thereof.

In certain embodiments, the inhibitor of TAZ is selected from the group consisting of proteins, nucleic acids, and combinations thereof. In certain embodiments, the nucleic acid is selected from the group consisting of antisense oligonucleotide, siRNA, shRNA, and combinations thereof. In additional embodiments, the nucleic acid is SEQ ID NO:1 or SEQ ID NO:2, or any nucleic acid selected from the group consisting of SEQ ID NO:55-SEQ ID NO:72, and SEQ ID NO:81.

In certain embodiments the inhibitor of TAZ, alone or in combination with an inhibitor of Indian hedgehog (Ihh) an inhibitor of YAP, an inhibitor of TEAD1, and inhibitor of TEAD2, an inhibitor of TEAD3, an inhibitor of TEAD4, is a nucleic acid and the nucleic acid is formulated in a nanoparticle. In additional embodiments, the nanoparticle comprises: 1) a hydrophobic inner core, 2) a hydrophilic outer shell and 3) a hepatocyte targeting ligand. In certain embodiments, the hydrophilic outer shell increases blood circulation half-life. In additional embodiments, the hydrophilic outer shell provides immune system evasion. In additional embodiments, the nanoparticle comprises, or is administered in combination with at least one additional therapeutic agent for treatment of steatosis hepatis, steatohepatitis, non-alcoholic fatty liver disease, non-alcoholic steatohepatitis, adiposity and combinations thereof, and/or optionally the nanoparticle comprises, or is administered in further combination with a therapeutic agent selected from antidiabetic drugs and insulin sensitizers selected from the group consisting of: Rosiglitazone; Pioglitazone; Losartan; Simtuzumab (anti-LOXL2); GR-MD-02; Obeticholic acid (OCA) and combinations thereof.

In additional embodiments, the methods further comprise administering at least one additional therapeutic agent for treatment of steatosis hepatis, steatohepatitis, non-alcoholic fatty liver disease, non-alcoholic steatohepatitis, adiposity and combinations thereof. In additional embodiments, the additional therapeutic agent is selected from antidiabetic drugs and insulin sensitizers selected from the group consisting of: Rosiglitazone; Pioglitazone; Losartan; Simtuzumab (anti-LOXL2); GR-MD-02; Obeticholic acid (OCA) and combinations thereof.

In certain embodiments, the present invention relates to pharmaceutical composition comprising: at least an inhibitor of TAZ, alone or in combination with an inhibitor of Indian hedgehog (Ihh) an inhibitor of YAP, an inhibitor of TEAD1, and inhibitor of TEAD2, an inhibitor of TEAD3, an inhibitor of TEAD4, or any combination thereof, and optionally, at least one additional therapeutic agent for treatment of steatosis hepatis, steatohepatitis, non-alcoholic fatty liver disease, non-alcoholic steatohepatitis, adiposity and combinations thereof.

In certain embodiments, the therapeutic agent is selected from antidiabetic drugs and insulin sensitizers selected from the group consisting of: Rosiglitazone; Pioglitazone; Losartan; Simtuzumab (anti-LOXL2); GR-MD-02; Obeticholic acid (OCA) and combinations thereof.

In additional embodiments, the present invention relates to a method for inhibiting TAZ expression in a hepatocyte comprises contacting the hepatocyte with an inhibitor of TAZ.

In certain embodiments, the present invention relates to methods of inhibiting liver fibrosis in a patient comprising contacting a hepatocyte with an inhibitor of TAZ.

In certain embodiments, Indian hedgehog (Ihh) expression is also inhibited.

In certain embodiments, the liver fibrosis is associated with imbalanced liver lipid metabolism and/or increased fat deposits. In certain embodiments, the liver fibrosis is associated with non-alcoholic Steatosis hepatis or non-alcoholic Steatohepatitis (NASH). In certain embodiments, the liver fibrosis is associated with Steatosis hepatis or Steatohepatitis.

In certain embodiments, one or more symptoms are selected from the group consisting of hepatic inflammation, hepatocyte death, insulin resistance, weight gain, and fibrosis is decreased in the patient.

In additional embodiments, the methods further comprise administering a therapeutically effective amount of an inhibitor of Indian hedgehog (Ihh) an inhibitor of YAP, an inhibitor of TEAD1, and inhibitor of TEAD2, an inhibitor of TEAD3, an inhibitor of TEAD4, or any combination thereof.

In certain embodiments, the inhibitor of TAZ is selected from the group consisting of proteins, nucleic acids, and combinations thereof. In certain embodiments, the nucleic acid is selected from the group consisting of antisense oligonucleotide, siRNA, shRNA, and combinations thereof. In certain embodiments, the nucleic acid is SEQ ID NO:1 or SEQ ID NO:2, or any nucleic acid selected from the group consisting of SEQ ID NO:55-SEQ ID NO:72 and SEQ ID NO:81.

In certain embodiments, the method further comprises administering at least one additional therapeutic agent for treatment of steatosis hepatis, steatohepatitis, non-alcoholic fatty liver disease, non-alcoholic steatohepatitis, adiposity and combinations thereof. In certain embodiments, the additional therapeutic agent is selected from antidiabetic drugs and insulin sensitizers selected from the group consisting of: Rosiglitazone; Pioglitazone; Losartan; Simtuzumab (anti-LOXL2); GR-MD-02; Obeticholic acid (OCA) and combinations thereof.

In additional embodiments, the present invention relates to a method for diagnosing NASH or susceptibility to NASH in a human subject comprising detecting an elevated level of TAZ, Indian hedgehog (Ihh), YAP, TEAD1, TEAD2, TEAD3, TEAD4, or any combination thereof, wherein an elevated level above baseline, of any one or more of TAZ, Indian hedgehog (Ihh), YAP, TEAD1, TEAD2, TEAD3, TEAD4 indicates susceptibility to NASH or ongoing NASH in the human subject.

In certain embodiments, the present invention relates to a method for diagnosing NASH or susceptibility to NASH in a human subject comprising: (a) performing an in vitro nucleic acid detection assay on a nucleic acid sample from a human subject to detect the presence of an elevated level of Taz in the subject's nucleic acid sample when compared to a control Taz level and (b) diagnosing the subject as being susceptible to or having NASH based on an elevated level of Taz in the subject's nucleic acid sample, wherein the nucleic acid detection assay comprises amplification of a nucleic acid molecule with at least a primer pair, said primer pair comprising a forward primer comprising the nucleotide sequence set forth in SEQ ID NO:5 and a reverse primer comprising the nucleotide sequence set forth in SEQ ID NO:6 that hybridizes to Taz to produce amplified Taz nucleic acid, wherein the control Taz level of between X and Y indicates a normal Taz range; wherein a Taz level above Y indicates a susceptibility to NASH in the human subject; and wherein a Taz level above Z indicates NASH in the human subject.

In additional embodiments, the present invention relates to an in vitro method for detecting increased Taz expression in a sample comprising: performing an in vitro nucleic acid detection assay on a sample wherein the nucleic acid detection assay comprises amplification of a nucleic acid molecule with at least a primer pair, said primer pair comprising a forward primer comprising the nucleotide sequence set forth in SEQ ID NO:5 and a reverse primer comprising the nucleotide sequence set forth in SEQ ID NO:6 that hybridizes to Taz to produce amplified Taz nucleic acid wherein detecting an elevated level of Taz in the sample when compared to a control Taz level indicates susceptibility to NASH or NASH.

In additional embodiments, the present invention relates to a method for monitoring liver treatment in a patient being treated with an inhibitor of Taz, an inhibitor of Indian hedgehog (Ihh) an inhibitor of YAP, an inhibitor of TEAD1, an inhibitor of TEAD2, an inhibitor of TEAD3, an inhibitor of TEAD4, or any combination thereof, comprising: (a) performing a nucleic acid detection assay on a nucleic acid sample from the patient to detect the presence of Taz in the patient's nucleic acid sample when compared to a reference Taz level, wherein the nucleic acid detection assay comprises amplification of Taz, and (b) determining the patient's responsiveness to treatment based on the level of Taz in the patient's nucleic acid sample, wherein the reference Taz level of between X and Y indicates a normal Taz range and responsiveness to treatment; wherein a Taz level above Y indicates continuing susceptibility to NASH and partial responsiveness to treatment in the patient; and wherein a Taz level above Z indicates NASH in the patient and unresponsiveness to treatment.

In certain embodiments, Taz is detected by hybridizing a labeled oligonucleotide probe to the amplified nucleic acid. In certain embodiments, the sample is a liver biopsy. In certain embodiments, the sample comprises hepatocytes. In certain embodiments, amplification of a nucleic acid comprises PCR or real time PCR (RT-PCR). In certain embodiments, the amplification of a nucleic acid comprises reverse transcriptase PCR. In certain embodiments, the forward and/or the reverse primer is detectably labeled. In certain embodiments, the method further comprises electrophoresis of the amplified nucleic acid. In certain embodiments, the method further comprises using a real-time PCR detection system. In certain embodiments, the control level represents the level of Taz in liver of a healthy subject.

BRIEF DESCRIPTION OF THE DRAWINGS

FIG. 1A is an immunohistochemistry staining showing TAZ immunofluorescence (red) in normal, steatotic, and NASH human liver sections; DAPI counterstain for nuclei is shown in bottom panels. NASH-IgG refers to control for primary antibody. Bar, 100 µm. FIG. 1B is a graph showing the quantification of TAZ+ cells in normal, steatotic, and NASH human liver sections ($*p<0.0001$; mean±SEM; n=7 specimens/group). FIG. 1C shows immunoblots of TAZ in early NAFLD, normal, NASH, and steatotic human liver. For sake of comparison, samples #10-12 of NASH from the left blot were re-run with the steatosis samples in the right blot. GAPDH or β-actin were used as loading control. FIG. 1D shows an immunoblot of liver TAZ in mice fed chow or MCD diet, with β-actin as loading control. FIG. 1E shows an immunoblot of liver TAZ in mice fed chow or FPC diet, with β-actin as loading control. FIG. 1F is a graph showing the quantification of Taz mRNA in livers from mice fed chow or FPC diet ($*p<0.0001$; mean±SEM; n=6 mice/group.

FIG. 2A-B are graphs showing body weight and liver:body weight ratio. FIG. 2Q is a graph showing liver cholesterol content.

FIGS. 3 A-G are immunohistochemistry stains and blots showing comparisons of liver parameters in mice fed the FPC vs. FF Diet for 16 Weeks. The following parameters were measured in male C57BL/6J mice after 16 weeks on chow, FPC, or FF diet ($*p<0.05$, $p<0.01$, $*p<0.0001$; mean±SEM; n=5 mice/group)

FIG. 4A shows an immunoblot of TAZ, with β-actin as loading control. FIG. 4B shows staining of liver sections for H&E (upper panels; Bar, 100 µm), Masson's trichrome (Trichr) (middle panels; Bar, 100 µm), and Sirius red (Sir red) (lower panels; Bar, 500 µm). FIG. 4C shows stains of hepatic inflammatory cells. FIG. 4D shows Aniline blue- and Sirius red-positive areas in the immunohistochemistry staining. FIG. 4E shows Plasma ALT. FIG. 4F shows TUNEL+ cells. FIG. 4G is a graph showing mRNA levels of Tnfa, Mcp1, and F4/80 (Adgre1). FIG. 4H is a graph showing mRNA levels of the indicated genes related to fibrosis. FIG. 4I shows immunohistochemistry F4/80 immunofluorescence (red) staining and graphic quantification of the same data; DAPI counterstain for nuclei is shown in bottom panels; Bar, 100 µm. FIG. 4J shows immunohistochemistry α-SMA immunofluorescence (red) and graphic quantification of the same data; DAPI counterstain for nuclei is shown in bottom panels; Bar, 100 µm.

FIG. 5A shows immunohistochemistry staining of liver sections for H&E (upper panels; Bar, 100 µm), Masson's trichrome (Trichr) (middle panels; Bar, 500 µm), and Sirius red (Sir red) (lower panels; Bar, 500 µm). FIG. 5B is a graph showing reduced hepatic inflammatory cells in shTaz treated mice compared with sh control mice. FIG. 5C is a graph showing Aniline blue- and Sirius red-positive staining areas in shTaz treated mice compared with sh control mice. FIG. 5D is a graph showing reduced Hydroxyproline content in shTaz treated mice compared with sh control mice. FIG. 5E is a graph showing reduced plasma ALT in shTaz treated mice compared with sh control mice. FIG. 5F are graphs showing mRNA levels of Tnfa, Mcp1, Tgfb1, Col1a1, and Timp1 in shTaz treated mice compared with sh control mice. FIG. 5G shows immunohistochemistry F4/80 immunofluorescence (red) and quantification in shTaz treated mice compared with sh control mice; DAPI counterstain for nuclei is shown in bottom panels; Bar, 100 µm. FIG. 5H shows immunohistochemistry α-SMA immunofluorescence (red) and quantification in shTaz treated mice compared with sh control mice; DAPI counterstain for nuclei is shown in bottom panels; Bar, 100 µm.

FIG. 6A shows immunohistochemistry staining of liver sections for H&E (upper panels) and Masson's trichrome (Trichr) (lower panels) from C57BL/6J mice fed chow or FPC diet for 8 weeks; Bar, 100 µm. For FIG. 6B-H, the following parameters were measured in male C57BL/6J mice fed the FPC diet for 16 weeks, with AAV8-shTaz or control vector administered at the 8-week time point ($*p<0.05$; $p<0.01$, $*p<0.0001$, mean±SEM; n=5 mice/group): FIG. 6B shows immunohistochemistry staining of liver sections for H&E (upper panels; Bar, 100 µm), Masson's trichrome (Trichr) (middle panels; Bar, 100 µm), and Sirius red (Sir red) (lower panels; Bar, 500 µm). FIG. 6C is a graph showing reduced hepatic inflammatory cells in shTaz treated mice compared with sh control mice. FIG. 6D are graphs showing reduced Aniline blue- and Sirius red-positive areas in cells from shTaz treated mice compared with sh control mice. FIG. 6E is a graph showing reduced plasma ALT in shTaz treated mice compared with sh control mice. FIG. 6F are graphs showing reduced mRNA levels of Tnfa, Mcp1, Tgfb1, and Acta2 (α-SMA) in shTaz treated mice compared with sh control mice. FIG. 6G shows immunohistochemistry F4/80 immunofluorescence (red) and graphic quantification of the same data in shTaz treated mice compared with sh control mice; DAPI counterstain for nuclei is shown in bottom panels; Bar, 100 μm. FIG. 6H shows immunohistochemistry α-SMA immunofluorescence (red) and graphic quantification of the same data in shTaz treated mice compared with sh control mice; DAPI counterstain for nuclei is shown in bottom panels; Bar, 100 μm.

FIGS. 7A-H are immunohistochemistry stains and graphic quantifications illustrating that TAZ Induces Ihh, and TAZ silencing lowers the expression of Pro-Fibrotic Hedgehog Pathway Genes in the Livers of FPC-Fed mice. FIG. 7A is a sequence alignment showing the conserved TAZ/TEAD consensus sequence in intron 1 of the mouse Ihh gene. FIG. 7B are graphs showing quantitation of liver nuclear extracts from mice fed chow diet or FPC diet for 16 weeks with or without TAZ silencing were subjected to TAZ ChIP analysis using anti-TAZ or IgG control. The intronic region containing the TAZ/TEAD binding sequence, or a non-consensus sequence as control, was amplified by qPCR and normalized to the values obtained from input DNA ($*p=0.03$; mean±SEM; n=3). FIG. 7C is an immunoblot showing Ihh levels in normal human livers or those with steatosis or NASH. FIG. 7D is an immunoblot showing levels of Ihh in the livers of mice fed chow or FPC diet for 16 weeks. FIG. 7E is a graph showing relative expression of Ihh, Gli1, Gli2, and Opn mRNAs in the livers of mice fed chow or FPC diet for 16 weeks ($*p<0.04$, $p<0.0001$; mean±SEM; n=6). FIG. 7F** is a graph showing relative expression of Ihh, Gli1, Gli2, and Opn mRNAs in the livers of mice fed the FPC diet for 16 weeks with or without TAZ silencing ($*p<0.05$, $p<0.002$; mean±SEM; n=10). FIG. 7G is am immunoblot of Ihh in the livers of mice fed the FPC diet for 16 weeks with or without TAZ silencing. FIG. 7H** shows OPN immunohistochemistry and quantification in the livers of mice fed the FPC diet for 16 weeks with or without TAZ silencing ($*p<0.0001$; mean±SEM; n=10); Bar, 200 μm.

FIG. 8A is a graph showing expression of Taz and Ihh mRNA in control (Con) and TAZ-silenced AML12 hepatocytes ($*p<0.0003$; mean±SEM; n=3). FIG. 8B is an immunoblot of TAZ and Ihh in control and TAZ-silenced AML12 hepatocytes. FIG. 8C is a graph showing Ihh concentrations, assayed by ELBA, in the media of control and TAZ-silenced AML12 hepatocytes ($*p<0.003$; mean±SEM; n=3). FIG. 8D is a graph showing results from primary hepatic stellate cells (HSCs) that were incubated for 72 h with conditioned medium (CM) obtained from control (Con) or TAZ-silenced AML12 hepatocytes or with medium not exposed to cells (non-CM). The HSCs were then assayed for Opn, Timp1, and Col1a1 mRNA (upper panel; $*p<0.05$; mean±SEM; n=4) and the respective proteins by immunoblot (lower panel). FIG. 8E is a graph showing HSCs after 72 h incubation with non-CM or CM obtained from control (Con) or Ihh-silenced AML12 hepatocytes and then assayed for Opn, Timp1, and Col1a1 mRNA ($*p<0.04$; $p<0.0001$, mean±SEM; n=4). FIG. 8F** is a graph showing control (Con) or TAZ-silenced AML12 hepatocytes that were transduced with a plasmid encoding Ihh or control GFP. Aliquots of the four sets of conditioned medium were assayed for Ihh by ELISA ($*p<0.002$; mean±SEM; n=3). FIG. 8G is a graph showing HSCs that were incubated with conditioned media from the 4 sets of cells in (F) or with non-CM and then assayed for Opn, Timp1, and Col1a1 mRNA ($*p<0.05$; $p<0.004$, $*p<0.0004$, mean±SEM; n=4). Note that bars 2 and 3 for Opn and Col1a1 are significantly different at $p<0.05$.

FIG. 10A is an $^1$H-NMR spectrum of PDSA8-1 polymer in DMSO-d6. FIG. 10B is a GPC profile of PDSA8-1 polymer incubated in 9:1 (v/v) DMF/H2O mixture containing 10 mM GSH for 4 h.

FIG. 11A is an electron micrograph showing the morphology of the Luc siRNA loaded PDSA8-1 NPs in PBS solution (pH 7.4). FIG. 11B is a graph showing the size distribution of the Luc siRNA loaded PDSA8-1 NPs in PBS solution (pH 7.4).

FIG. 12A is a graph showing the Size change of the Luc siRNA loaded PDSA8-1 NPs with the presence of 10 mM GSH. FIG. 12B is an electron micrograph showing the morphology of the Luc siRNA loaded PDSA8-1 NPs incubated in PBS solution containing 10 mM GSH for 4 h.

DETAILED DESCRIPTION

Figure 1A:
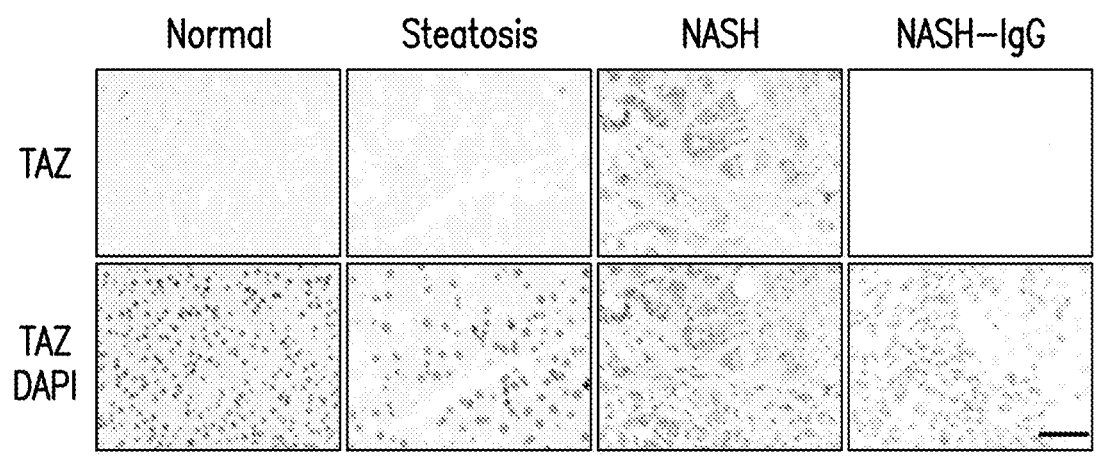
FIGS. 1A-F are immunohistochemistry stains and blots illustrating that TAZ Levels are Increased in the Livers of Humans and Mice with NASH.

Previous NASH studies in mice have relied on the methionine/choline-deficient (MCD) model. Although this model reproduces many of the histological features of NASH (Machado et al., 2015b), MCD mice lose weight and do not develop insulin resistance, in stark contrast to humans with NASH (Hebbard and George, 2011). Other animal models fed various high-fat diets develop obesity, insulin resistance, and steatosis, but they do not develop NASH within a period of time that is feasible for experimentation (Clapper et al., 2013; Ganz et al., 2015). Some of these problems can be overcome through the use of various engineered genetic mutations (Schierwagen et al., 2015), but relevance to the majority of humans who do not have these mutations becomes an issue of concern. To address these concerns, two previous models that incorporated various combinations of high-fat content, fructose, and trans-fatty acids (Charlton et al., 2011; Kohli et al., 2010), which cause primarily steatosis when administered over several months were modified by adding palmitate and cholesterol and by lowering the concentration of certain components that inhibit NASH progression, notably vitamin E. Mice fed this diet for 16 weeks gain weight and develop insulin resistance, hepatic steatosis, inflammation, and early fibrosis.

Using this model, new factors were sought that might promote steatosis-to-NASH progression, particularly liver fibrosis, which is an important predictor of adverse long-term outcomes in NASH (Angulo et al., 2015; Ekstedt et al., 2006; McCullough, 2004). The Hippo pathway transcriptional activator TAZ (also known as WWTR1) (Zhao et al., 2010) was known to exhibit a role in pulmonary fibrosis (Liu et al., 2015). The present data demonstrates a new role for TAZ stemming from the finding that TAZ expression is elevated in the livers of humans with NASH-related fibrosis and in the livers of two murine NASH models, the MCD mouse and the aforementioned obese/insulin-resistant mouse model. Silencing of Taz in hepatocytes in NASH mice suppresses the development of liver inflammation and fibrosis without affecting steatosis. In vitro, conditioned medium from Taz-silenced vs. control hepatocytes decreases fibrotic responses in hepatic stellate cells (HSCs). These results are further linked to decreased hepatocyte secretion of the TAZ target Indian hedgehog (Ihh), a pro-fibrotic factor for HSCs (Bohinc and Diehl, 2012; Syn et al., 2011). Thus, Taz promotes NASH progression and therefore emerges as a therapeutic target to prevent the conversion of steatosis to NASH.

The present results illustrate that the Hippo pathway transcription factor TAZ (WWTR1) is markedly increased in the livers of patients with NASH and in mouse models of NASH. Experiments demonstrating these results utilize a unique and specialized dietary mouse model of NASH which reproduces characteristic features of human NASH including weight gain, insulin resistance, and hepatic inflammation, hepatocyte death, and fibrosis. The present results demonstrate that hepatocyte-specific silencing of TAZ suppresses hepatic inflammation, hepatocyte death, and fibrosis, but not steatosis. In vitro, hepatocyte TAZ induces Indian hedgehog (Ihh), a secretory protein that induces fibrogenesis in hepatic stellate cells. These findings identify TAZ as a previously unrecognized factor that contributes to the important process of steatosis-to-NASH progression.

ABBREVIATIONS

HSCs: hepatic stellate cells;
IHC: immunohistochemistry;
NASH: Nonalcoholic steatohepatitis;
NAFLD: Non-alcoholic fatty liver disease;
Hprt: hypoxanthine guaninephosphoribosyl transferase;
Taz(Wwtr1): WW domain containing transcription regulator 1, encoding the TAZ protein (Reference human nucleotide sequence: NM_015472; Reference human protein sequence: NP_056287);
Tgfβ1: transforming growth factor, beta 1;
Acta2, α-smooth muscle actin;
Vim: vimentin;
Des: desmin;
Col1a1: collagen type I alpha 1;
Col1a2: collagen type I alpha 2;
Col3a1: collagen, type III, alpha 1;
F4/80 (Adgre1): adhesion G protein-coupled receptor E1;
Tnfα: tumor necrosis factor alpha;
Mcp1: monocyte chemoattractant protein-1;
Ihh: Indian hedgehog;
Gli2: GLI family zinc finger 2;
Gli3: GLI family zinc finger 3;
Opn: osteopontin;
Timp1: tissue inhibitor of metalloproteinase 1
Cpt1b: carnitine palmitoyltransferase 1B;
Pparg: peroxisome proliferator-activated receptor-γ;
Scdl: stearoyl-CoA desaturase;
Fasn: fatty acid synthase;
Acaca: acetyl-CoA carboxylase-α;
Cd3: CD3 antigen;
Cd20: B-lymphocyte antigen;
Ihh intron: specific TAZ/TEAD binding area in $1^{st}$ intron of Ihh gene;
Ihh non-specific: non-specific TAZ/TEAD binding site in mouse Ihh gene distal promoter.
TEA; transcriptional enhancer factor.
TEAD1: TEA Domain Family Member 1 (also known as SV40 Transcriptional Enhancer Factor or TEF-1), (Reference human nucleotide sequence: NM_021961; Reference human protein sequence: NP_068780).
TEAD2: Transcriptional enhancer factor TEF-4 also known as TEA domain family member 2. (Reference human nucleotide sequence: NM_001256658; Reference human protein sequence: NP_001243587).
TEAD3: TEA domain transcription factor 3 encodes transcriptional enhancer factor TEF-5. (Reference human nucleotide sequence; NM_003214; Reference human protein sequence: NP_003205).
TEAD4: TEA Domain Family Member 4; (Reference human nucleotide sequence: NM_003213; Reference human protein sequence: NP_003204).
YAP: Yes-associated protein 1, the gene encoding this protein is known as YAP1 or YAP65 (Reference human nucleotide sequence:_NM_001282101; Reference human protein sequences: UniProtKB/Swiss-Prot P46937.2 or NCB1 NP_001 123617.1).

DEFINITIONS

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies.

"Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human, including a human patient.

"Treat" or "treating" refers to administering a therapeutic agent, such as a composition containing any of the liver targeted viral vectors, RNAi, shRNA or other TAZ inhibitors, or similar compositions described herein, internally or externally to a subject or patient having one or more disease symptoms, or being suspected of having a disease or being at elevated at risk of acquiring a disease, for which the agent has therapeutic activity. Gene editing technology such as CRISPR/cas9 methods may also be utilized to carry out liver specific reduction of TAZ and/or related TAZ co-factors such as one or more inhibitors of IHH or TEAD1-TEAD-4. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses transfection of any of the liver-targeted viral vectors, delivery of RNAi, shRNA or other TAZ inhibitors, or similar compositions, including gene editing technology such as CRISPR/cas9 methods, which may be utilized to carry out liver specific reduction of TAZ and/or related TAZ co-factors such as one or more inhibitors of IHH, or TEAD1-TEAD-4, or related methods described herein as applied to a human or animal subject, a cell, tissue, physiological compartment, or physiological fluid.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as anRNA, has been introduced.

The term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

Nucleic Acids

The invention also comprises certain constructs and nucleic acids encoding the complete or portions of the TAZ protein described herein. Certain constructs and sequences, including selected TAZ inhibitory sequences SEQ ID NO:1, SEQ ID NO:2, and any of SEQ ID NO:55-SEQ ID NO:72, or SEQ ID NO:81 may be useful in certain embodiments.

Preferably, the nucleic acids hybridize under low, moderate or high stringency conditions. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

Inhibitory Nucleic Acids that Hybridize to TAZ or YAP

It is noted that in addition to TAZ, YAP induced liver fibrosis is another process which could potentially be blocked by inhibitory compounds in a similar manner as described herein for TAZ. Any number of means for inhibiting TAZ and/or YAP activity or gene expression can be used in the methods of the invention. For example, a nucleic acid molecule complementary to at least a portion of a human TAZ and/or YAP encoding nucleic acid can be used to inhibit TAZ and/or YAP gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through an mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference, or RNAi" a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659

(1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of TAZ/YAP, siRNAs to the gene encoding the TAZ/YAP can be specifically designed using computer programs. Illustrative nucleotide sequences encoding the amino acid sequences of the various YAP isoforms are known and published, e.g., in GenBank Accession Nos. NM.sub.—001130145.21wdarw.NP.sub.—001123617.1 yorkie homolog isoform 1; NM.sub.—006106.4.fwdarw.NP.sub.—006097.2 yorkie homolog isoform 2; NM.sub.—001195044.1.fwdarw.NP.sub.—001181973.1 yorkie homolog isoform 3; 3.NM.sub.—001195045.1.fwdarw.NP.sub.—001181974.1 yorkie homolog isoform 4. Furthermore, exemplary nucleotide sequences encoding the amino acid sequences of the various TAZ isoforms are known and published, e.g., in GenBank Accession Nos. NM.sub.—001168278.1.fwdarw.NP.sub.—001161750.1;2.NM.sub.—001168280.1.fwdarw.NP.sub.—001161752.1;NM.sub.—015472.4.fwdarw.NP.sub.—056287.1; see also, Kanai, et al., The EMBO Journal (2000) 19(24):6778-6791.

Software programs for predicting siRNA sequences to inhibit the expression of a target protein are commercially available and find use. One program, siDESIGN from Dharmacon, Inc. (Lafayette, Colo.), permits predicting siRNAs for any nucleic acid sequence, and is available on the internet at dharmacon.com. Programs for designing siRNAs are also available from others, including Genscript (available on the internet at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

Any suitable viral knockdown system could be utilized for decreasing TAZ mRNA levels—including AAV, lentiviral vectors, or other suitable vectors that are capable of being targeted specifically to the liver. (See Zuckerman and Davis 2015).

Additionally, specifically targeted delivery of shTaz mRNA or other TAZ blocking molecule (nucleic acid, peptide, or small molecule) could be delivered by targeted liposome, nanoparticle or other suitable means.

As described herein we provide methods as well as one or more agents/compounds that silence or inhibit TAZ for the treatment, prophylaxis or alleviation of NASH, or related liver conditions, or predisposition to such a condition.

An approach for therapy of such disorders is to express anti-sense constructs directed against TAZ polynucleotides as described herein, and specifically administering them to liver cells, to inhibit gene function and prevent one or more of the symptoms and processes associated with the progression of steatosis to NASH. Such treatment may also be useful in treating patients who already exhibit a progression to NASH, to reverse or alleviate one or more of the disease processes. Additionally, approaches utilizing one or more additional inhibitors including an inhibitor of Indian hedgehog (Ihh), an inhibitor of YAP, an inhibitor of TEAD1, TEAD2, TEAD3, TEAD4, or any combination of these, are also expected to be useful for treating certain conditions. In certain instances, administering at least one additional therapeutic agent for treatment of any of the following conditions including: steatosis hepatis, steatohepatitis, non-alcoholic fatty liver disease, non-alcoholic steatohepatitis, adiposity and combinations thereof may be useful. Such additional therapeutic agents include antidiabetic drugs and insulin sensitizers including: Rosiglitazone; Pioglitazone; Losartan; Simtuzumab (anti-LOXL2); GR-MD-02; Obeticholic acid (OCA) and combinations thereof.

Anti-sense constructs may be used to inhibit gene function to prevent progression of steatosis to NASH. Antisense constructs, i.e., nucleic acid, such as RNA, constructs complementary to the sense nucleic acid or mRNA, are described in detail in U.S. Pat. No. 6,100,090 (Monia et al.), and Neckers et al., 1992, Crit Rev Oncog 3(1-2):175-231.

In a particular example, NASH may be treated or prevented by reducing the amount, expression or activity of TAZ in whole or in part in hepatocytes, for example by siRNAs capable of binding to and destroying TAZ mRNA. Examples of such anti-TAZ agents/compounds are provided herein, which function to downregulate TAZ by RNA interference. The anti-TAZ agent/compound may comprise a Small Interfering RNA (siRNA) or Short Hairpin RNA (shRNA). A specific example of an anti-TAZ agent includes SEQ ID NO:1, SEQ ID NO:2, and any of SEQ ID NO:55-SEQ ID NO:72 and SEQ ID NO:81, which may be useful in certain embodiments as described below and in the Examples.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the TAZ nucleic acid sequence.

Alternatively, double-stranded (ds) RNA is a powerful way of interfering with gene expression in a range of organisms that has recently been shown to be successful in mammals (Wianny and Zernicka-Goetz, 2000, Nat Cell Biol 2:70-75). Double stranded RNA corresponding to the sequence of a TAZ polynucleotide can be introduced into or expressed in oocytes and cells of a candidate organism to interfere with TAZ activity.

Other methods of modulating TAZ gene expression are known to those skilled in the art and include dominant negative approaches. An example of this approach, which could be utilized in the context of inhibiting, preventing, or treating NASH and NASH related conditions is utilizing a TAZ mutant such as TAZ S51A to block TAZ/TEAD interaction or a small molecule chemical or mimetic which can block TAZ/TEAD interaction. (Zhang H, et al., J Biol Chem. 2009 May 15; 284(20):13355-62). TAZ WW domain mutations also block its binding to some transcriptional factors. Other TAZ peptide inhibitors are described in WO2015063747A2. Yet another approach is to use non-functional variants of TAZ polypeptide that compete with the endogenous gene product resulting in inhibition of function. Inhibitors of TAZ co-factors TEAD1,TEAD2, TEAD3, and TEAD4 can be targeted, and these are also expected to serve as useful in the context of inhibiting, preventing, or treating NASH and NASH related conditions.

TAZ gene expression may also be modulated by introducing peptides or small molecules which inhibit gene expression or functional activity. Thus, compounds identified by the assays described herein as binding to or modulating, such as down-regulating, the amount, activity or expression of TAZ polypeptide may be administered to liver hepatocyte cells to prevent the function of TAZ polypeptide. Such a compound may be administered along with a pharmaceutically acceptable carrier in an amount effective to down-regulate expression or activity TAZ, or by activating or down-regulating a second signal which controls TAZ expression, activity or amount, and thereby alleviating the abnormal condition.

Alternatively, gene therapy may be employed to control the endogenous production of TAZ by the relevant cells such as liver cells in the subject. For example, a polynucleotide encoding a TAZ siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-TAZ siRNA such that the packaging cell now produces infectious viral particles containing the sequence of interest. These producer cells may be administered to a subject for engineering cells in vivo and regulating expression of the TAZ polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of TAZ is decreased in a liver cell. Furthermore, in such embodiments, treatment may be targeted to, or specific to, liver cells. The expression of TAZ may be specifically decreased only in diseased liver cells (i.e., those cells which are predisposed to the liver condition, or exhibiting liver disease already), and not substantially in other non-diseased liver cells. In these methods, expression of TAZ may not be substantially reduced in other cells, i.e., cells which are not liver cells. Thus, in such embodiments, the level of TAZ remains substantially the same or similar in non-liver cells in the course of or following treatment.

Liver cell specific reduction of TAZ levels may be achieved by targeted administration, i.e., applying the treatment only to the liver cells and not other cells. However, in other embodiments, down-regulation of TAZ expression in liver cells (and not substantially in other cell or tissue types) is employed. Such methods may advantageously make use of liver specific expression vectors, for liver specific expression of for example siRNAs, as described in further detail below.

TAZ Nucleic Acids

The methods and compositions described here may employ, as a means for detecting expression levels of TAZ, TAZ polynucleotides, TAZ nucleotides and TAZ nucleic acids, as well as variants, homologues, derivatives and fragments of any of these. In addition, we disclose particular TAZ fragments useful for the methods of diagnosis described here. The TAZ nucleic acids may also be used for the methods of treatment or prophylaxis described.

The terms "TAZ polynucleotide", "TAZ nucleotide" and "TAZ nucleic acid," "Taz nucleic acid" may be used interchangeably, and should be understood to specifically include both cDNA and genomic TAZ sequences. These terms are also intended to include a nucleic acid sequence capable of encoding a TAZ polypeptide and/or a fragment, derivative, homologue or variant of this. SEQ ID NO:1, SEQ ID NO:2, and any of SEQ ID NO:55-SEQ ID NO:72 and SEQ ID NO:81 may be useful in certain embodiments as primers amplifying Taz or as sequences utilized for designing nucleic acid inhibitors (shRNA or RNAi) of TAZ, as shown in the table below. The primer sequences described herein are shown as DNA sequences; however in certain instances it would be useful to utilize the RNA equivalent, in which the sequence is identical, except the T is replaced with U.

TABLE 1

Taz-specific polynucleotides siRNA
(T can be replaced with U for any of the primers listed below, in certain instances.)

| | | Primers can also be useful as RNA if T is replaced with U (T/U) |
|---|---|---|
| SEQ ID NO: 55 | TCATTGCGAGATTCGGCTG | T/U |
| SEQ ID NO: 56 | GATGAATCCGTCCTCGGTG | T/U |
| SEQ ID NO: 57 | GAGGCAAGTTGAAAGGTCAGAGGCA | T/U |
| SEQ ID NO: 58 | GCTGCACCACGTTCTGCCTTTGTAC | T/U |
| SEQ ID NO: 59 | GGCAATGACGTCCTTAGCTGTTTAG | T/U |
| SEQ ID NO: 60 | AGGCAGCTTGGTCCAGGAAGTGATT | T/U |
| SEQ ID NO: 61 | ACCTCTTCAACTCTGTCATGAA | T/U |
| SEQ ID NO: 62 | CGCCCTTTCTAACCTGGCTGTA | T/U |
| SEQ ID NO: 63 | TGCCACCGTTCATCATTTTCCTGCT | T/U |
| SEQ ID NO: 64 | TCCCCGAGTCCCCAGAAAGATGAAT | T/U |
| SEQ ID NO: 65 | CCAGCTCATGGCGGAAAAAGATCCT | T/U |

TABLE 1-continued

Taz-specific polynucleotides siRNA
(T can be replaced with U for any of the primers listed below, in certain instances.)

| | | Primers can also be useful as RNA if T is replaced with U (T/U) |
|---|---|---|
| SEQ ID NO: 66 | ACCCCAGGAAGGTGATGAATCAGCC | T/U |
| SEQ ID NO: 67 | GGGCCTTGCGGACCAAGTGATGAGG | T/U |
| SEQ ID NO: 68 | GCCCTTGACTGTTTACTAATAGATA | T/U |
| SEQ ID NO: 69 | CCAAATCCATCAGATGAAACCATTT | T/U |
| SEQ ID NO: 70 | GCCTGCATTTCTGTGGCAGATA | T/U |
| SEQ ID NO: 71 | GCCATGAGCACAGATATGAGATCT | T/U |

Where reference is made to a TAZ nucleic acid, this should be taken as a reference to any member of the TAZ family of nucleic acids. Of particular interest are TAZ nucleic acids selected from the group consisting of: NM_015472, NM_133784, NM_001037696, XM_001193047 and NM_001024869, as well as NM_001168280; NM_001168278; XM_011512661; NM_001168281. For example, the TAZ nucleic acid may comprise a human. TAZ sequence having GenBank Accession Number NM_015472.

In certain instances the following RNA sequences are useful:
the target sequence of mouse Ihh siRNA: UGC GGA CAA UCA UAC AGA ACC AGC A (SEQ ID NO:82);
target sequence of mouse Ihh siRNA: ACC ACC UUC AGU GAU GUG CUU A (SEQ ID NO:83);
a target sequence of human Taz siRNA: GGA UAC UAG UUG UGA AAU GGA AAG A (SEQ ID NO:84).

TAZ nucleic acids may be used for a variety of means, for example, administration to an individual suffering from, or suspected to be suffering from, NASH, or related liver conditions, or predisposition to such a condition, for the treatment thereof. The expression of elevated levels of TAZ nucleic acids may be detected for diagnosis or detection of NASH, or related liver conditions, or predisposition to such a condition. Such a "TAZ diagnostic NASH" test would utilize a liver biopsy in order to obtain a suitable patient test sample. Preliminary data indicates that in humans with NASH, TAZ protein levels are elevated in the range of 5-20 fold above normal. A bank of human non-NASH liver specimens would provide an average baseline immunoblot signal using densitometry quantification based on β-actin load. Values ≥2-fold greater than the averaged baseline would be indicative of a NASH diseased condition, or likelihood of progression to NASH. Methods including IHC would be useful in detecting elevated TAZ levels. With respect to Taz mRNA expression, 2-3 fold increased levels over normal are seen in the FPC model. The data described herein indicate that Taz nucleic acid levels or TAZ protein liver levels would be a good marker of risk for progression of benign steatosis to clinically significant NASH. RNAseq is another method that may be useful for such testing. Additionally, monitoring samples for elevated levels of Taz nucleic acids in patients undergoing treatments as described herein, may provide an indication of treatment efficacy and/or effectiveness. Taz nucleic acids may also be used for the expression or production of TAZ polypeptides. Additionally, methods for diagnosing NASH or susceptibility to NASH in a human subject can also utilize detecting an elevated level of TAZ, Indian hedgehog (Ihh), YAP, TEAD1, TEAD2, TEAD3, TEAD4, or any combination of these proteins, wherein an elevated level above baseline, of any one or more of these proteins: TAZ, Indian hedgehog (Ihh), YAP, TEAD1, TEAD2, TEAD3, TEAD4 indicates susceptibility to NASH or ongoing NASH in the human subject.

SEQ ID NO:1, SEQ ID NO:2, and any of SEQ ID NO:55-SEQ ID NO:72 and SEQ ID NO:81 may be useful in certain embodiments as primers amplifying Taz or as sequences utilized for designing nucleic acid inhibitors (Taz shRNA or RNAi), as shown in Table 1. Such sequences are expected to be useful in diagnostic and methods for detecting NASH or susceptibility to NASH, and for monitoring treatment by any of the methods as described herein.

By "down-regulation" included is any negative effect on the, condition being studied; this may be total or partial. Thus, where binding is being detected, candidate antagonists are capable of reducing, ameliorating, or abolishing the binding between two entities. The down-regulation of binding (or any other activity) achieved by the candidate molecule may be at least 10%, such as at least 20%, at least 30%, at least 40%, at least 50%, at least 60%, at least 70%, at least 80%, at least 90% or more compared to binding (or whichever activity) in the absence of the candidate molecule. Thus, a candidate molecule suitable for use as an antagonist is one which is capable of reducing by at least 10% the binding or other activity.

The term "compound" refers to a chemical compound (naturally occurring or synthesized), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

Examples of potential antagonists of TAZ include antibodies, small molecules, nucleotides and their analogues, including purines and purine analogues, oligonucleotides or proteins which are closely related to a binding partner of TAZ, e.g., a fragment of the binding partner, or small molecules which bind to the TAZ polypeptide but do not elicit a response, so that the activity of the polypeptide is prevented, etc.

In some embodiments, the anti-TAZ agent is provided as an injectable or intravenenous composition and administered accordingly. The dosage of the anti-TAZ agent inhibitor may be between about 5 mg/kg/2 weeks to about 10 mg/kg/2 weeks. The anti-TAZ agent inhibitor may be provided in a dosage of between 10-300 mg/day, such as at least 30 mg/day, less than 200 mg/day or between 30 mg/day to 200 mg/day.

The anti-TAZ agent may downregulate TAZ by RNA interference, such as by comprising a Small Interfering RNA (siRNA) or Short Hairpin RNA (shRNA).

Additionally, TAZ polypeptide fragments could be utilized as inhibitors, for example See, WO2015063747A2, which describes peptides that block TAZ/TEAD interaction.

TAZ polypeptides or polypeptide fragments comprising amino acid sequences that are at least about 70% identical, preferably at least about 80% identical, more preferably at least about 90% identical and most preferably at least about 95% identical (e.g., 95%, 96%, 97%, 98%, 99%, 100%) to the mouse TAZ or human TAZ amino acid sequences with reference to sequences described above, are contemplated with respect to inhibiting TAZ expression and or function, when the comparison is performed by a BLAST algorithm wherein the parameters of the algorithm are selected to give the largest match between the respective sequences over the entire length of the respective reference sequences. Polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference TAZ amino acid sequences when the comparison is performed with a BLAST algorithm wherein the parameters of the algorithm are selected to give the largest match between the respective sequences over the entire length of the respective reference sequences, are also included in constructs and methods of the present invention.

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, DC; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, DC; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

In certain aspects, the present invention also provides expression vectors comprising various nucleic acids, wherein the nucleic acid is operably linked to control sequences that are recognized by a host cell when the host cell is transfected with the vector.

Pharmaceutical Compositions and Administration

To prepare pharmaceutical or sterile compositions of the compositions of the present invention, the viral vectors, RNAi, shRNA or other TAZ inhibitors, or similar compositions may be admixed with a pharmaceutically acceptable carrier or excipient. See, e.g., *Remington's Pharmaceutical Sciences* and *U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

Toxicity and therapeutic efficacy of the therapeutic compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, therapeutic compositions exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In an embodiment of the invention, a composition of the invention is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the composition or therapeutic can be administered by an invasive route such as by injection (see above). In further embodiments of the invention, the composition, therapeutic, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

Alternately, one may administer the viral vectors, RNAi, shRNA or other TAZ inhibitors, or related compound in a local rather than systemic manner, for example, via injection of directly into the desired target site, often in a depot or sustained release formulation. Furthermore, one may administer the composition in a targeted drug delivery system, for example, in a liposome coated with a tissue-specific antibody, targeting, for example, the liver, and more specifically hepatocytes. The liposomes will be targeted to and taken up selectively by the desired tissue. Also included in a targeted drug delivery system is nanoparticle specific liver delivery of the viral vectors, RNAi, shRNA or other TAZ inhibitors, or TAZ-based compound, alone or in combination with an Ihh RNAi construct or similar inhibitors. A summary of various delivery methods and techniques of siRNA administration in ongoing clinical trials is provided in Zuckerman and Davis 2015; Nature Rev. Drug Discovery, Vol. 14: 843-856, December. 2015.

Any of the therapeutics described herein including: an inhibitor of TAZ, inhibitor of Indian hedgehog (Ihh), an inhibitor of YAP, an inhibitor of TEAD1, TEAD2, TEAD3, TEAD4, or any combination thereof, can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.,* 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.,* 16, 129-140; Holland and Huang, 1999, *Handb. Exp. Pharmacol.,* 137, 165-192; and Lee et al., 2000, ACS Symp. Ser., 752, 184-192. U.S. Pat. No. 6,395,713 and PCT Publication No. WO 94/02595 further describe the general methods for delivery of nucleic acid molecules. These protocols can be utilized for the delivery of virtually any nucleic acid molecule.

Any of the therapeutics described herein including; an inhibitor of TAZ, inhibitor of Indian hedgehog (Ihh), an inhibitor of YAP, an inhibitor of TEAD1, TEAD2, TEAD3, TEAD4, or any combination thereof can also be administered to a desired target by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (see PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *1 Clin. Cancer Res.,* 5, 2330-2337 and PCT Publication No. WO 99/3 1262.

Therapeutic compositions comprising surface-modified liposomes containing poly(ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). The long-circulating liposomes enhance the pharmacokinetics and pharmacodynamics of. DNA and RNA, particularly compared to conventional cationic liposomes which are known to accumulate in tissues of the MPS (Liu et al., J. Biol. Chem. 1995, 42, 24864-24870; PCT Publication No. WO 96/10391; PCT Publication No. WO 96/10390; and PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The administration regimen depends on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects. Accordingly, the amount of biologic delivered depends in part on the particular therapeutic composition and the severity of the condition being treated.

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a viral vector, RNAi, shRNA or other TAZ inhibitors or inhibitor compound of the invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the compound sufficient to result in at least partial amelioration of symptoms, e.g., treatment, healing, prevention or amelioration of the relevant medical condition, or an increase in rate of treatment, healing, prevention or amelioration of such conditions.

When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

The present invention also provides kits comprising the components of the combinations of the invention in kit form. A kit of the present invention includes one or more components including, but not limited to, the viral vectors, RNAi, shRNA or other TAZ inhibitors, or TAZ/YAP/IHH-based inhibitor compounds, as discussed herein, in association with one or more additional components including, but not limited to a pharmaceutically acceptable carrier and/or a chemotherapeutic agent, as discussed herein. The viral vectors, RNAi, shRNA or other TAZ inhibitors, or TAZ/YAP/IHH-based inhibitor compounds, composition and/or the therapeutic agent can be formulated as a pure composition or in combination with a pharmaceutically acceptable carrier, in a pharmaceutical composition.

Kits may also include primers, buffers, and probes along with instructions for determining elevated levels of nucleic acid, proteins, or protein fragments of TAZ, Indian hedgehog (Ihh), YAP, TEAD1, TEAD2, TEAD3, TEAD4, or any combination thereof.

In one embodiment, a kit includes the viral vectors, RNAi, shRNA, or other TAZ inhibitors, or TAZ/YAP/IHH-based inhibitor compounds/composition of the invention or a pharmaceutical composition thereof in one container (e.g., in a sterile glass or plastic vial) and a pharmaceutical composition thereof and/or a chemotherapeutic agent in another container (e.g., in a sterile glass or plastic vial).

In another embodiment of the invention, the kit comprises a combination of the invention, including the viral vectors, RNAi, shRNA or other TAZ inhibitors, or TAZ/YAP/IHH-based inhibitor compounds, along with a pharmaceutically acceptable carrier, optionally in combination with one or more therapeutic agent components formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

GENERAL METHODS

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

EXAMPLES

TAZ Levels are Increased in the Livers of Humans and Mice With NASH

Figure 1B:
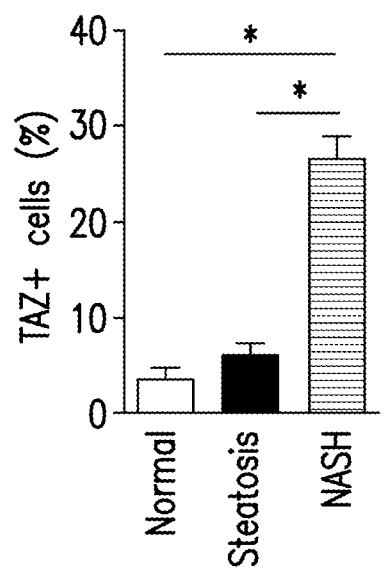
Figure 1C:
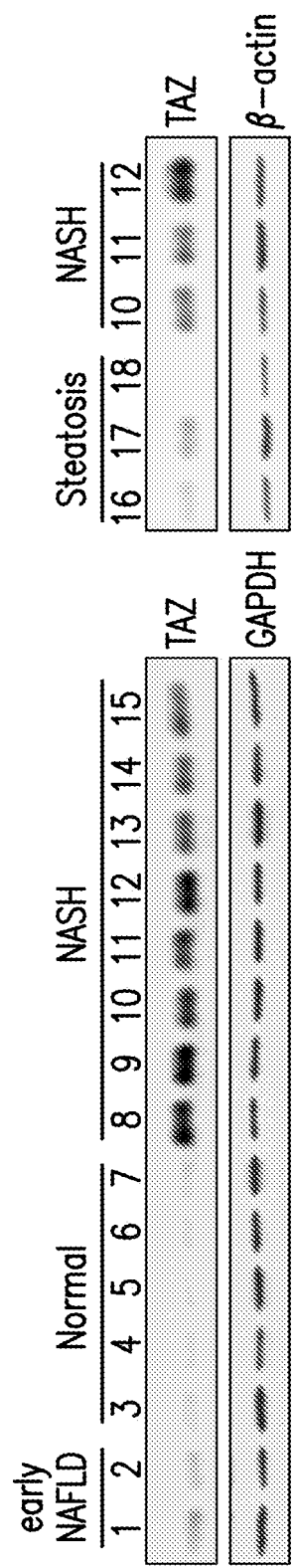

The Hippo pathway transcription factor TAZ contributes to the development of pulmonary fibrosis (Liu et al., 2015). In order to understand whether TAZ plays any role in the development of hepatic fibrosis and NASH progression, NAFLD was evaluated. TAZ immunofluorescence microscopy was conducted on human liver samples from obese individuals with normal, steatotic, and NASH histology. While there was similar TAZ staining in normal and steatotic livers, a significant increase in TAZ staining in the NASH samples was observed (FIGS. 1A-B). The specificity of the anti-human TAZ antibody for immunofluorescence is demonstrated by an siTaz experiment conducted with human HepG2 liver cells. Most of the TAZ-stained cells in human NASH samples were hepatocytes, as identified by HNF4α staining. The Taz protein levels were also analyzed by immunoblot in liver extracts from subjects with NASH vs. early NAFLD and normal liver. The results shown in FIG. 1C illustrate that TAZ was highest in NASH liver.

Figure 1D:
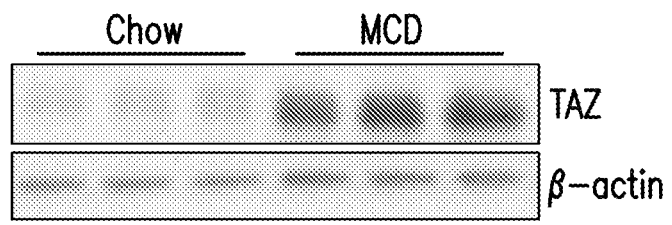

TAZ expression in various mouse models of NASH was examined. The first mouse model utilized was the widely used methionine/choline-deficient (MCD) diet model, which induces NASH-like liver pathology despite weight loss and insulin sensitivity (Hebbard and George, 2011). TAZ expression was markedly higher in MCD liver compared with control liver (FIG. 1D). Studying TAZ in a NASH model that more closely mimicked the human condition with weight gain and insulin resistance was the next goal. For this purpose, two previously described diet-induced weight-gain models (Charlton et al., 2011; Kohli et al., 2010) were modified to achieve robust NASH features within an experimentally acceptable time frame. For this purpose a new diet was developed that was rich in fructose, palmitate, cholesterol (FPC), and trans-fat, with other features as detailed in Tables 2 and 3. The cholesterol was added in view of links between liver cholesterol and NASH in humans (Ioannou, 2016), and in C57BL/6J mice, the strain used here, a high dietary content of cholesterol is needed to achieve adequately increased cholesterol absorption (Jolley et al., 1999). Additionally the vitamin E level was lowered in the new diet, compared with that in standard mouse chow diet, because vitamin E has NASH-protective properties (Sanyal et al., 2010).

TABLE 2

Composition of the fructose-palmitate-cholesterol (FPC) diet.

| Food Component | g/kg diet |
| --- | --- |
| Casein, "Vitamin-Free" | 140.0 |
| Sucrose | 341.5 |
| Maltodextrin | 119.6 |
| Vegetable shortening, hydrogenated (Primex) | 190.0 |
| Anhydrous milk fat | 60.0 |
| Palmitic acid (Nu-Chek-Prep N-16A or Sigma W283207) | 40.0 |
| Cholesterol | 12.5 |
| Cellulose | 50.0 |
| Mineral mix, AIN-76 (170915) | 35.0 |
| Calcium carbonate | 4.0 |
| Vitamin mix, w/o choline, A, D, E (83171) | 5.0 |
| Vitamin E, DL-alpha tocopheryl acetate | 0.1 |
| Vitamin A palmitate | 0.04 |
| Vitamin D3, cholecalciferol | 0.0044 |
| Choline dihydrogen citrate | 2.28 |

| Drinking water | g/L |
| --- | --- |
| 55% glucose/45% fructose solution (w/w) | 42 |

TABLE 3

Caloric composition of chow, fructose-palmitate-cholesterol (FPC), and "fast food" (FF) diets. Estimated nutrient data were calculated from published values and direct analytical testing of raw materials.

|  | Chow diet | FPC diet | FF diet |
| --- | --- | --- | --- |
| Diet source and # | LabDiet Rodent Diet 20, #5053 | Teklad Diets TD.140154 | Test Diet #1810060 |
| Macronutrients |  |  |  |
| Protein, % by weight | 21.0 | 12.6 | 17.4 |
| Carbohydrate, % by weight | 53.5 | 46.2 | 49.9 |
| Fat, % by weight | 5.0 | 28.8 | 20.0 |
| Protein, % kcal | 24.5 | 10.2 | 15.5 |
| Carbohydrate, % kcal | 62.4 | 37.4 | 44.4 |
| Fat, % kcal | 13.1 | 52.4 | 40.1 |
| Methionine, g/kg | 6.2 | 3.4 | 8.0 |
| Sucrose, % by weight | 3.2 | 34 | 34 |
| Cholesterol, % by weight | 0.01 | 1.25 | 0.2 |
| Vitamin E, IU/kg | 99 | 50 | 50 |
| Choline, mg/kg | 1490 | 915 | 918 |
| SFA, % total fatty acids | 20.7 | 46 | 70 |
| cis-MUFA, % total fatty acids | 26 | 24 | 26.7 |
| cis-PUFA, % total fatty acids | 53.3 | 4 | 3.3 |
| Trans-fats, % total fatty acids | N/A | 26 | 0 |
| Trans-fats, % by weight | N/A | 7 | 0 |
| Palmitic Acid, % by weight | N/A | 8.7 | 5.2 |

Figure 2A:
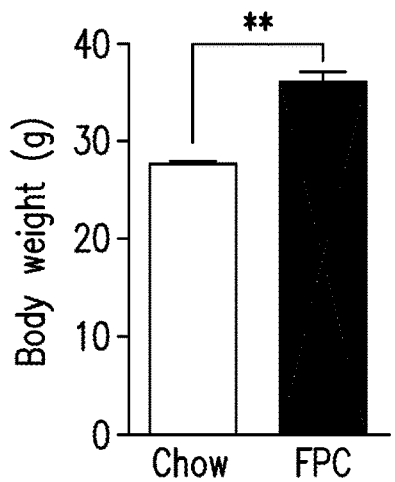
FIGS. 2A-Q are immunohistochemistry stains and blots showing that FPC-fed mice develop weight gain, insulin resistance, and features of NASH. The following parameters were measured in male C57BL/6J mice after 16 weeks on chow or FPC diet ($*p<0.02$, $**p<0.0001$; mean±SEM; n=6 mice/group)
Figure 2B:
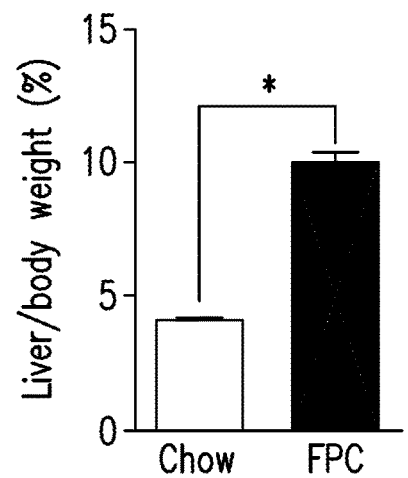
Figure 2C:
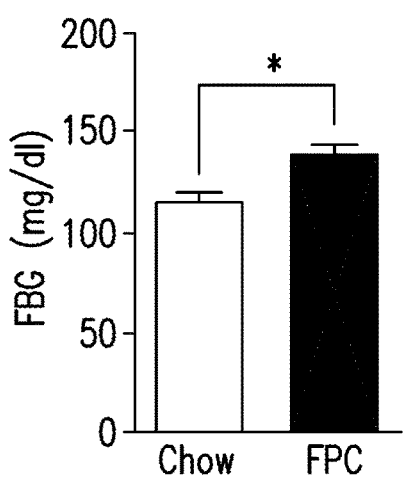
FIG. 2C-E are graphs showing plasma fasting glucose, insulin, ALT, and AST.
Figure 2D:
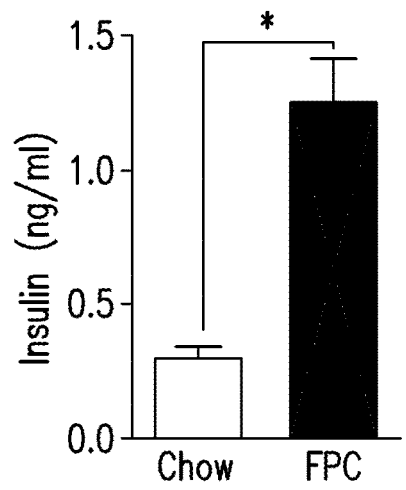
Figure 2E:
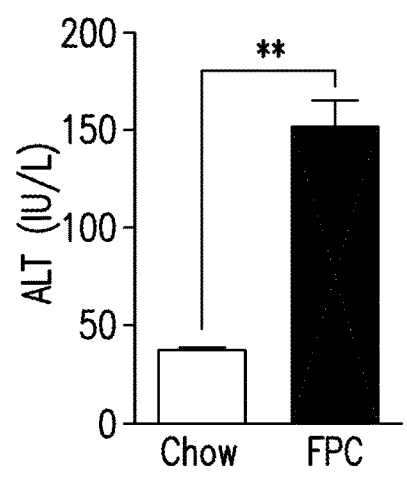
Figure 2E:
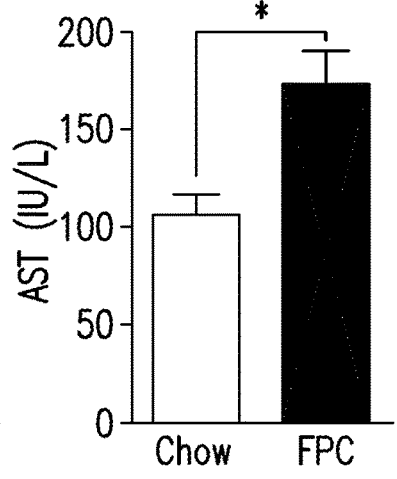
Figure 2F:
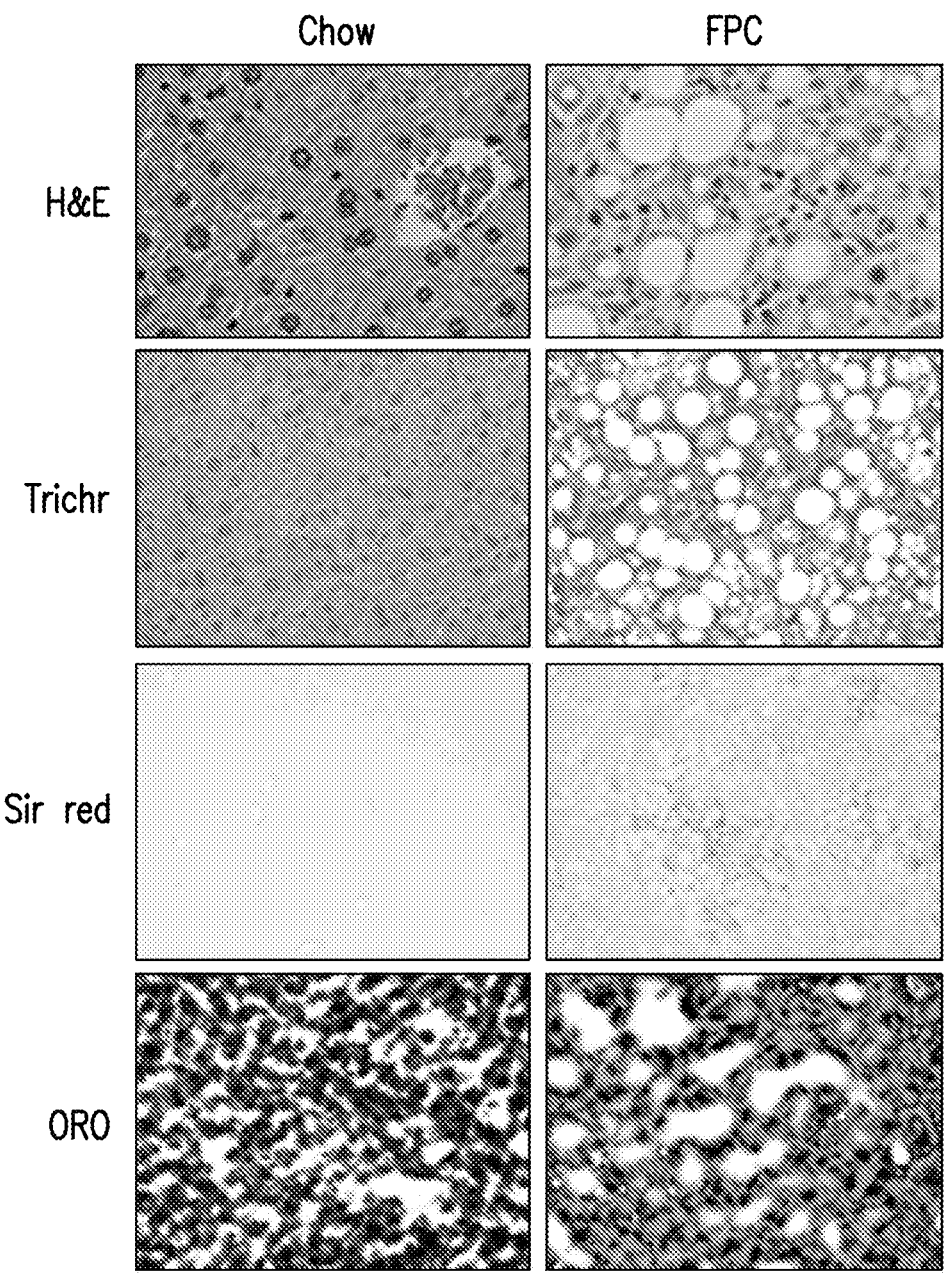
FIG. 2F is immunohistochemistry staining of liver sections with H&E (1st row; Bar, 100 µm), Masson's trichrome (Trichr) (2nd row; Bar, 100 µm), Sirius red (Sir red) (3rd row; Bar, 500 µm), and Oil Red O (ORO)/H&E (4th row; Bar, 100 µm).
Figure 2G:
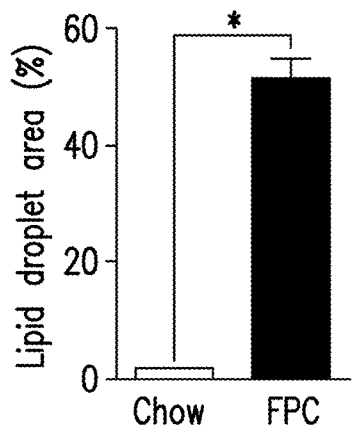
FIG. 2G-J are graphs quantifying lipid droplet area, liver inflammatory cell number, and aniline blue- and Sirius red-positive area.
Figure 2H:
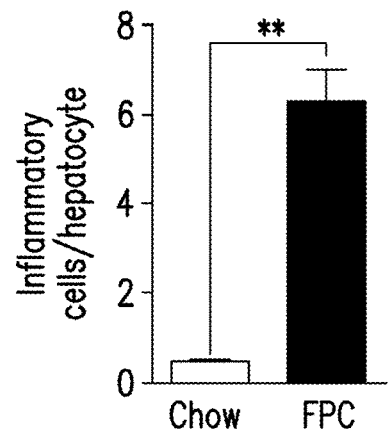
Figure 2I:
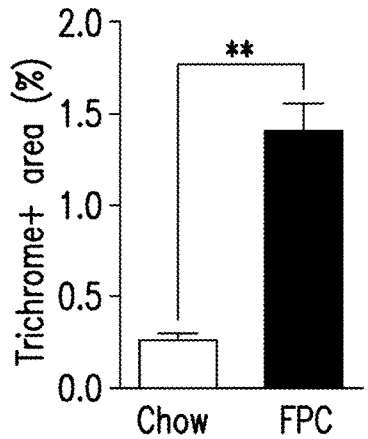
Figure 2J:
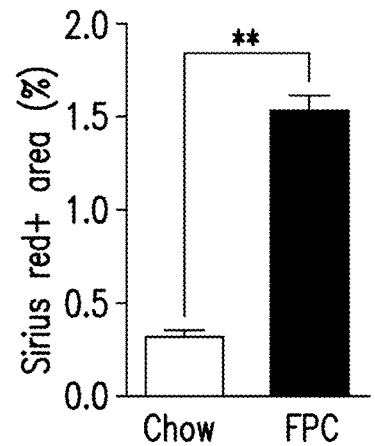
Figure 2K:
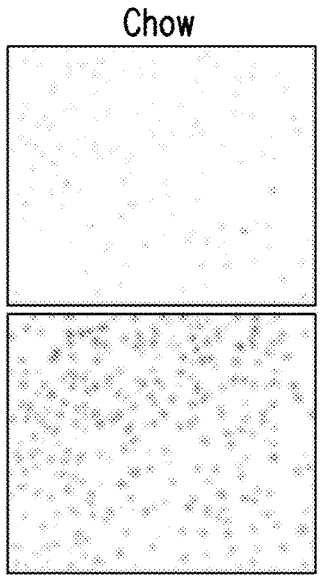
FIG. 2K is immunochemistry TUNEL staining (red) and quantification; DANI counterstain for nuclei is shown in bottom panels; Bar, 100 µm.
Figure 2K:
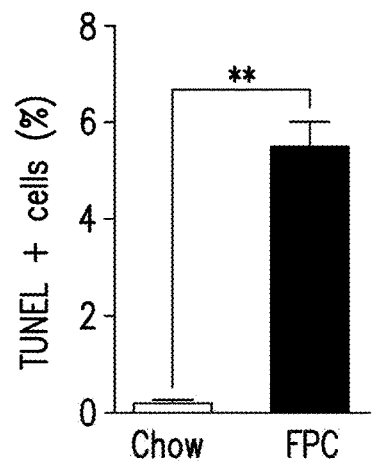
Figure 2L:
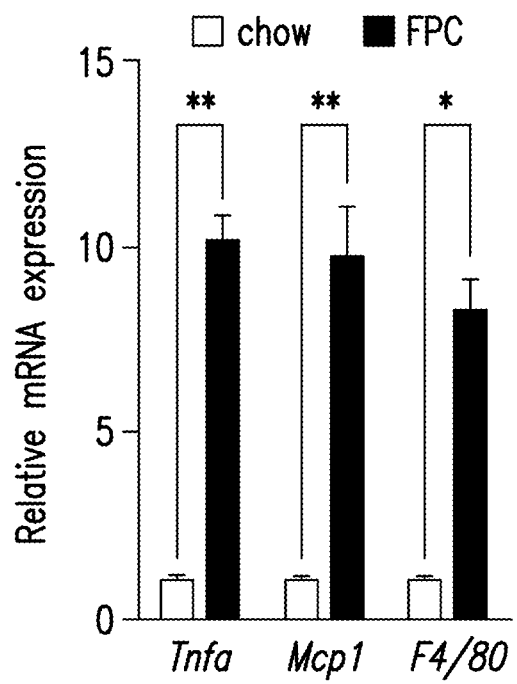
FIG. 2L are graphs showing mRNA levels of Tnfa, Mcp1, and F4/80 (Adgre1).
Figure 2M:
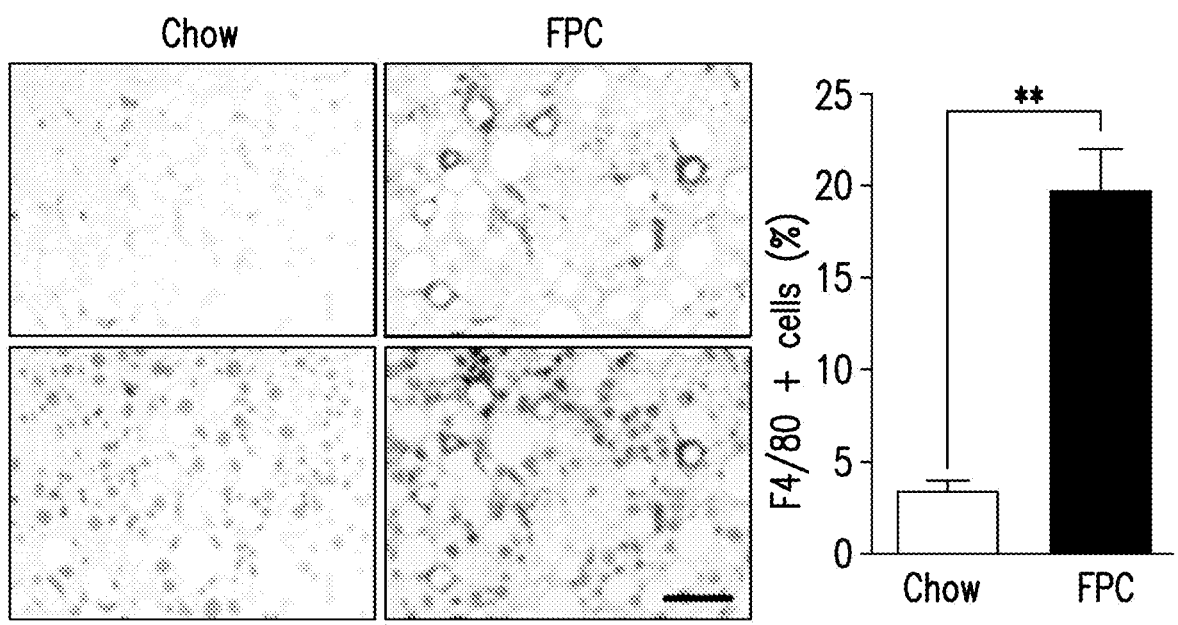
FIG. 2M is immunochemistry F4/80 immunofluorescence (red) and graphic quantification; DAPI counterstain for nuclei is shown in bottom panels; Bar, 100 µm.
Figure 2N:
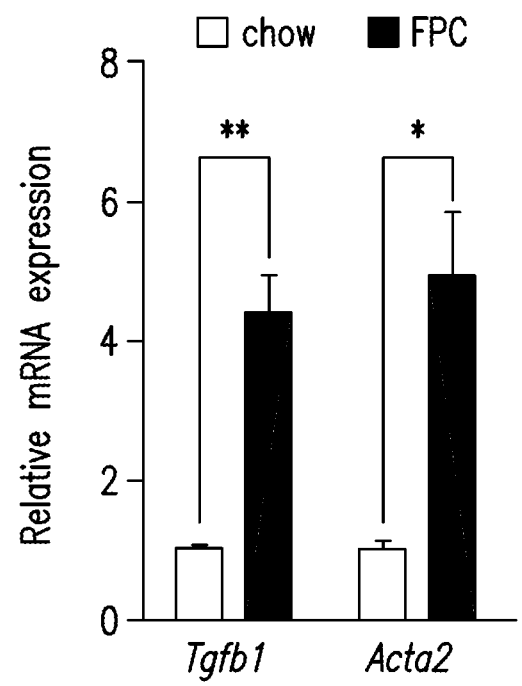
FIG. 2N are graphs showing mRNA levels of Tgfb1 and Acta2 (α-SMA).
Figure 2O:
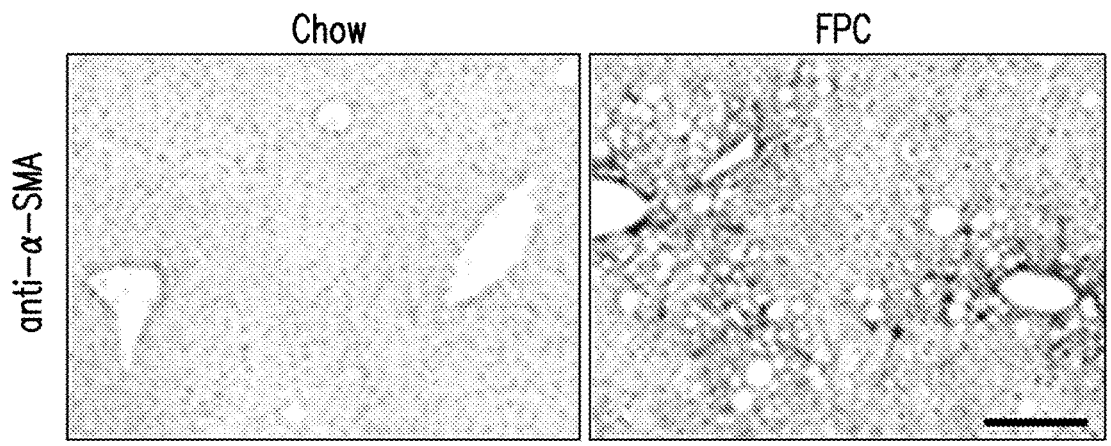
FIG. 2O shows α-SMA immunohistochemistry; Bar, 200 µm.
Figure 2P:
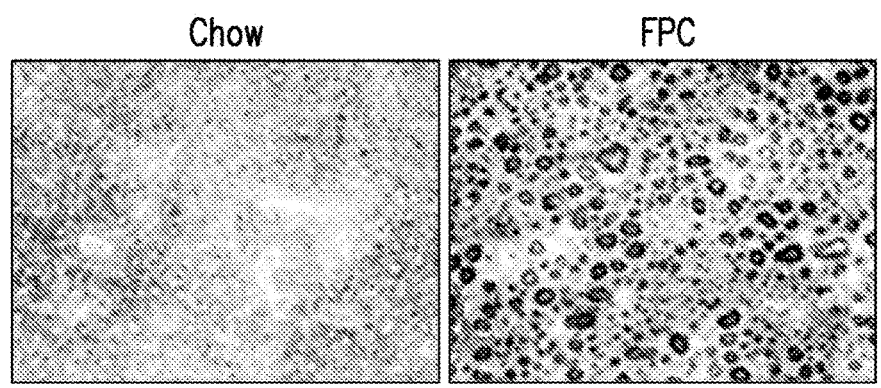
FIG. 2P shows filipin staining; Bar, 200 µm.
Figure 2Q:
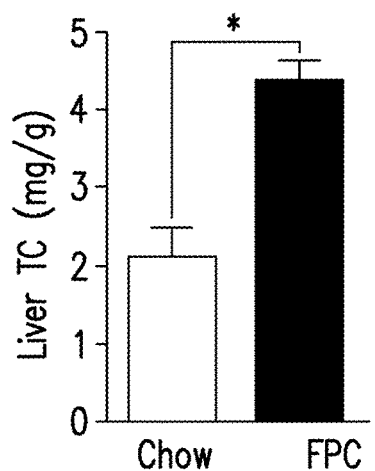
Figure 3A:
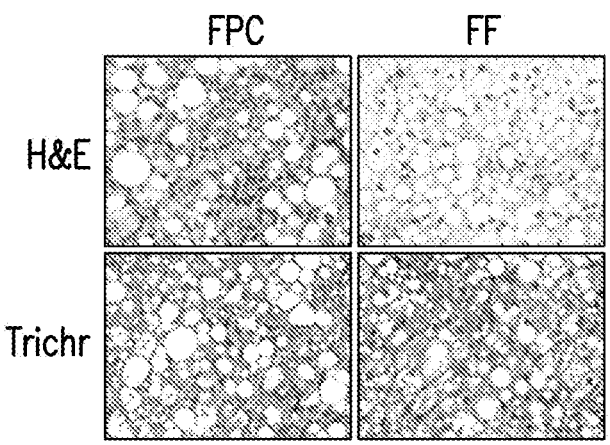
FIG. 3A shows immunohistochemistry staining of liver sections for H&E (upper panels) and Masson's trichrome (Trichr) (lower panels); Bar, 100 µm.
Figure 3B:
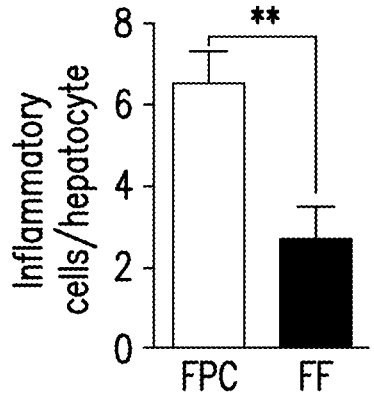
FIG. 3B-C are graphs showing quantification of hepatic inflammatory cells and aniline blue-positive area.
Figure 3C:
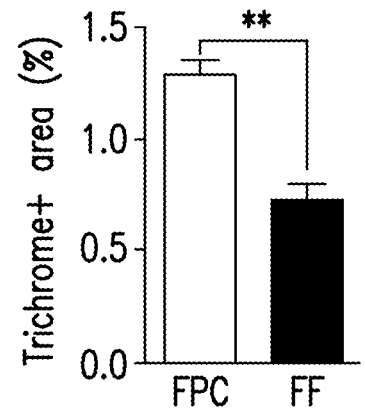
Figure 3D:
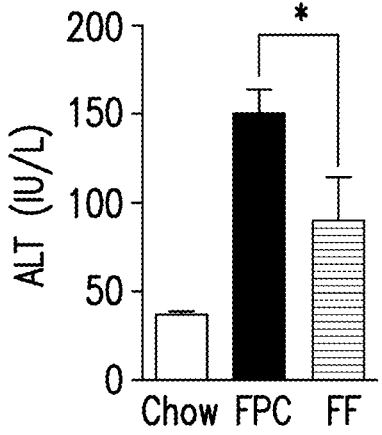
FIG. 3D is a graph showing plasma ALT levels.
Figure 3E:
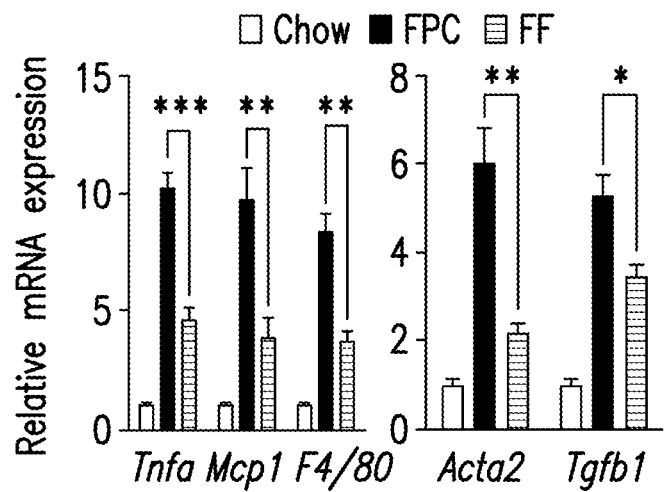
FIG. 3E are graphs showing mRNA levels of Tnfa, Mcp1, F4/80 (Adgre1), Acta2 (α-SMA), and Tgfb1.
Figure 3F:
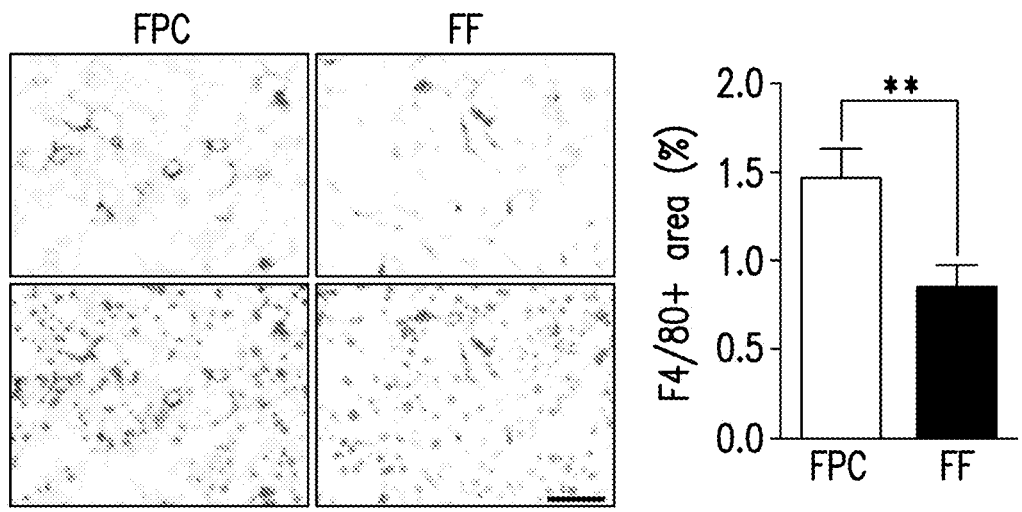
FIG. 3F shows immunohistochemistry F4/80 immunofluorescence (red) and graphic quantification; DAPI counterstain for nuclei is shown in bottom panels; Bar, 100 µm.
Figure 3G:
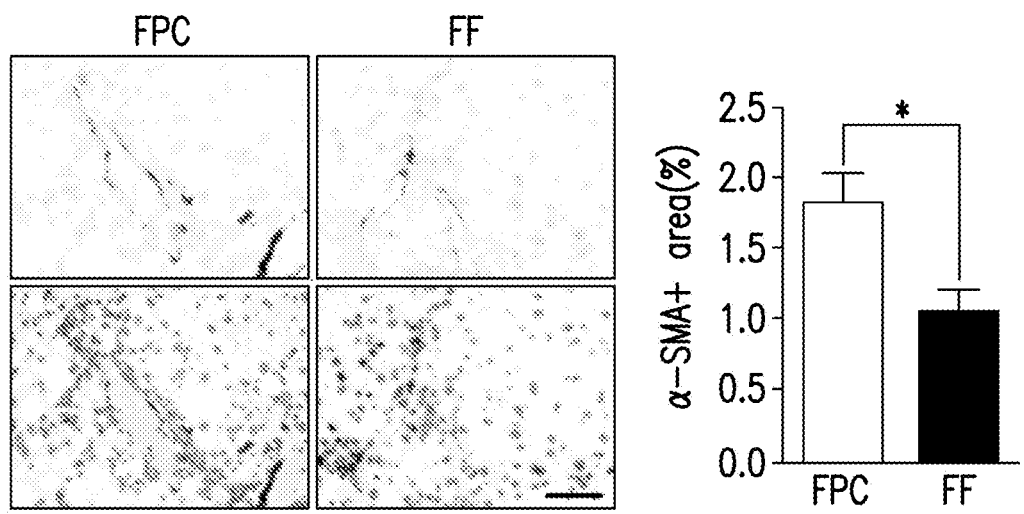
FIG. 3G shows immunohistochemistry α-SMA immunofluorescence (red) and graphic quantification; API counterstain for nuclei is shown in bottom panels; Bar, 100 µm.

After 16 weeks, FPC-fed mice had higher body weight and liver:body weight ratio than chow-fed mice (FIGS. 2A-B). Additionally, FPC mice showed significant increases in fasting blood glucose, plasma insulin, and alanine aminotransferase (ALT) and aspartate aminotransferase (AST) levels (FIGS. 2C-E). In terms of liver histology, lipid droplet area (H&E and Oil Red O [ORO]), inflammatory cells, fibrosis (aniline blue component of trichrome [Trichr] and Sirius red [Sir red]), and cell death (TUNEL) were greater in the livers of FPC-fed mice vs. chow-fed mice (FIGS. 2F-K). As further evidence of inflammation, FPC liver had elevated liver mRNA levels for Tnfa, Mcp1, F4/80 (Adgre1; macrophages) and a higher percentage of F4/80+ cells (FIGS. 2L-M). With regard to fibrosis-associated parameters, hepatic Tgfb1 and Acta2 (β-smooth muscle actin, α-SMA) mRNAs were higher in FPC-fed mice compared with chow-fed mice (FIG. 2N), and there was also an increase in α-SMA+ cells (FIG. 2O). Moreover, as designed, liver cholesterol was elevated in the livers of FPC mice (FIGS. 2P-Q).

Figure 1E:
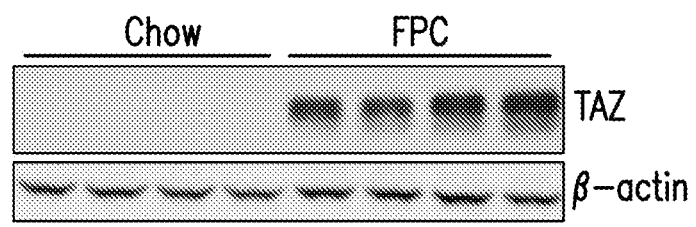
Figure 1F:
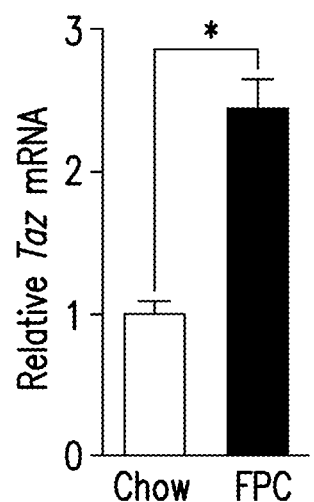

Additional features of the model in terms of blood parameters and liver assays are shown in Table 4 shows hepatic fatty acid changes similar to those reported for human NASH liver (Yamada et al., 2015). Finally, FIGS. 3A-G show a direct comparison of the FPC diet compared with one of the original models referred to as the "fast food" (FF) model (Charlton et al., 2011). Importantly, the livers of FPC mice express high levels of TAZ, including nuclear TAZ (FIG. 1E). Moreover, in view of the fact that the transcriptionally active form of TAZ is non-phosphorylated and nuclear (Liu et al., 2011), these data illustrate that nuclear TAZ was higher in the livers of FPC-fed vs. chow-fed mice and that the ratio of phospho-TAZ:total TAZ was much lower in these livers. Collectively, these data show that TAZ is induced in the livers of humans and mice with NASH and thus raise the possibility that TAZ may be a contributor to the progression from benign steatosis to NASH.

TABLE 4

Saponified fatty acid content of the livers of mice fed the FPC diet for 16 wks (μmol/g liver). P values were calculated using one-way ANOVA with post-hoc Tukey test.

|  | Chow | | | FPC | | | |
| --- | --- | --- | --- | --- | --- | --- | --- |
| FA | Average | SD | % of total FA | Average | SD | % of total FA | P value |
| C14:1 | 1.581 | 0.3316 | 0.1092 | 3.351 | 0.2631 | 0.0964 | 0.0054 |
| C14 | 12.369 | 2.3932 | 0.8544 | 27.687 | 1.0312 | 0.7962 | 0.0025 |
| C16:1 | 81.675 | 15.447 | 5.6421 | 351.48 | 24.869 | 10.107 | 0.0009 |
| C16 | 233.65 | 29.845 | 16.14 | 420.04 | 9.6215 | 12.079 | 0.0018 |
| C18:3 | 43.305 | 6.1274 | 2.9915 | 10.509 | 0.2135 | 0.3022 | 0.0025 |

TABLE 4-continued

Saponified fatty acid content of the livers of mice fed the FPC diet for 16 wks (µmol/g liver). P values were calculated using one-way ANOVA with post-hoc Tukey test.

| FA | Chow | | | FPC | | | |
|---|---|---|---|---|---|---|---|
| | Average | SD | % of total FA | Average | SD | % of total FA | P value |
| C18:2 | 513.51 | 70.787 | 35.473 | 159.21 | 6.8258 | 4.5782 | 0.0031 |
| C18:1 | 383.23 | 51.698 | 26.473 | 2347.5 | 77.063 | 67.506 | 3E−05 |
| C18 | 49.641 | 11.68 | 3.4292 | 44.349 | 4.7849 | 1.2753 | 0.5944 |
| C20:5 | 13.23 | 2.0541 | 0.9139 | 0.63 | 0.2154 | 0.0181 | 0.0021 |
| C20:4 | 47.481 | 5.6404 | 3.28 | 34.143 | 3.9159 | 0.9818 | 0.0243 |
| C20:1 | 4.317 | 0.8123 | 0.2982 | 63.795 | 6.0916 | 1.8345 | 0.0006 |
| C20 | 0.582 | 0.1372 | 0.0402 | 1.386 | 0.2549 | 0.0399 | 0.0105 |
| C22:6 | 62.589 | 8.0908 | 4.3236 | 10.032 | 1.2551 | 0.2885 | 0.0011 |
| C22:1 | 0 | 0 | 0 | 3.051 | 0.7256 | 0.0877 | 0.0053 |
| C22 | 0.423 | 0.1254 | 0.0292 | 0.36 | 0.0945 | 0.0104 | 0.4897 |
| C24:1 | 0 | | 0 | 0 | | 0 | |
| C24 | 0 | | 0 | 0 | | 0 | |

Figure 4A:
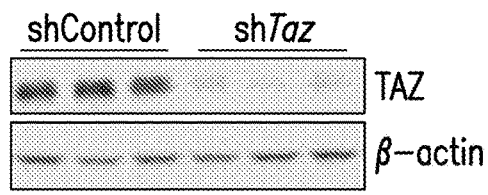
FIGS. 4A-J are immunohistochemistry stains and blots illustrating that TAZ Silencing Reduces Liver Inflammation, Fibrosis, and Cell Death in FPC-Fed Mice. The following parameters were measured in male C57BL/6J mice treated with AAV8-shTaz or control vector and then fed the FPC diet for 16 weeks ($*p<0.05$, $p<0.01$, $*p<0.0002$, mean±SEM; n=10 mice/group)
Figure 4B:
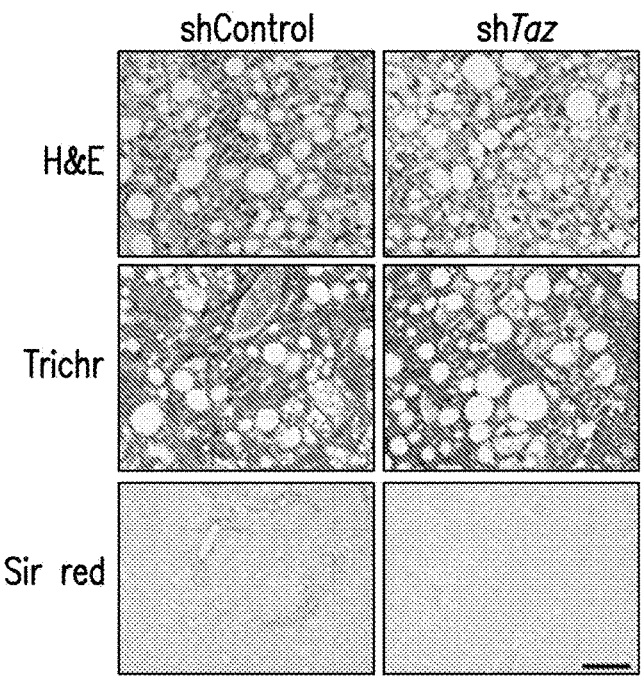
Figure 4C:
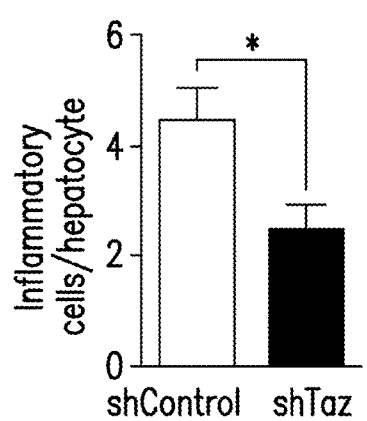
Figure 4D:
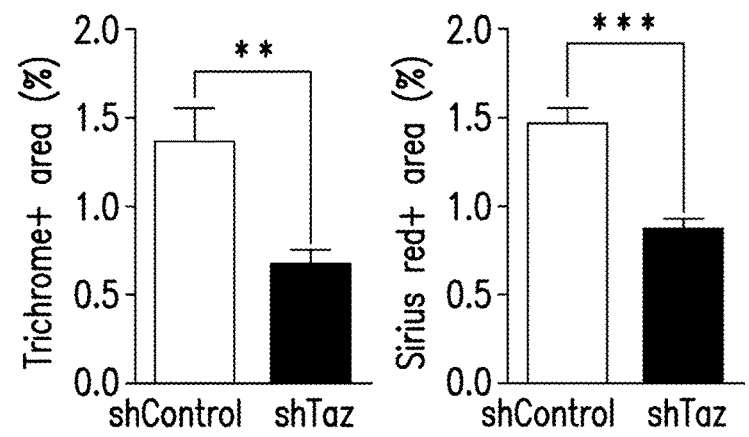
Figure 4E:
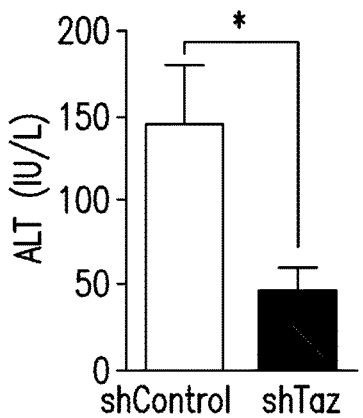
Figure 4F:
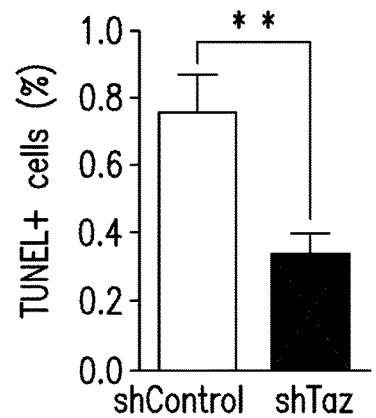
Figure 4G:
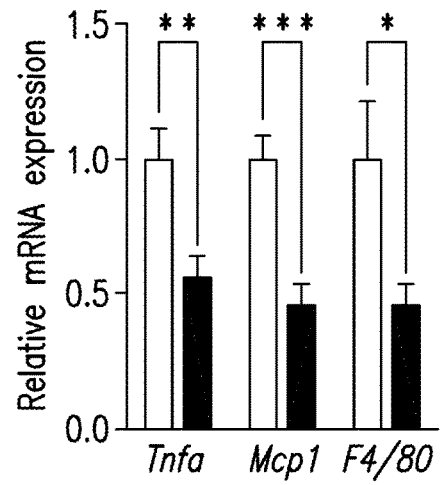
Figure 4H:
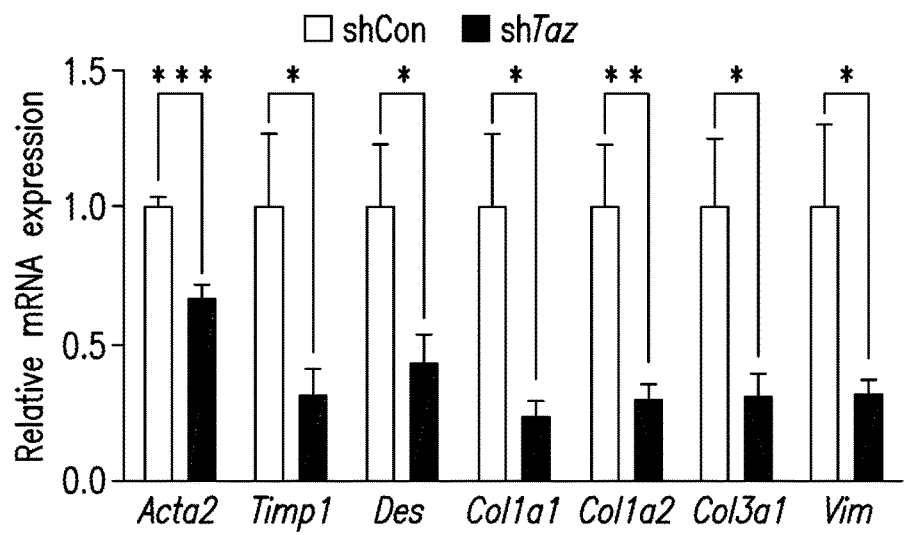
Figure 4I:
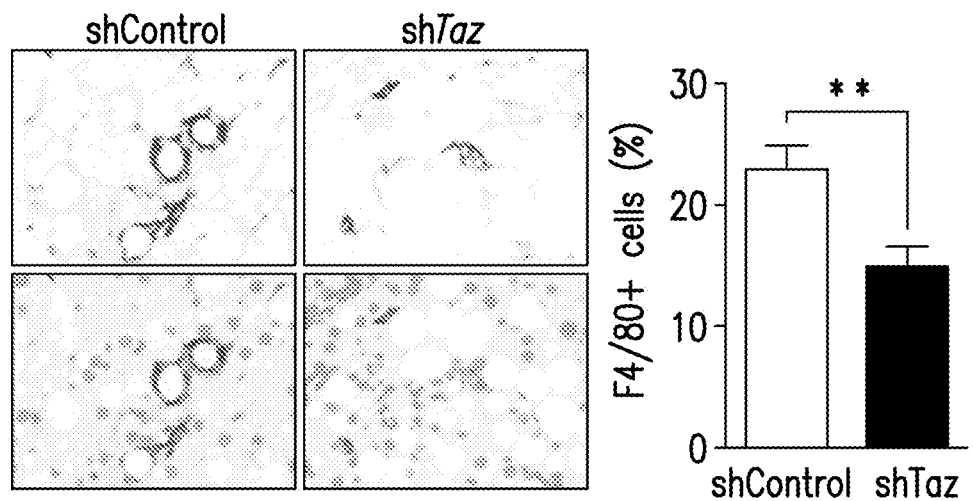
Figure 4J:
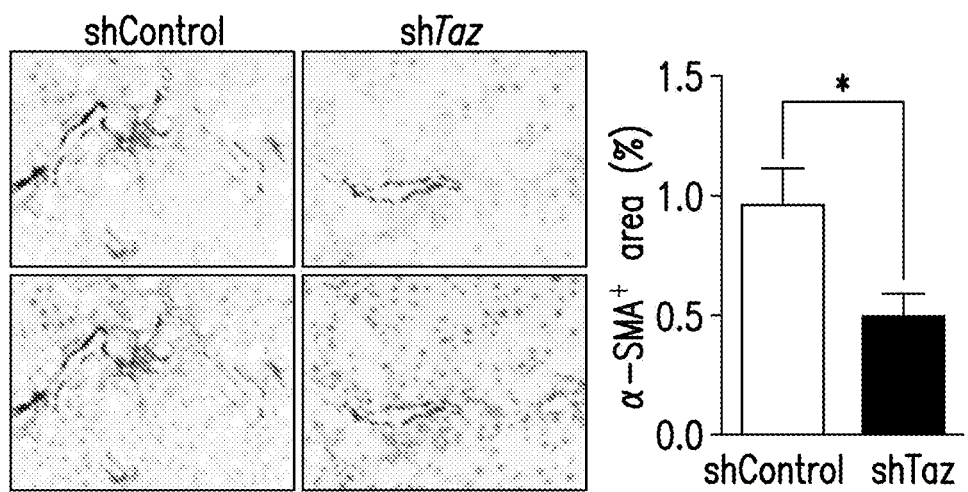
Figure 5A:
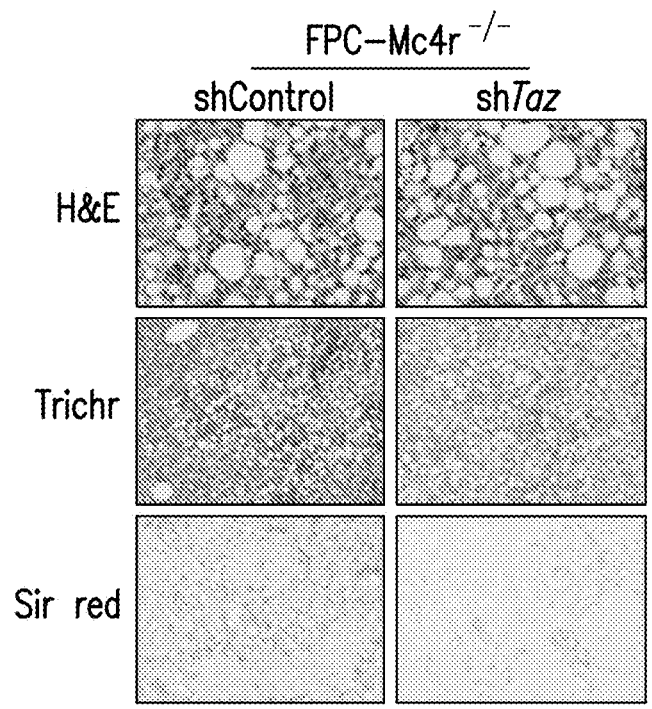
FIGS. 5A-H are immunohistochemistry stains and graphic quantifications illustrating that TAZ Silencing Reduces Liver Inflammation and Fibrosis in FPC-Fed Mc4r-/- Hyperphagic Mice. The following parameters were measured in male Mc4r-/- mice treated with AAV8-shTaz or control vector and then fed the FPC diet for 16 weeks ($*p<0.05$, $p<0.01$, $*p<0.0001$, mean±SEM; n=5 mice/group)
Figure 5B:
Figure 5C:
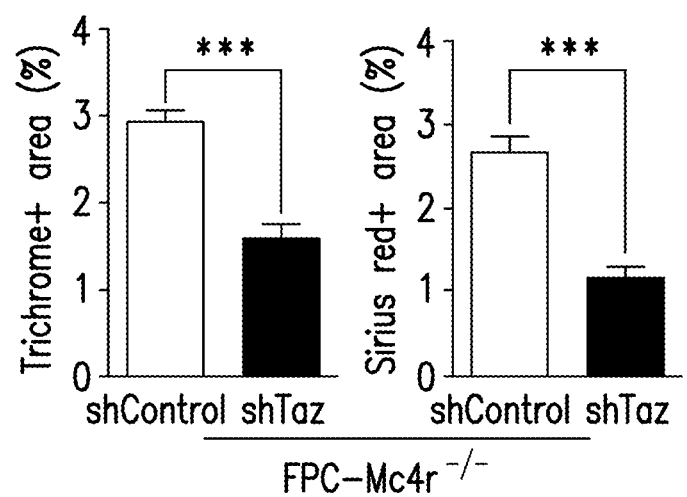
Figure 5D:
Figure 5E:
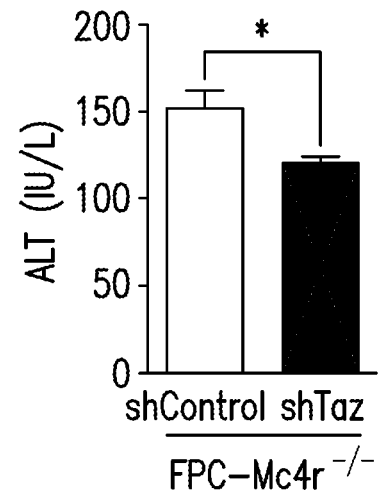
Figure 5F:
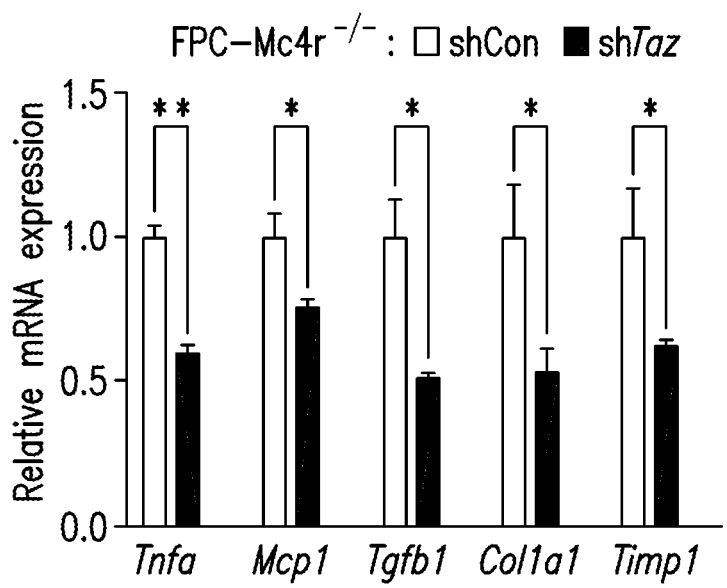
Figure 5G:
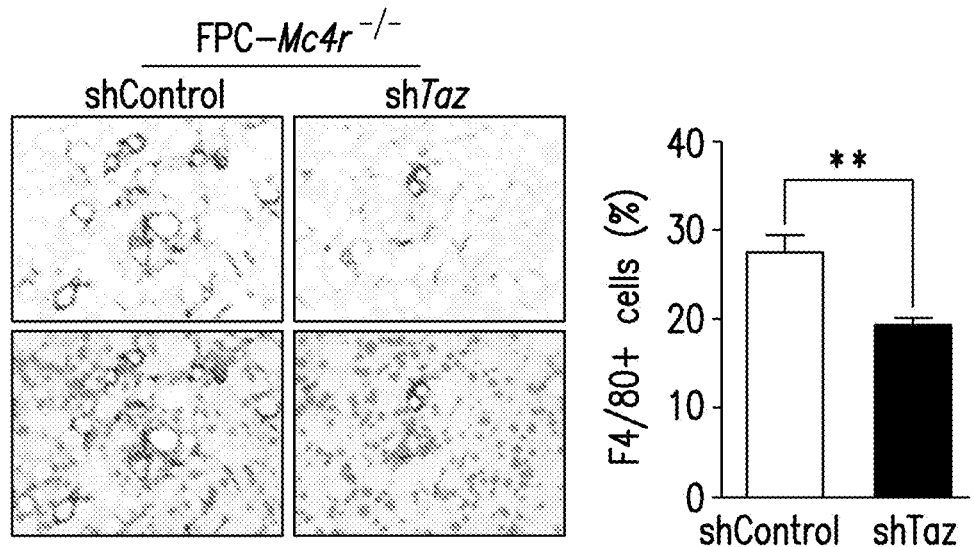
Figure 5H:
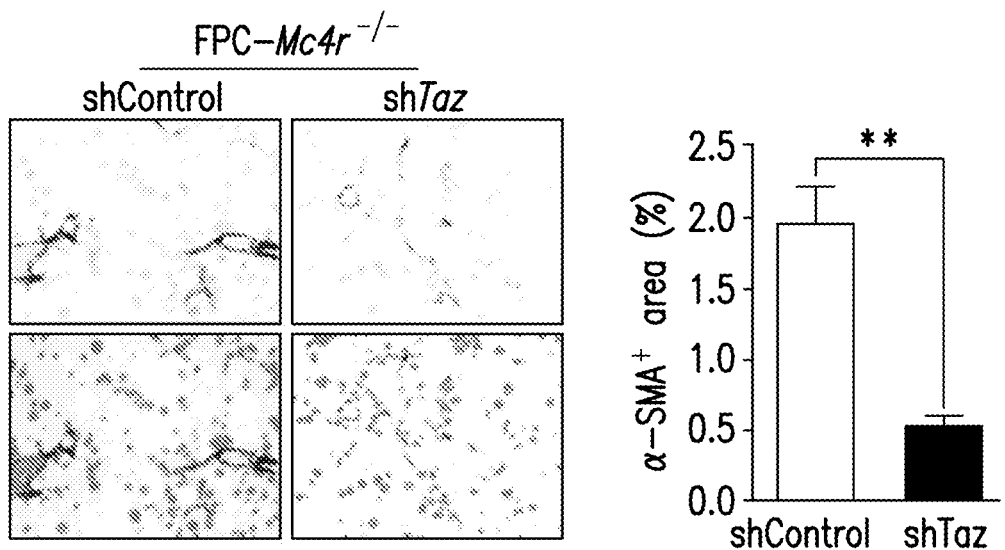

TAZ Silencing Reduces Liver Inflammation, Fibrosis, and Cell Death in Mouse Models of NASH To study TAZ function in NASH development, FPC mice were treated with AAV8-shTaz vs. AAV8-control RNA. AAV8-shTaz led to robust silencing of TAZ (FIG. 4A). Mouse body weight, liver:body weight ratio, fasting blood glucose, plasma insulin, and plasma cholesterol were similar in the Taz shRNA and control groups. Liver sections showed marked reductions in both inflammatory cell infiltration and fibrosis endpoints in the shTaz cohort (FIGS. 4B-D), while steatosis was not affected. Plasma ALT was decreased in shTaz-treated mice (FIG. 4E), and this was associated with a decrease in TUNEL+ and 4-HNE+ liver cells (FIG. 4F), indicating that Taz silencing reduced both cell death and oxidative stress in liver cells. At the mRNA level, Taz silencing caused a robust reduction in the expression of mRNAs related to hepatic inflammation—Tnfa, Mcp1, and F4/80 (Adgre1—and fibrosis (FIGS. 4G-H), including the NASH-relevant genes Acta2 (α-SMA), Timp1, Des, Col1a1, Col1a2, Col3a1, and Vim (Friedman, 2008; Younossi et al., 2011). These changes were accompanied by decreases in both F4/80+ macrophages and α-SMA+ cells (FIGS. 4I-J). A similar study was also conducted in which hyperphagic Mc4r$^{-/-}$ mice were fed the FPC diet for 16 wks. These mice develop more liver fibrosis compared with FPC-fed WT C57BL/6J mice, and silencing of Taz in the liver of these mice resulted in decreased staining for aniline blue, Sirius red, and α-SMA; lower hydroxyproline content; and decreased liver inflammation (FIGS. 5A-H).

Finally, these results were also confirmed in the MCD model, where shTaz decreased both hepatic inflammation and fibrosis without impacting steatosis and also reduced inflammatory and fibrotic gene expression, α-SMA+cells, and macrophages in the liver. Thus, in separate models of NASH, hepatic TAZ silencing improved key liver parameters related to inflammation, fibrosis, and cell death without affecting metabolic parameters or steatosis.

Figure 6A:
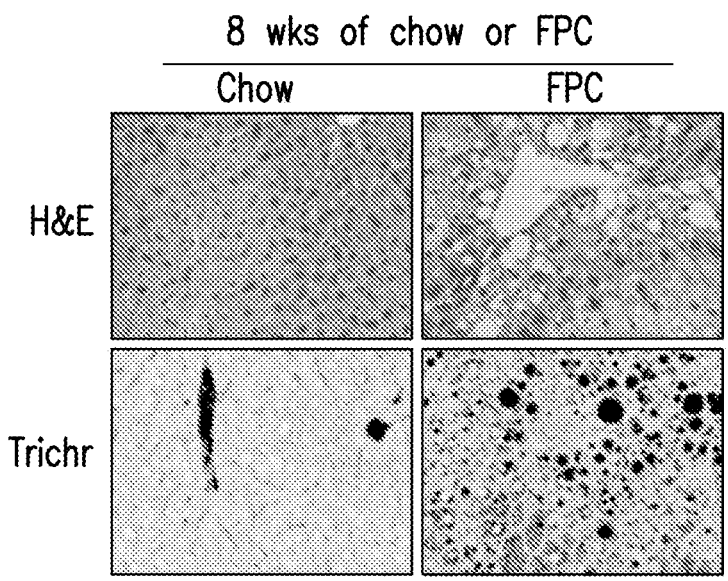
FIGS. 6A-H are immunohistochemistry stains and graphic quantifications illustrating that TAZ Silencing After the Development of Steatosis Reduces Liver Inflammation and Fibrosis in FPC-Fed Mice
Figure 6B:
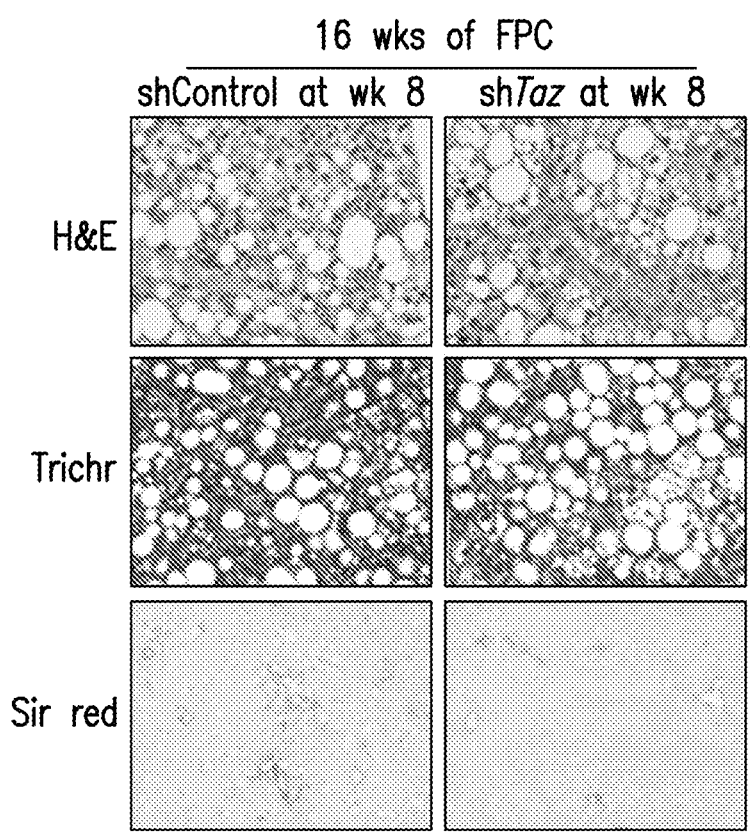
Figure 6C:
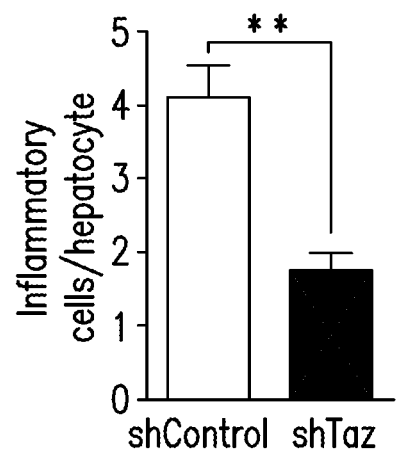
Figure 6D:
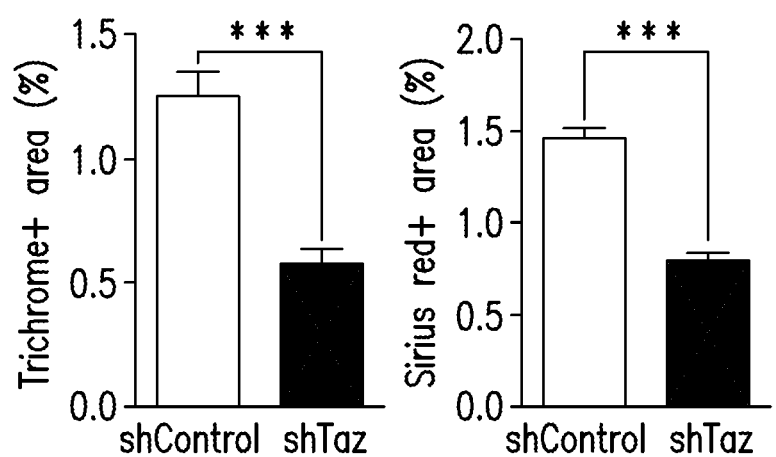
Figure 6E:
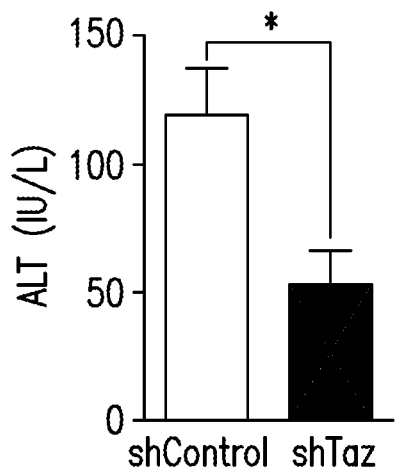
Figure 6F:
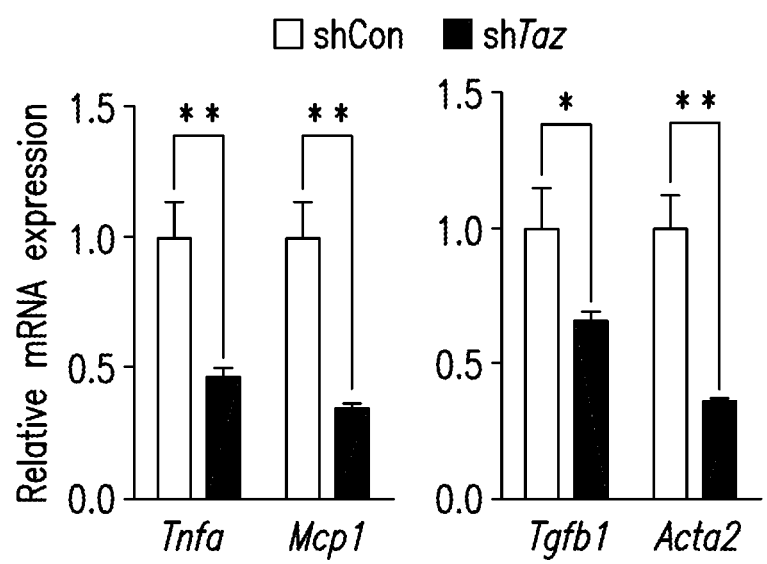
Figure 6G:
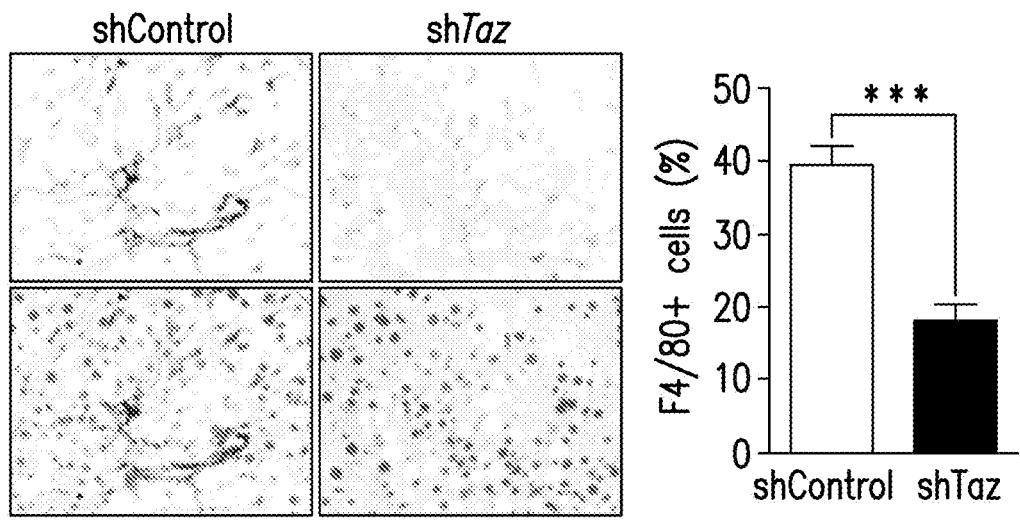
Figure 6H:
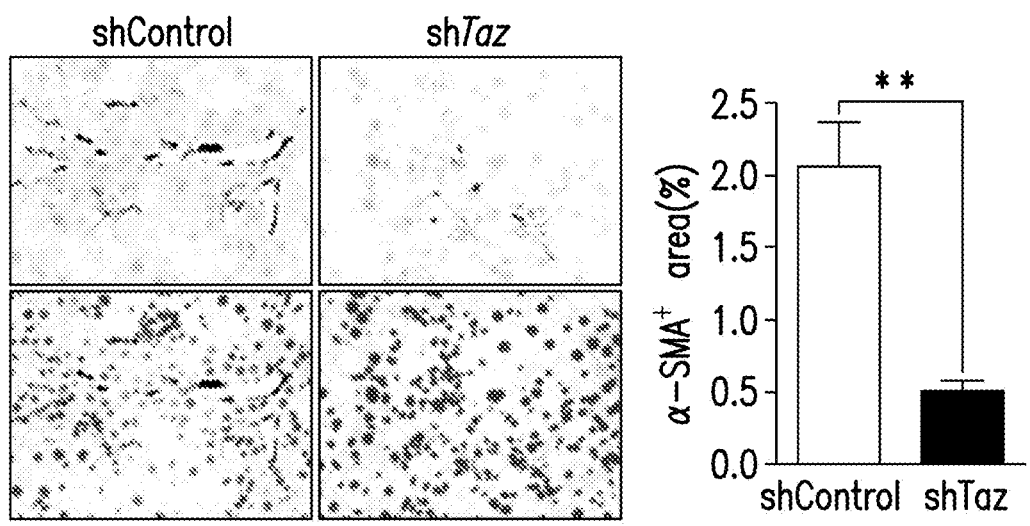

To investigate the role of TAZ specifically in steatosis-to-NASH conversion, mice were first fed the FPC diet for 8 weeks and then injected with AA8-shTaz or control virus, followed by an additional 8 weeks on the diet. Note that 8 weeks of FPC diet caused steatosis but no appreciable inflammation or fibrosis (FIG. 6A). The mice who received shTaz at week 8 showed marked reductions at 16 weeks in inflammatory cells, fibrosis endpoints, plasma ALT, inflammatory- and fibrosis-related genes, F4/80+ macrophages, and α-SMA+ cells, but not steatosis (FIGS. 6B-H). These data suggest that TAZ is particularly important in key processes that promote steatosis-to-NASH progression.

Hepatocyte TAZ Induces Indian Hedgehog, Which Promotes the Expression of Pro-Fibrotic Genes in Hepatic Stellate Cells Mechanisms linking TAZ to fibrosis progression were examined. HSCs, the main source of collagen-producing myofibroblasts in NASH-related fibrosis (Mederacke et al., 2013), can be activated by the hedgehog pathway (Syn et al., 2011). In this context, ChIP array data indicated that the gene encoding Indian hedgehog, Ihh, is a TAZ/TEAD target. The new hypothesis that increased TAZ in hepatocytes during NAFLD progression leads to the secretion of Ihh, which then acts on HSCs to promote the expression of pro-fibrotic genes was explored.

To begin, TAZ ChIP analysis of livers of chow-fed and FPC-fed mice with or without TAZ silencing was conducted, focusing on a TAZ/TEAD consensus sequence in intron 1 of murine Ihh that is conserved among species, including humans (Zanconato et al., 2015) (FIGS. 7A-B). The results show a significant increase in the ChIP signal in the livers of FPC-fed vs. chow-fed mice, which was dependent on anti-TAZ and was not seen when a non-consensus sequence was amplified. Most importantly, the ChIP signal in the livers of FPC mice was lowered to the chow level by TAZ silencing. Thus, TAZ interacts with a TAZ/TEAD consensus sequence in intron 1 of Ihh in the livers of FPC-fed mice.

Figure 7E:
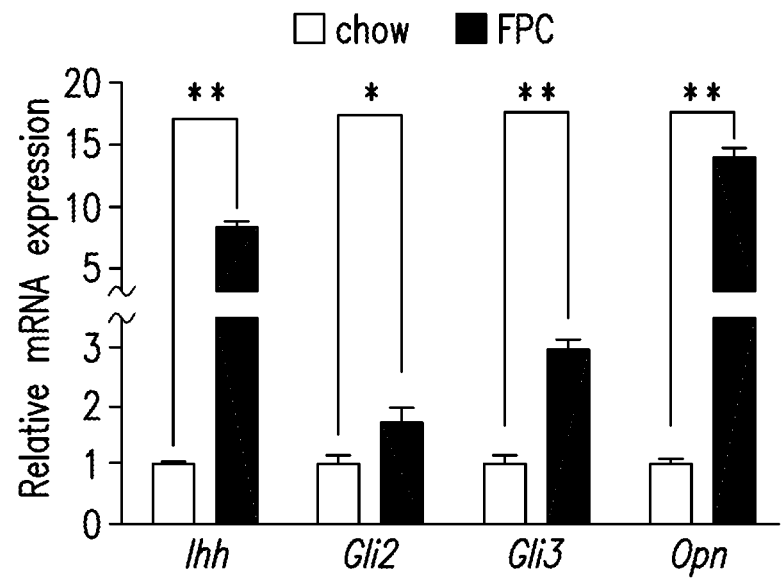
Figure 7F:
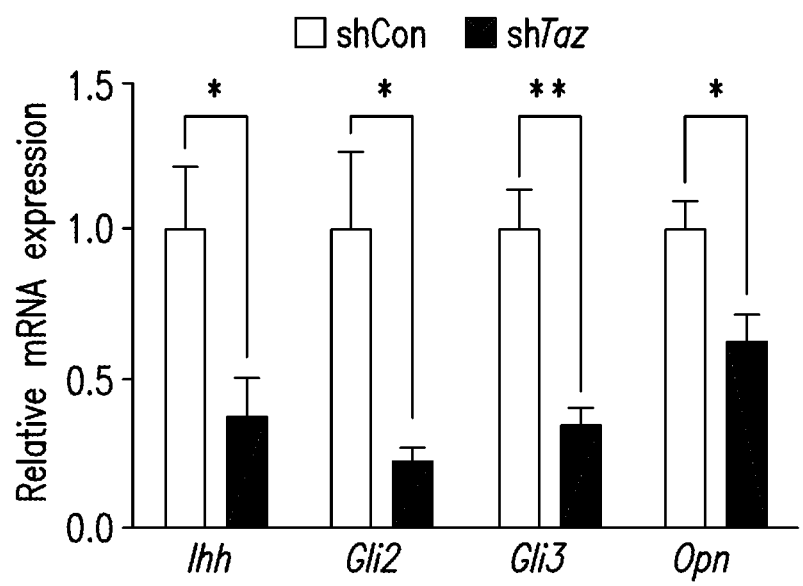
Figure 7G:
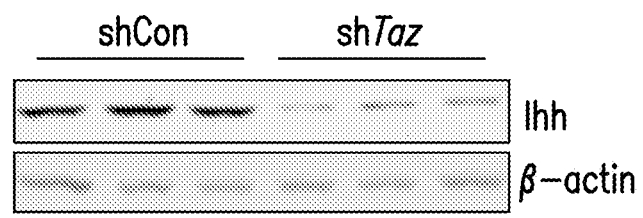
Figure 7H:
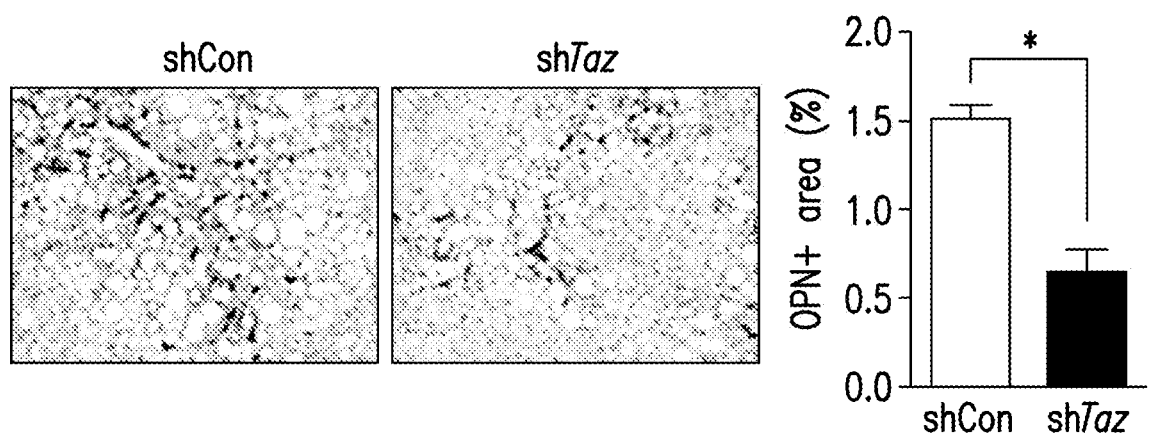

Next, whether human NASH liver expressed higher levels of Ihh compared with normal and steatotic liver was analyzed. As was the case with TAZ (above), the expression of Ihh was greater in the livers of subjects with NASH compared with normal and steatotic liver (FIG. 7C). Similarly, the livers of FPC-fed mice had markedly higher levels of Ihh compared with the livers of chow-fed mice (FIG. 7D). Next, the chow and FPC liver extracts were compared for gene expression of Ihh and the Ihh pathway downstream genes, Gli2 and Gli3. All three mRNAs were elevated in FPC liver, as was an Ihh target gene, osteopontin (Opn) (Razzaque et al., 2005), which is involved in HSC-induced fibrosis in NASH (Syn et al., 2011) (FIG. 7E). To explore causation with regard to TAZ, these assays were repeated in FPC-fed mice with or without TAZ silencing. All four mRNAs and Ihh protein were substantially lower in the TAZ-silenced mice (FIGS. 7F-G), as was OPN as assessed by immunohistochemistry (FIG. 7H). Thus, TAZ induces transcriptionally active Ihh during NASH progression in FPC-fed mice, and one of the targets of Ihh, Opn, has been linked to NASH fibrosis.

Figure 8A:
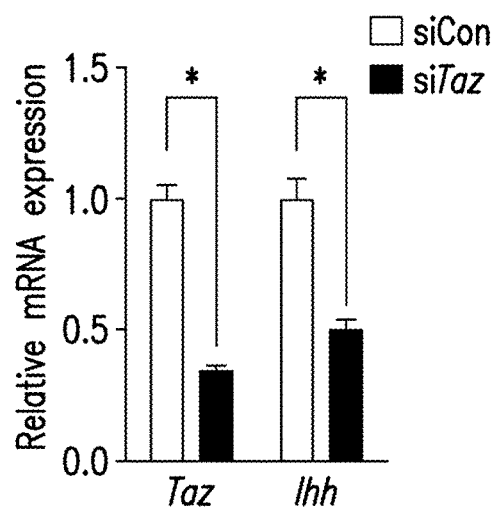
FIGS. 8A-G are immunohistochemistry stains, blots, and graphic quantifications illustrating that TAZ-Induced Hepatocyte Ihh Increases the Expression of Fibrosis-Related Genes in Hepatic Stellate Cells.
Figure 8B:
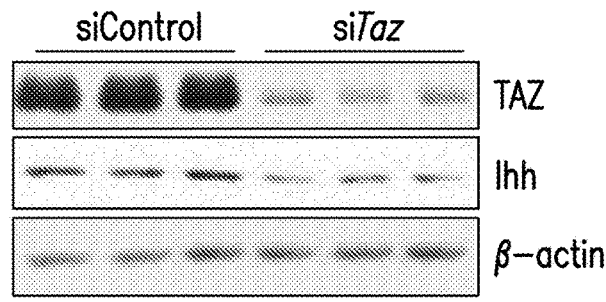
Figure 8C:
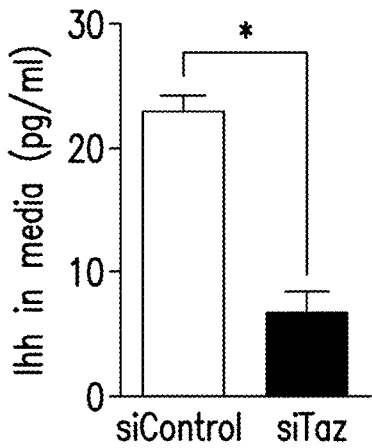
Figure 8D:
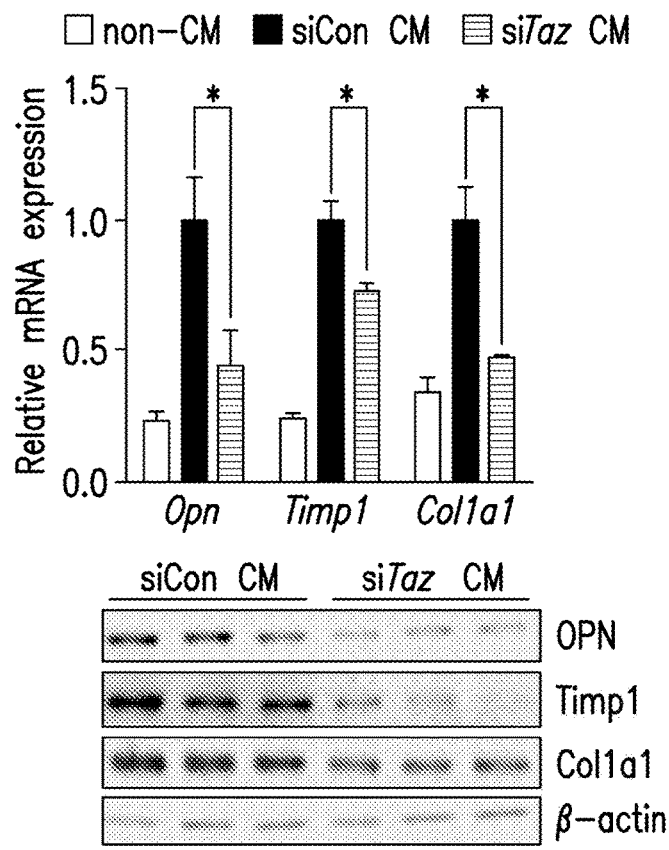
Figure 8E:
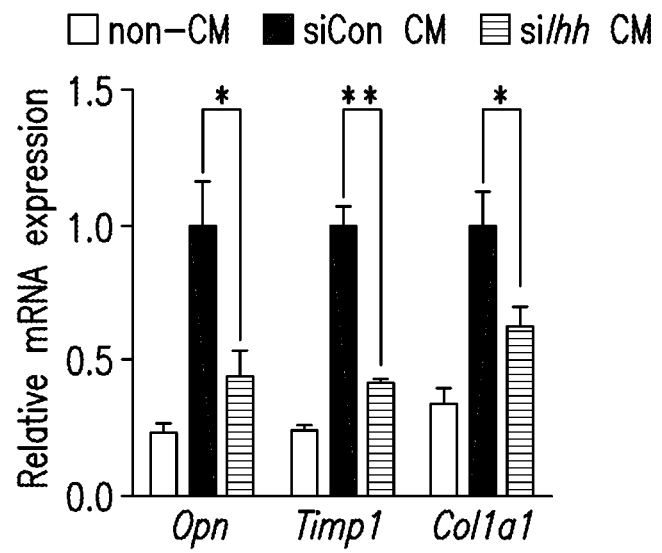
Figure 8F:
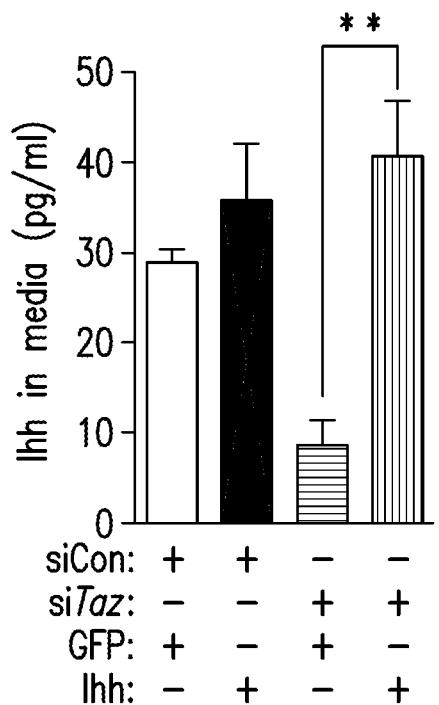
Figure 8G:
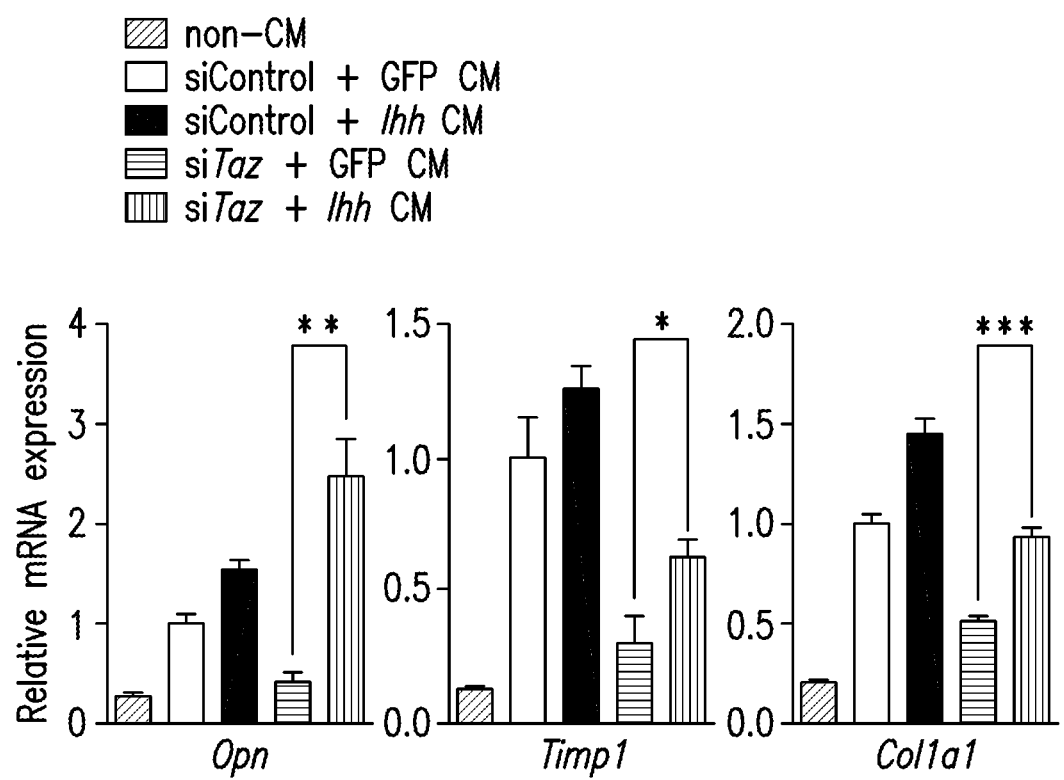
Figure 9:
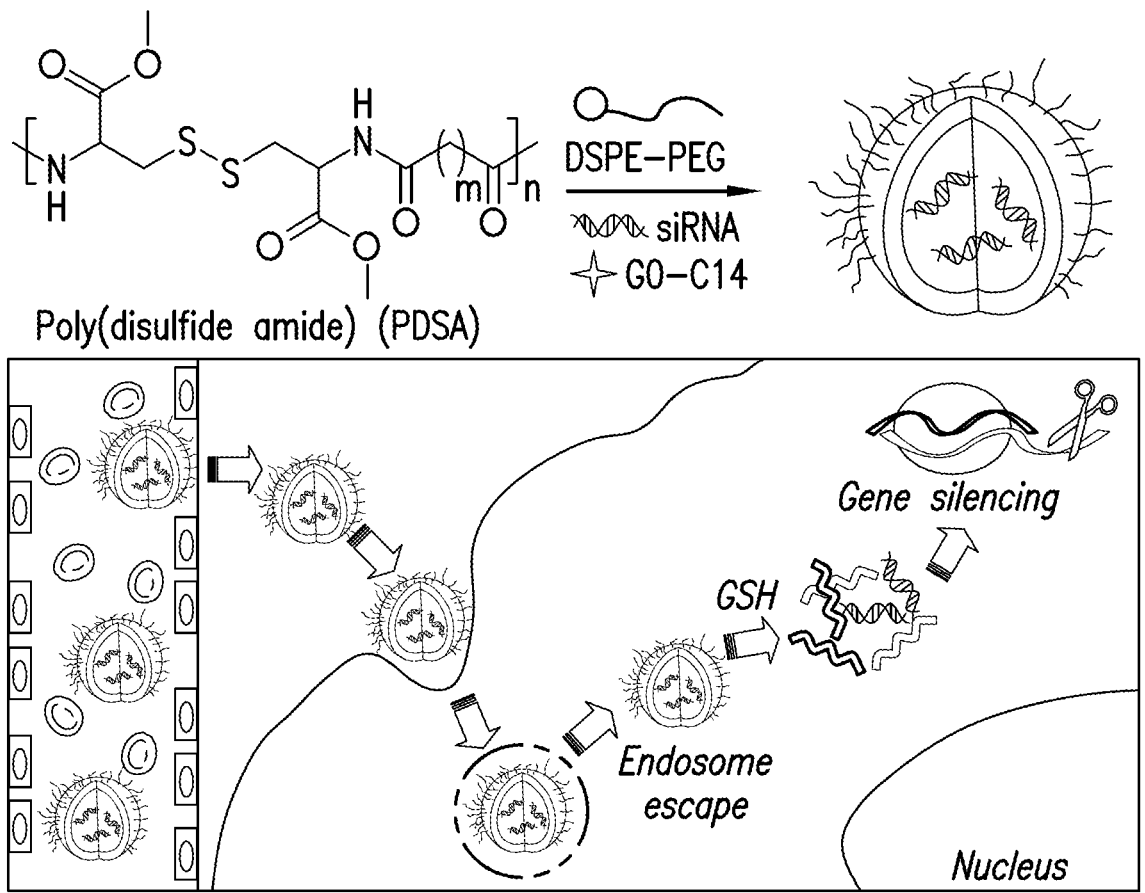
FIG. 9 is a schematic illustration of the redox-responsive NPs for systemic delivery siRNA to target liver genes involved in NASH.

To explore the possibility that TAZ-induced Ihh is secreted by hepatocytes and activates HSCs, an in vitro model using AML12 cells, a non-cancerous mouse hepatocyte cell line was utilized (Dumenco et al., 1995), along with primary murine HSCs. Consistent with the in vivo data, siTaz treatment of AML12 hepatocytes lowered cellular Ihh mRNA in the cells and Ihh protein in both the cells and media (FIGS. 8A-C). In the next experiments, conditioned medium (CM) from control or Taz-silenced AML12 cells was utilized, as well as medium not exposed to cells (non-CM), to primary murine hepatic stellate cells (HSCs). Compared with non-CM, hepatocyte CM markedly increased Opn mRNA as well as the mRNAs for two proteins involved in fibrosis, Timp1 and Col1a1. Most importantly, CM from TAZ-silenced hepatocytes lowered the levels these mRNAs and protein compared to CM from shCon-treated hepatocytes (FIG. 8D). Conditioned medium from Ihh-silenced hepatocytes also decreased the three mRNAs in HSCs (FIG. 8E), although the absolute degree of Timp1 lowering was somewhat greater in this experiment than in the siTaz experiment. Finally, to make a more direct link between TAZ-induced Ihh in hepatocytes and activation of HSCs, Ihh was restored in siTaz-treated hepatocytes by Ihh transfection and then analyzed to determine whether this lessened the suppressive effect of CM from these cells on the expression of the fibrosis-related genes in HSCs. Transfection of TAZ-silenced hepatocytes with Ihh led to a level of Ihh in the CM that was similar to that in the CM of control hepatocytes (FIG. 8F—compare 1st and 4th bars). As before, the CM of TAZ-silenced hepatocytes suppressed Opn, Timp1 and Col1a1 mRNA in HSCs (FIG. 8G—compare 2nd and 4th bars), and the present results illustrate that restoration of Ihh in these TAZ-silenced cells rescued CM-induced HSC gene expression (FIG. 8G—compare 4th and 5th bars). Together, these studies suggest that hepatocyte TAZ-induced Ihh promotes the expression of pro-fibrotic genes, thus linking TAZ-IHH to the progression from benign steatosis to NASH and the development of liver fibrosis, a key determinant of outcome in patients with NASH.

DISCUSSION

NASH, characterized by inflammation, cell death, and fibrosis can progress to advanced liver disease, cirrhosis, and the need for liver transplant. Steatosis alone is believed to be a little to no risk for progressive liver disease. Given the clinical significance of NASH compared to steatosis (Rinella, 2015), an important objective of research in this area is to identify factors and pathways that promote the conversion of steatosis to NASH and the development of fibrosis. The importance of this objective is underscored by the fact that NASH is becoming the leading cause of liver disease worldwide and yet lacks any definitive, evidence-based drug therapies approved by the US Food and Drug Administration (Rinella, 2015). In this context, the finding that TAZ plays a key role in steatosis-to NASH conversion and the development of fibrosis provides new insight into NASH and may suggest new targets for therapy.

Hepatic fibrosis is a key feature of NASH that distinguishes it from steatosis and determines long-term mortality in patients with NASH (Angulo et al., 2015). While both TAZ and YAP have been implicated in organ fibrosis in other settings, particularly in the lung with links to TGFα- SMAD signaling or induction of plasminogen activator inhibitor-1 (Liu et al., 2015; Mitani et al., 2009; Piersma et al., 2015; Saito and Nagase, 2015), there are only scattered reports about their roles in liver fibrosis, and none in the setting of NAFLD. For example, a recent study reported an association between microRNA-130/301, which can regulate TAZ and YAP, and carbon tetrachloride-induced liver fibrosis (Bertero et al., 2015), but there were no direct causation or mechanistic data related to the role of TAZ in this process. Another report showed that knockout of a pair of Hippo factors called Mps One Binder Kinase Activator (MOB)1A/1B in lean mice caused elevated TGFα-2/3 and liver fibrosis in a manner that was partially dependent on TAZ (Nishio et al., 2016).

Although the mechanism of TAZ in liver fibrosis in NASH is likely to be multifactorial, we provide evidence that the TAZ target Ihh may be important. Previous work has implicated hedgehog signaling in NASH fibrosis, particularly Shh signaling in HSCs (Bohinc and Diehl, 2012), both directly and via the induction of the pro-fibrotic cytokine IL-13 by immune cells (Shimamura et al., 2008; Syn et al., 2010). ChIP array data suggested that Ihh is a YAP/TAZ/TEAD target gene (Zhao et al., 2008), and using ChIP analysis of liver from FPC-fed mice, the present data illustrate for the first time that TAZ interacts with a highly conserved TAZ/TEAD consensus sequence in intron I of the Taz gene. Most importantly, hepatic Ihh was induced by the FPC diet and suppressed by shTaz. Moreover, the presently described in vitro study illustrated that hepatocyte TAZ-induced IHH activates a fibrosis program in HSCs. Further support for this aspect will benefit from additional mechanistic and in vivo causation studies, with the realization that the development of fibrosis during NASH progression is complex and multi-factorial and that TAZ likely has actions in addition to inducing Ihh that contribute to NASH fibrosis.

Two other important features of NASH, inflammation and cell death, were also ameliorated by TAZ silencing as shown in the present results. Little is known about the pro-inflammatory roles of TAZ, and, in general, YAP and TAZ inhibit rather than promote apoptosis during development and in cancer (Yu et al., 2015). However, there is one report showing that siTaz decreased TNFα-induced apoptosis in salivary gland epithelial cells (Hwang et al., 2014). RIP3-mediated necroptosis may also be important in hepatocyte death in NASH (Gautheron et al., 2014), and therefore it is possible that TAZ promotes this pathway. Given the various consequences of cell necrosis, this action of TAZ could contribute to inflammation and fibrosis as well as cell death in NASH (Chan et al., 2015; Luedde et al., 2014).

While the present studies focused on TAZ in hepatocytes, it is also known that YAP is significantly increased in progenitor-like reactive-appearing ductular cells (RDCs) in human and mouse NASH liver (Machado et al., 2015a). We have also found increased YAP in the livers of FPC mice, and most of the YAP-positive cells did not co-localize with HNF4α-positive hepatocytes. While the role of YAP in NASH remains to be elucidated, there are correlations among YAP+RDCs, fibrosis, accumulation of myofibroblasts, and expression of Shh and Opn. Of note, silencing TAZ in the livers of FPC mice did not affect YAP expression. It is expected that inhibiting YAP or any one or more of the YAP co-factors TEAD1-4 may also provide useful therapeutic effects in the context of inhibiting, preventing, or treating NASH and NASH related conditions.

The majority of the present experiments were conducted in a mouse model of insulin resistance and NAFLD that was a modification of previously described models (Charlton et al., 2011; Kohli et al., 2010). The NAFLD diet was based on human dietary risk factors for NASH, and the key improvement over previous models was the development of a high level of inflammation, hepatocyte death, and fibrosis in 16 weeks without the need for genetically engineered mutations and in the background of weight gain and insulin resistance. Whereas the fructose component of the diet likely contributes to steatosis (Abdelmalek et al., 2010; Ishimoto et al., 2013), the cholesterol and palmitic acid components may be important in NASH progression and perhaps TAZ induction. For example, the accumulation of unesterified cholesterol in the liver has been implicated in the development of NASH in humans (Ioannou, 2016) and in various mouse models (Subramanian et al., 2011; Van Rooyen et al., 2011; Wouters et al., 2008). The mechanisms(s) linking cholesterol to NASH are likely to be multifactorial. For example, studies using mice fed high-cholesterol diets have suggested that cholesterol can directly activate HSCs by inducing TLR4, promote oxidative stress and cell death in hepatocytes via excess mitochondrial cholesterol, and promote inflammation in Kupffer cells through lysosomal cholesterol enrichment (Bieghs et al., 2013; Rawson, 2006; Teratani et al., 2012). How cholesterol links to the TAZ pathway described in this report will be an important topic of future investigation. Likewise, palmitic acid has been reported to induce pro-inflammatory cytokine production by hepatocytes and Kupffer cells during NASH (Joshi-Barve et al., 2007; Miura et al., 2013), but other mechanisms may be involved as well. Thus, we would expect that lowering palmitic acid and/or lowering or decreasing unesterified cholesterol in the liver would have a beneficial effect on NASH and could be utilized in combination with any of the methods described herein. Finally, these studies illustrated that lowering the normally very high levels of vitamin E in previous murine diets, improved the model with respect to duplicating the human. NASH features, in line with the modest protective effects of vitamin E in human NASH.

In summary, the present data shows that the Hippo pathway transcription factor TAZ is elevated in the livers of humans with NASH, which is recapitulated in mouse models. In these models, silencing of TAZ suppresses key features of NASH progression but not steatosis. These data provide new insight into the pathophysiology of NASH and raise the prospect of liver-directed TAZ inhibition as a new therapeutic strategy to prevent NASH progression.

EXPERIMENTAL PROCEDURES

Reagents and Antibodies

The following antibodies were used for immunoblots: GAPDH (#3683), β-actin (#5125), CHOP (#5554), TAZ (#8418), p-eIF2α (#3398), eIF2α (#5324), Lamin A/C (#4777) from Cell Signaling; p-TAZ (sc-17610) and Col1a1 (sc-8784) from Santa Cruz; Ihh (ab39634) from Abcam; and Timp1 (AF980) from R & D. The following antibodies were using for immunostaining of liver: α-SMA (ACTA2) (C6198, F3777) and TAZ (HPA007415) from Sigma; F4/80 (MCA497GA) from AbD Serotec; Ly6g (#127601) from Biolegend; Ly6b (MCA771G) from Bio-Rad; OPN (AF808) from R & D; 4-hydroxynonenal (4-HNE) (AB5605) from Millipore; and HNF4α (sc-6556) from. Santa Cruz. The following plasma assay kits were used in this study: insulin ELISA (#90080) from. Crystal Chem; MCP1 ELISA (#88-7391-22) from eBiosciences; cholesterol (#439-17501) and triglyceride (#465-09791, #461-09891) from Wako; and ALT (#006A-CR) and AST (#004A-CR) from BQ Kits, Inc. AAV8-shRNA targeting murine Taz was made by annealing complementary oligonucleotides (5'-CAC-CAcagccgaatctcgcaatgaatCTCGAGATTCATTGCGAG ATTCGGCTG-3') (SEQ ID NO:1), which were then ligated into the pAAV-RSV-GFP-H1 vector, as described previously (Lisowski et al., 2014). The resultant constructs were amplified by the Salk Institute Gene Transfer, Targeting, and Therapeutics Core.

Animal Studies

Male wild-type mice C57BL/6J (#000664, 8-10 weeks/old) and MC4R-negative loxTB Mc4r mice (#006414, 6 weeks/old), referred to here as Mc4r$^{-/-}$ mice, were obtained from Jackson Laboratory (Bar Harbor, ME) and were allowed to adapt to housing in the Columbia University Medical Center Institute of Comparative Medicine for 1 week prior to random assignment to experimental cohorts. The mice were then fed the following diets for the times indicated in the figure legends: (a) chow diet (Picolab rodent diet 20, #5053); (b) "fast-food" (FF). diet (TestDiet 1810060): high-fat diet with drinking water containing 42 g/L glucose and fructose (55%/45%, w/w); or (c) fructose-palmitate-cholesterol ("FPC") diet (Teklad, TD.140154): similar to FF diet but with 1.25% added cholesterol and with palmitic acid, anhydrous milk fat, and Primex as the sources of fat and with a ~60% decrease in vitamin E and a ~35% decrease in choline compared with typical mouse diets. The detailed composition of these diets appear in Tables 1 and 2. For several experiments, groups of mice were placed on a methionine-choline-deficient diet (Teklad, TD. 90262) for 8 weeks, as described (Dixon et al., 2012). Adeno-associated virus ($2\times10^{11}$ genome copy/mouse) was delivered by tail vein injection either 1 week prior to diet initiation or after 8 weeks of the FPC diet. Animals were housed in standard cages at 22° C. in a 12-12-h light-dark cycle. All animal experiments were performed in accordance with institutional guidelines and regulations and approved by the Institutional Animal Care and Use Committee at Columbia University.

Human Samples

Liver biopsy specimens from individuals undergoing weight loss surgery were selected from the MGH NAFLD Biorepository. Patients gave informed consent at the time of recruitment, and their records were anonymized and de-identified. Studies were approved by the Partners Human Research Committee (IRB) and conducted in accordance with National Institutes of Health and institutional guidelines for human subject research. Additional anonymized and de-identified liver biopsy sections were obtained from Dr. Jay Lefkowitch, Columbia University Medical Center. Cases with NAFLD activity score (NAS) of 1-3 were classified as early NAFLD (no fibrosis), while cases with NAS>5 and fibrosis stage 1a/b-4 were classified as NASH. Cases with steatosis score>1 and inflammation and ballooning scores of 0 and no fibrosis were classified as steatosis. Cases with NAS 0 were classified as normal.

Blood and Plasma Analyses

Fasting blood glucose was measured using a glucose meter (One Touch Ultra, Life-scan) in mice that were fasted for 4-5 h, with free access to water. Complete blood counts were obtained with the FORCYTE Veterinary Hematology Analyzer (Oxford Science, Inc.). Total plasma triglyceride and cholesterol were assayed using a commercially available kit from Wako. For insulin, MCP1, AST, ALT, TC, TG are measured following kit instruction by using plasma.

Histopathological Analysis, Immunohistochemistry, and Immunofluorescence Microscopy Formalin-fixed, paraffin-embedded liver sections were stained with hematoxylin and eosin (H&E) and evaluated for severity of NAFLD by a trained hepatopathologist blinded to the clinical diagnosis, αaccording to criteria described by Brunt et al. (Kleiner et al., 2005; Liang et al., 2014). Liver fibrosis was assessed by Picrosirius (Sirius) red (Polysciences, #24901) or by Masson's trichrome staining (Sigma, HT15), with aniline blue-positive areas quantified as a measure of collagen content in the trichrome-stained. sections. TUNEL staining was conducted using a kit from Roche (#12156792910). For immunofluorescence microscsopy, paraffin sections were rehydrated, subjected to antigen retrieval by placing in a pressure cooker for 10 mins in Target Retrieval Solution (Dako, S1699), and then blocked with serum. Sections were labeled with primary antibodies overnight, using a 1:150 dilution except for α-SMA and 4-HNE (1:200) and TAZ (1:400), followed by incubation with a fluorophore-conjugated secondary antibody for 1 h. The stained sections were mounted with DAPI-containing mounting medium (Life Technologies, P36935) and then viewed on an Olympus IX 70 fluorescence microscope. For filipin (Sigma, F9765) staining, frozen sections were fixed in 4% paraformaldehyde for 1 h at room temperature, then rinsed using glycine/PBS and stained 0.25 mg/ml filipin 2 h at room temperature. Fluorescence microscopic images were analyzed using ImageJ software. For immunohistochemistry, the deparaffinization, rehydration, and antigen retrieval processes were the same as with immunofluorescence staining. The slides were treated with 3% hydrogen peroxide for 10 min and then blocked with Serum-Free Protein Block (Dako, X0909) for 30 min. Sections were incubated with OPN, F4/80, or α-SMA primary antibody (1:100) overnight and then developed using DAB substrate kit (Cell Signaling, #8059) for OPN and F4/80, FITC-labeled anti-HRP secondary antibody for α-SMA.

Measurement and Analysis of Liver Tissue Fatty Acids and Cholesterol

Liver specimens (~20 mg) were homogenized in 600 μl of 5% ethanol, and then 6 μl was added to 100 μl KOH (1M, 9:1 methanol:$H_2O$). The suspension was heated at 100° C. for 30 min and then clarified by centrifugation, followed by addition of 80 μl HCl to the supernate. Fatty acids in this solution were identified and quantified by gas chromatography in the Columbia Biomarker Core Laboratory. For liver cholesterol quantification, liver tissue was homogenized in $H_2O$. Color Reagent Solution from the Wako Total Cholesterol assay kit was added at a 1:20 ratio (v/v) to the liver lysates. The suspension was then centrifuged, and the supernates were read in a plate reader.

Immunoblotting

Liver protein was extracted using RIPA buffer (Thermo, #89900), and the protein concentration was measured by a BCA assay (Thermo, #23227). Proteins were separated by electrophoresis on 4-20% Tris gels (Life technologies, EC60285) and transferred to a nitrocellulose membranes (Bio-Rad, #1620115). The membranes were blocked for 30 min at room temperature in Tris-buffered saline and 0.1% Tween 20 (TBST) containing 5% (wt/vol) nonfat milk and then incubated with primary antibody in the same buffer at 4° C. overnight, using 1:1000 dilution except for CHOP and Ihh (1:3000). The protein bands were detected with horse radish peroxidase-conjugated secondary antibodies (Cell Signaling) and Supersignal West Pico enhanced chemiluminescent solution (Thermo, #34080). Cultured cells were lysed in Laemmli sample buffer (Bio-Rad, #161-0737) containing 5% 2-mercaptoethanol, heated at 100° C. for 5 min, and then electrophoresed and immunoblotted as above. Preparation of nuclear and cytoplasmic fractions of liver was carried out using Nuclear Extract Kit (Active Motif, #40010) according to the manufacturer's protocol.

Cell Culture

AML12 mouse hepatocytes were purchased from ATCC (CRL-2254) and cultured in DMEM/F12 medium (Lifetechnologies, #11320) with 10% FBS (Gibco, #16140-071). Hepatic stellate cells (HSCs) were isolated from 5-6 mo/o BALB/C mice as described previously (Mederacke et al., 2015). Briefly, after cannulation of the inferior vena cava, the portal vein was cut, allowing retrograde step-wise perfusion with solutions containing protease (Sigma Aldrich, P5147) and collagenase D (Roche, #11088866001). The perfusates were subjected to 9.7% Nycodenz (Accurate Chemical, #1002424) gradient centrifugation to isolate the HSCs, which were then plated in tissue culture dishes and used the next day. For conditioned medium transfer experiments, AML12 cells were cultured in DMEM containing 0.2% BSA and incubated for 24 h. The media were then transferred to HSCs that had previously been incubated in DMEM, 0.2% BSA for 24 h. After 72 h, the HSCs were assayed for gene expression. For quantification of Ihh, hepatocyte conditioned medium was concentrated 10-fold by centrifugal filters (Millipore, Ultracel) and analyzed by an ELISA kit (LifeSpan Biosciences, F7953).

Quantitative RT-qPCR

Total RNA was extracted from liver tissue or primary cultured hepatocytes using the RNeasy kit (Qiagen, 74106). cDNA was synthesized from 1 μg total RNA using oligo (dT) and Superscript H (Invitrogen). qPCR was performed in an 7500 Real time PCR system (Applied Biosystems) using SYBR green chemistry (Life Technologies, #4367659). The primer sequences are listed in Table 4.

siRNA-Mediated Gene Silencing and Transfection siRNA sequences against mouse Taz and scrambled RNA were purchased from IDT; the target sequence of Taz siRNA was ACA UGG ACG AGA UGG AUA CAG GUG A (SEQ ID NO:2). The scrambled RNA and siRNA were transfected into AML12 cells (ATCC) using RNAiMAX (Life Technologies, #13778150) according to the manufacturer's instruction. A plasmid encoding GFP was purchased from Lonza (pmaxGFP), and a plasmid encoding murine Ihh was purchased from Origene (MR227435). The plasmids were transfected into AML12 cells using Lipofectamine® LTX Reagent with PLUS™ Reagent (Life Technologies, #15338100).

Mouse Liver Nuclei Preparation and ChIP Assays

Mouse liver tissues were homogenized using a Dounce homogenizer (Wheaton, #357544) with a loose pestle in 1:10 (w:v) of ice-cold NP-40 lysis buffer supplemented with a protease inhibitor cocktail. The release of nuclei from the homogenate was monitored by DAPI staining and fluorescence microscopy. To purify intact nuclei, lysates were layered over a step gradient consisting of 1 M and 0.68 M sucrose and then centrifuged at 4000 rpm for 30 min at 4° C. Following a washing step, nuclear pellets were cross-linked with 1% fresh formaldehyde in PBS for 10 min at room temperature. Cross-linking was terminated by addition of 200 mM Tris-HCl (pH 9.4) and 1 mM DTT, and after 10 mins the suspension was centrifuged at 2500 rpm for 15 min at 4° C. Nuclear pellets were suspended in SDS lysis buffer containing protease inhibitors, incubated for 10 min on ice. DNA was sheared in a cold water bath using a focused-ultrasonicator (Covaris, S2) to obtain DNA fragments with an average size of 500 bps. Fragmented chromatin was pre-cleaned by incubating with normal rabbit IgG (Santa Cruz, sc-2027) for 1 h at 4 ° C., followed by 1 h of incubation with 50 μL protein G magnetic beads (Pierce, #88847) at 4 ° C. with rotation. Immunoprecipitation was conducted using a rabbit anti-TAZ antibody (Cell Signaling, #4883), and a control rabbit anti-HA antibody (Santa Cruz, sc-805) was used as a negative control. Immunoprecipitated chromatin fragments were reverse cross-linked, digested by proteinase K, and purified using QIAquick PCR Purification Kit (Qiagen, #28106). The presence of TAZ in Ihh intronic region was quantified by qPCR and expressed relative to the input genomic DNA. The sequences of primers used for the ChIP-qPCR assays, including negative control primers, are described in Table 5.

TABLE 5

Primers used for qPCR.

| Primers | Sequences |
|---|---|
| Hprt F | TCAGTCAACGGGGACATAAA (SEQ ID NO: 3) |
| Hprt R | GGGGCTGTACTGCTTAACCAG (SEQ ID NO: 4) |
| Taz (Wwtr1) F | CATGGCGGAAAAAGATCCTCC (SEQ ID NO: 5) |
| Taz (Wwtr1) R | GTCGGTCACGTCATAGGACTG (SEQ ID NO: 6) |
| Tgfb1 F | CTCCCGTGGCTTCTAGTGC (SEQ ID NO: 7) |
| Tgfb1 R | GCCTTAGTTTGGACAGGATCTG (SEQ ID NO: 8) |
| Acta2 F | ATGCTCCCAGGGCTGTTTTCCCAT (SEQ ID NO: 9) |
| Acta2 R | GTGGTGCCAGATCTTTTCCATGTCG (SEQ ID NO: 10) |
| Vim F | TTTCTCTGCCTCTGCCAAC (SEQ ID NO: 11) |
| Vim R | TCTCATTGATCACCTGTCCATC (SEQ ID NO: 12) |
| Des F | CTAAAGGATGAGATGGCCCG (SEQ ID NO: 13) |
| Des R | GAAGGTCTGGATAGGAAGGTTG (SEQ ID NO: 14) |
| Col1a1 F | GCTCCTCTTAGGGGCCACT (SEQ ID NO: 15) |
| Col1a1 R | CCACGTCTCACCATTGGGG (SEQ ID NO: 16) |
| Col1a2 F | GTAACTTCGTGCCTAGCAACA (SEQ ID NO: 17) |
| Col1a2 R | CCTTTGTCAGAATACTGAGCAGC (SEQ ID NO: 18) |
| Col3a1 F | CTGTAACATGGAAACTGGGGAAA (SEQ ID NO: 19) |
| Col3a1 R | CCATAGCTGAACTGAAAACCACC (SEQ ID NO: 20) |
| F4/80 (Adgre1) F | ACCACAATACCTACATGCACC (SEQ ID NO: 21) |
| F4/80 (Adgre1) R | AAGCAGGCGAGGAAAAGATAG (SEQ ID NO: 22) |
| Tnfa F | CTTCTGTCTACTGAACTTCGGG (SEQ ID NO: 23) |
| Tnfa R | CAGGCTTGTCACTCGAATTTTG (SEQ ID NO: 24) |
| Mcp1 F | TTAAAAACCTGGATCGGAACCAA (SEQ ID NO: 25) |
| Mcp1 R | GCATTAGCTTCAGATTTACGGGT (SEQ ID NO: 26) |
| Ihh F | CTCTTGCCTACAAGCAGTTCA (SEQ ID NO: 27) |
| Ihh R | CCGTGTTCTCCTCGTCCTT (SEQ ID NO: 28) |
| Gli2 F | CAACGCCTACTCTCCCAGAC (SEQ ID NO: 29) |
| Gli2 R | GAGCCTTGATGTACTGTACCAC (SEQ ID NO: 30) |
| Gli3 F | CACAGCTCTACGGCGACTG (SEQ ID NO: 31) |
| Gli3 R | CTGCATAGTGATTGCGTTTCTTC (SEQ ID NO: 32) |
| Opn F | CTGACCCATCTCAGAAGCAGAATCT (SEQ ID NO: 33) |
| Opn R | TCCATGTGGTCATGGCTTTCATTGG (SEQ ID NO: 34) |
| Timp1 F | CTCAAAGACCTATAGTGCTGGC (SEQ ID NO: 35) |
| Timp1 R | CAAAGTGACGGCTCTGGTAG (SEQ ID NO: 36) |
| Cpt1b F | GCACACCAGGCAGTAGCTTT (SEQ ID NO: 37) |
| Cpt1b R | CAGGAGTTGATTCCAGACAGGTA (SEQ ID NO: 38) |
| Pparg F | TCGCTGATGCACTGCCTATG (SEQ ID NO: 39) |
| Pparg R | GAGAGGTCCACAGAGCTGATT (SEQ ID NO: 40) |
| Scd1 F | CTGACCTGAAAGCCGAGAAG (SEQ ID NO: 41) |
| Scd1 R | AGAAGGTGCTAACGAACAGG (SEQ ID NO: 42) |
| Fasn F | AAGTCCCAGAAATCGCCTATG (SEQ ID NO: 43) |
| Fasn R | GGTATGGTTTCACGACTGGAG (SEQ ID NO: 44) |
| Acaca F | ATGGGCGGAATGGTCTCTTTC (SEQ ID NO: 45) |
| Acaca R | TGGGGACCTTGTCTTCATCAT (SEQ ID NO: 46) |
| Cd3 F | ATGCGGTGGAACACTTTCTGG (SEQ ID NO: 47) |
| Cd3 R | GCACGTCAACTCTACACTGGT (SEQ ID NO: 48) |
| Cd20 F | AACCTGCTCCAAAAGTGAACC (SEQ ID NO: 49) |
| Cd20 R | CCCAGGGTAATATGGAAGAGGC (SEQ ID NO: 50) |
| Ihh intron 1F | CAATCATTGACAGCGAGGGC (SEQ ID NO: 51) |
| Ihh intron 1F | GGTGTAGCTCGGTTCTGGTAG (SEQ ID NO: 52) |
| Ihh non-specific F | GGTGTAGCTCGGTTCTGGTAG (SEQ ID NO: 53) |
| Ihh non-specific R | TCACCTGGGACTCCATTTGC (SEQ ID NO: 54) |
| hTAZ F | TCCCAGCCAAATCTCGTGATG (SEQ ID NO: 72) |
| hTAZ R | AGCGCATTGGGCATACTCAT (SEQ ID NO: 81) |

Abbreviations:
Hprt, hypoxanthine guanine phosphoribosyl transferase;
Taz(Wwtr1), WW domain containing transcription regulator 1;
Tgfb1, transforming growth factor, beta 1;
Acta2, α-smooth muscle actin;
Vim, vimentin;
Des, desmin;
Col1a1, collagen type I alpha 1;
Col1a2, collagen type I alpha 2;
Col3a1, collagen, type III alpha 1;
F4/80 (Adgre1), adhesion G protein-coupled receptor E1;
Tnfa, tumor necrosis factor-α;
Mcp1, monocyte chemoattractant protein-1;
Ihh, Indian hedgehog;
Gli2, GLI family zinc finger 2;
Gli3, GLI family zinc finger 3;
Opn, osteopontin;
Timp1, tissue inhibitor of metalloproteinase 1;
Cpt1b, carnitine palmitoyltransferase 1B;
Pparg, peroxisome proliferator-activated receptor-γ;
Scd1, stearoyl-CoA desaturase;
Fasn, fatty acid synthase;
Acaca, acetyl-CoA carboxylase-α;
Cd3, CD3 antigen;
Cd20, B-lymphocyte antigen;
Ihh intron: specific TAZ/TEAD binding area in 1$^{st}$ intron of Ihh gene;
Ihh non-specific: non-specific TAZ/TEAD binding site in mouse Ihh gene distal promoter;
hTAZ: human WW domain containing transcription regulator 1.

Measurement of Hydroxyproline Content of Liver Tissue

Hydroxyproline liver content was measured as previously described (Bataller et al., 2003; Seki et al., 2009). Briefly, liver tissue was homogenized, and proteins were precipitated using trichloroacetic acid. Samples were hydrolyzed by incubation with 6N hydrochloric acid at 110° C. for 16 h followed by neutralization with sodium hydroxide. Liver hydrolysates were oxidized using chloramine-T, followed by incubation with Ehrlich's perchloric acid reagent for color development. Absorbance was measured at 560 nm, and hydroxyproline quantities were calculated by reference to standards processed in parallel. Results are expressed as ng per mg liver weight.

Statistical Analysis

All results are presented as mean±SEM. P values were calculated using the Student's t-test for normally distributed data and the Mann-Whitney rank sum test for non-normally distributed data, One-way ANOVA with post-hoc Tukey test was used to evaluate differences among groups when 3 or more groups were analyzed.

Redox-Responsive Liver-Targeting Nanoparticle Platform for siRNA Delivery

Synthesis of the L-Cystine-Based Poly(Disulfide) (PDSA) Polymers

PDSA polymers were prepared by one-step polycondensation of L-cystine dimethyl ester dihydrochloride ((H-Cys-OMe)2.2HCl) and dichlorides or Bis-nitrophenol esters of different fatty diacids. A standard synthesis procedure was carried out as follows: (H-Cys-OMe)2.2HCl (10 mmol) and triethylamine (15 mmol) were dissolved in 20.0 mL DMSO, then the dichloride of fatty acid (10 mmol) DMSO solution (10 mL) was added into the cystine mixture solution dropwise. The solution was stirred for 15 min to obtain a uniform mixture, precipitated twice in 250 mL of cold ethyl ether, and dried under reduced atmosphere. The final product was a yellow or brown yellow powder.

The synthesis scheme is shown below.

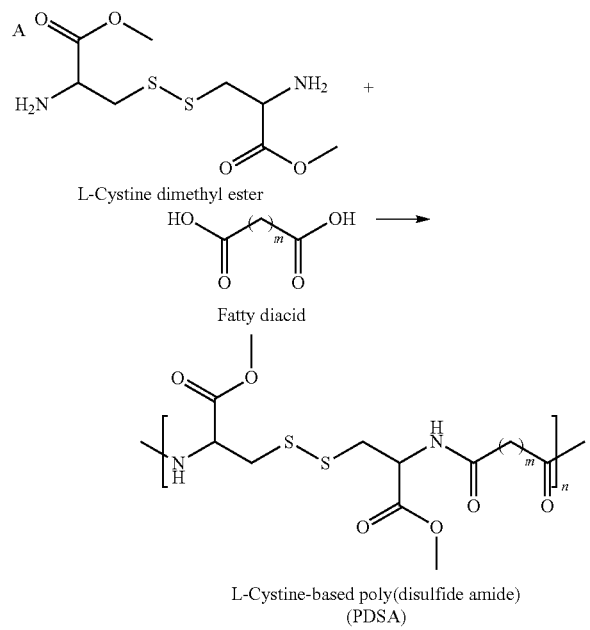

L-Cystine dimethyl ester

Fatty diacid

L-Cystine-based poly(disulfide amide) (PDSA)

Redox-Responsive Behavior of the PDSA Polymers

GPC analysis was used to study the redox-responsive behavior of the PDSA polymers. The polymer (1 mg) was dissolved in 2 mL of DMF/H$_2$O (9:1, V/V) and then GSH (6.2 mg, 0.02 mmol) was added to obtain a solution with GSH concentration of 10 mM. At predetermined intervals, 100 µL of the solution was taken for GPC analysis.

Preparation and Characterization of Nanoparticles (NPs)

The PDSA polymers were dissolved in DMF or DMSO to form a homogenous solution with a concentration of 20 mg/mL. Subsequently, 200 µL of this solution was taken and mixed with 140 µL of DSPE-PEG3000 (20 mg/mL in DMF), 50 µL of G0-C14 (5 mg/mL in DMF) and 1 nmol siRNA (0.1 nmol/µL aqueous solution). Under vigorously stirring (1000 rpm), the mixture was added dropwise to 5 mL of deionized water. The NP dispersion formed was transferred to an ultrafiltration device (EMD Millipore, MWCO 100 K) and centrifuged to remove the organic solvent and free compounds. After washing with deionized water (3×5 mL), the siRNA loaded NPs were dispersed in 1 mL of phosphate buffered saline (PBS, pH 7.4) solution. Size and zeta potential were determined by DLS. The morphology of NPs was visualized on TEM. To determine the siRNA encapsulation efficiency, DY547-labelled GL3 siRNA (DY547-siRNA) loaded NPs were prepared according to the method described above. A small volume (50 µL) of the NP solution was withdrawn and mixed with 20-fold DMSO. The fluorescence intensity of DY547-siRNA was measured using a Synergy HT multi-mode microplate reader (BioTek Instruments) and compared to the free DY-547 labelled GL3 siRNA solution (1 nmol/mL PBS solution).

Redox-Responsive Behavior of the NPs

The siRNA loaded NPs were prepared as described above and dispersed in PBS containing 10 mM GSH. At predetermined time point, the particle size was examined by DLS and the particle morphology was observed on TEM. To evaluate the intracellular redox-responsive behavior, the NPs with Nile red and coumarin 6 encapsulated in their hydrophobic cores were prepared and then incubated with HeLa cells for different time. The fluorescence of Nile red and coumarin 6 was observed a FV1000 confocal laser scanning microscope (CLSM, Olympus). If the NPs respond to redox stimulus, the Nile red and coumarin 6 will release and only green fluorescence of coumarin 6 can be observed under CLSM. If the NPs are intact, the fluorescence of coumarin 6 will be quenched by Nile red and only red fluorescence can be observed under CLSM.

Evaluation of Endosomal Escape

Luc-HeLa cells (20,000 cells) were seeded in discs and incubated in 1 mL of RPMI 1640 medium containing 10% FBS for 24 h. Subsequently, the DY547-siRNA-loaded NPs were added, and the cells were allowed to incubate for 1 or 2 h. After removing the medium and subsequently washing with PBS (pH 7.4) solution thrice, the endosomes and nuclei were stained with lysotracker green and Hoechst 33342, respectively. The cells were then viewed under CLSM.

In Vitro siRNA Release

DY547-labelled siRNA (DY547-siRNA) was loaded into the NPs according to the method described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 µL of the NP solution was withdrawn and mixed with 20-fold DMSO. The fluorescence intensity of DY547-siRNA was determined by Synergy HT multi-mode microplate reader.

Luciferase Silencing

Luciferase expressing HeLa (Luc-HeLa) cells were seeded in 96-well plates (5,000 cells per well) and incubated in 0.1 mL of RPMI 1640 medium with 10% FBS for 24 h. Thereafter, the Luc siRNA-loaded NPs were added. After incubating for 24 h, the cells were washed with fresh medium and allowed to incubate for another 48 h. The expression of firefly luciferase in HeLa cells was determined using Steady-Glo luciferase assay kits. Cytotoxicity was measured using the Alamar Blue assay according to the manufacturer's protocol. The luminescence or fluorescence intensity was measured using a microplate reader, and the average value of five independent experiments was collected. As a control, the silencing effect of Lipo2K/Luc siRNA complexes was also evaluated according to the procedure described above and compared to that of Luc siRNA loaded NPs.

Preparation of Wwtr1 (TAZ) siRNA Loaded NPs

The PDSA polymers were dissolved in DMF to form a homogenous solution with a concentration of 20 mg/mL. Subsequently, 200 µL of this solution was taken and mixed with 140 µL of DSPE-PEG3000 (20 mg/mL in DMF), 50 µL of G0-C14 (5 mg/mL in DMF) and 1 nmol TAZ siRNA (0.1 nmol/µL aqueous solution). Under vigorously stirring (1000 rpm), the mixture was added dropwise to 5 mL of deionized water. The NP dispersion formed was transferred to an ultrafiltration device (EMD Millipore, MWCO 100 K) and centrifuged to remove the organic solvent and free compounds. After washing with deionized water (3×5 mL), the TAZ siRNA loaded NPs were dispersed in 1 mL of phosphate buffered saline (PBS, pH 7.4) solution.

In Vitro TAZ Silencing

Hepatocytes (AML12 cells) were seeded in 6-well plates (50,000 cells per well) and incubated in 1 mL of DMEM/F12 (1:1, v:v) medium containing 10% FBS for 24 h. Subsequently, the cells were incubated with the TAZ siRNA loaded NPs for 24 h. After washing the cells with PBS thrice, the cells were further incubated in fresh medium for another 48 h. Thereafter, the cells were digested by trypsin and the proteins were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM Na3VO4, 1 mM EDTA), supplemented with protease inhibitor cocktail and 1 mM phenylmethanesulfonyl fluoride (PMSF). The expression of TAZ was examined using the western blot analysis.

Western Blot

Equal amounts of proteins were added to SDS-PAGE gels and separated by gel electrophoresis. After transferring the proteins from gel to polyvinylidene difluoride (PVDF) membrane, the blots were blocked with 3% BSA in TBST (50 mM Tris-HCl pH 7.4, 150 mM NaCl, and 0.1% Tween 20) and then incubated with a mixture of TAZ rabbit antibody (Cell Signaling, catalog #8418S) and β-actin rabbit antibody (Cell Signaling, catalog #13E5). The expression of TAZ was detected with horseradish peroxidase (HRP)-conjugated secondary antibody (anti-rabbit IgG HRP-linked antibody, Cell Signaling) and an enhanced chemiluminescence (ECL) detection system (Pierce).

Animals

Healthy female C57BL/6 mice (4-5 weeks old) were purchased from Charles River Laboratories. All in vivo studies were performed in accordance with National Institutes of Health animal care guidelines and in strict pathogen-free conditions in the animal facility of Brigham and Women's Hospital. Animal protocol was approved by the Institutional Animal Care and Use Committees on animal care (Harvard Medical School).

Pharmacokinetics Study

Healthy female C57BL/6 mice were randomly divided into two groups (n=3) and given an intravenous injection of either (i) free DY647-labelled Luc siRNA (DY647-siRNA) or (ii) DY647-siRNA loaded NPs at a 1 nmol siRNA dose per mouse. At predetermined time intervals, orbital vein blood (20 µL) was withdrawn using a tube containing heparin, and the wound was pressed for several seconds to stop the bleeding. The fluorescence intensity of DY-647 labelled siRNA in the blood was determined using a microplate reader.

Biodistribution

Healthy female C57BL/6 mice were randomly divided into two groups (n=3) and given an intravenous injection of either (i) free DY677-labelled Luc siRNA (DY677-siRNA) or (ii) DY677-siRNA loaded NPs at a 1 nmol siRNA dose per mouse. Twenty-four hours after the injection, the mice were imaged using the Maestro 2 In-Vivo Imaging System (Cri Inc). Main organs were then harvested and imaged. To quantify the accumulation of NPs in tumors and organs, the fluorescence intensity of each tissue was quantified by Image-J.

Immune Response

Healthy female C57BL/6 mice were randomly divided into three groups (n=3) and given an intravenous injection of either (i) PBS, (ii) naked TAZ siRNA or (iii) TAZ siRNA loaded NPs at a 1 nmol siRNA dose per mouse. Twenty-four hours after injection, blood was collected and serum isolated for measurements of representative cytokines (TNF-α, IL-6, IL-12, and IFN-γ) by enzyme-linked immunosorbent assay or ELISA (PBL Biomedical Laboratories and BD Biosciences) according to the manufacturer's instructions.

Histology

Healthy female C57BL/6 mice were randomly divided into three groups (n=3) and administered daily intravenous injections of either (i) PBS or (ii) TAZ siRNA loaded NPs at a 1 nmol siRNA dose per mouse. After three consecutive injections (once every day), the main organs were collected 24 h post the final injection, fixed with 4% paraformaldehyde, and embedded in paraffin. Tissue sections were stained with hematoxylin-eosin (H&E) and viewed under an optical microscope.

Design and Synthesis of Nanoparticles for siRNA Delivery to Target Liver Genes

Redox-responsive hydrophobic polymer was synthesized which could co-assemble with lipid-PEG to form spherical NPs for siRNA delivery to target liver genes involved in non-alcoholic steatohepatitis (NASH). The intracellular levels of glutathione (GSH) are much higher than that in extracellular fluid. Redox-sensitive approach is particularly promising to enhance the exposure of target cells to therapeutic molecules. In this example, L-cystine dimethyl ester and fatty diacid were used to synthesize a library of L-cystine-based poly(disulfide amide) polymers (PDSA).

Figure 10A:
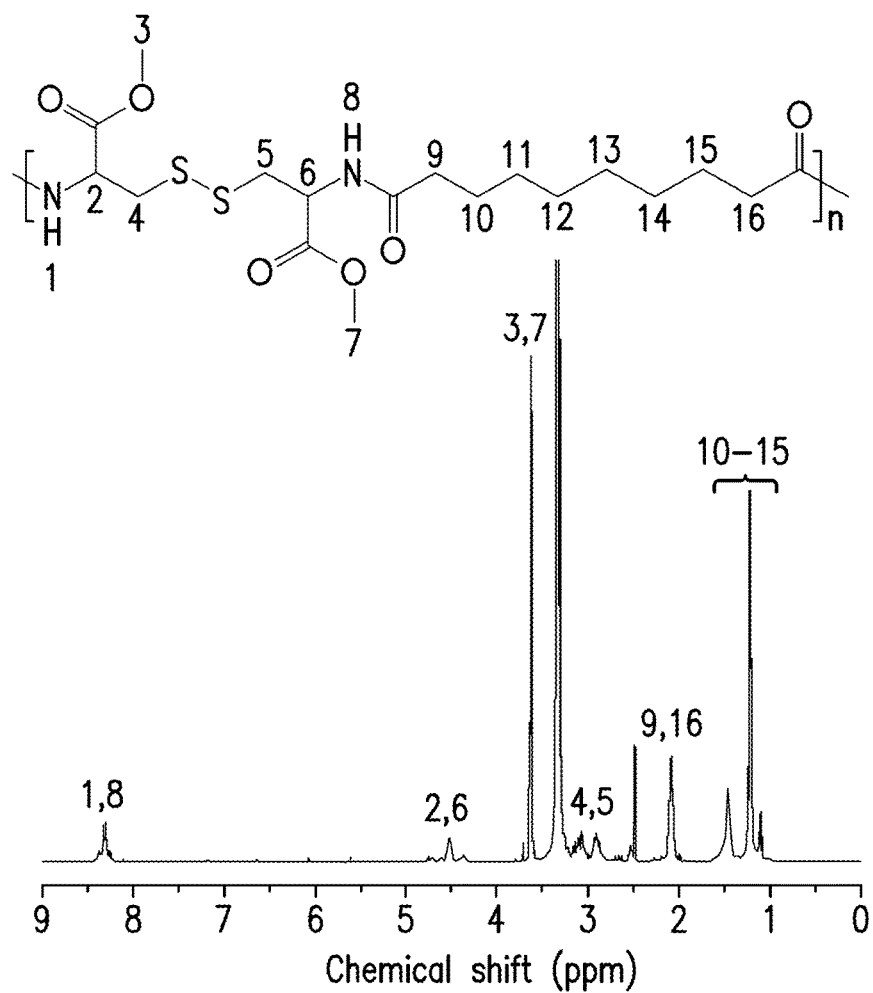
FIGS. 10A-10B are spectra and profiles of PDSA8-polymer.
Figure 10B:
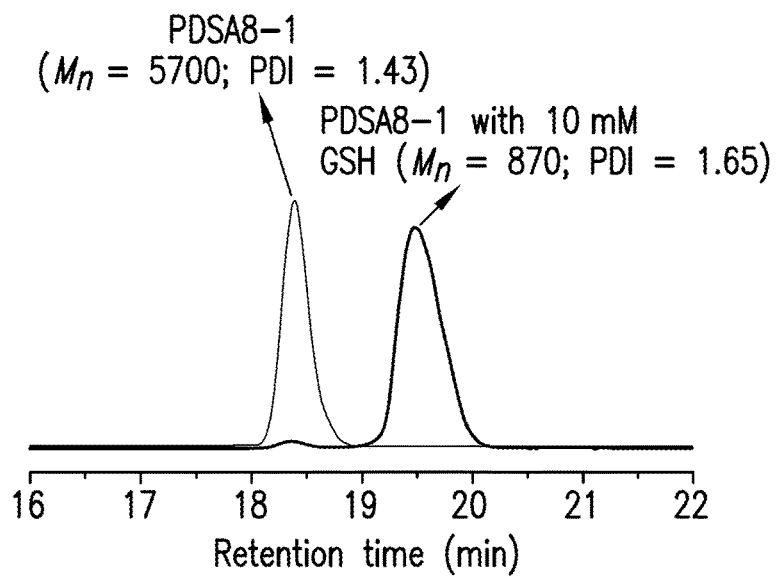
Figure 11A:
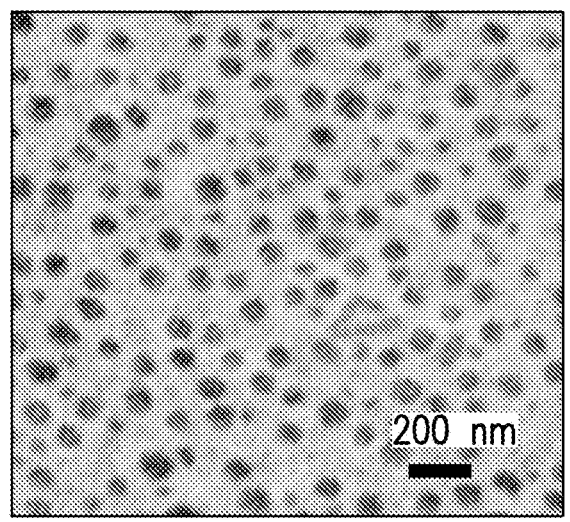
FIGS. 11A-B are a micrograph and a graph respectively, showing morphology and distribution of the Luc siRNA loaded PDSA8-1 NPs in PBS solution.
Figure 11B:
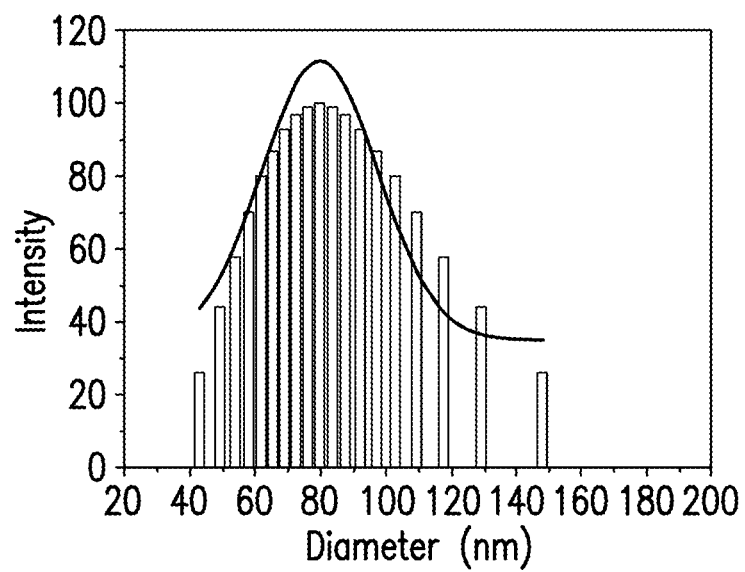
Figure 12A:
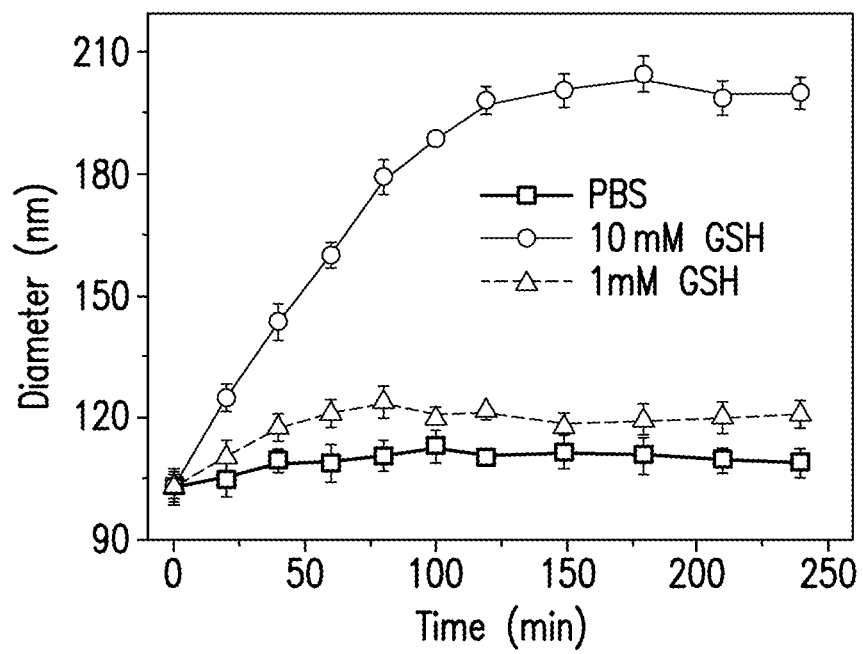
FIGS. 12A-B are a graph and an electron micrograph showing size change and morphology of Luc siRNA loaded PDSA8-1 NPs
Figure 12B:
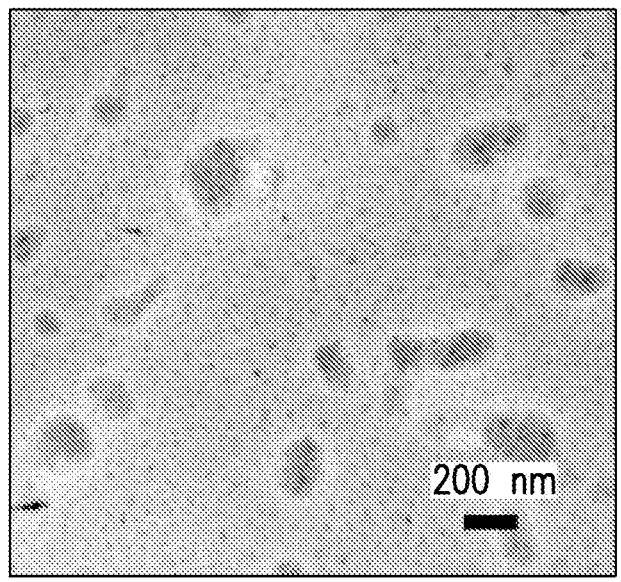
Figure 13:
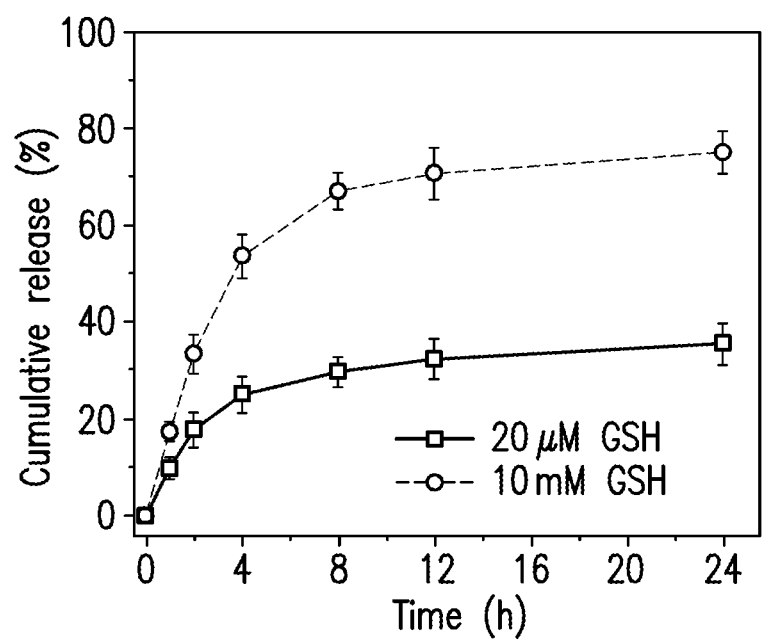
FIG. 13 is a graph showing cumulative siRNA release from the DY-547 siRNA loaded PDSA8-1 NPs incubated in PBS solution containing GSH at different concentrations.
Figure 14A:
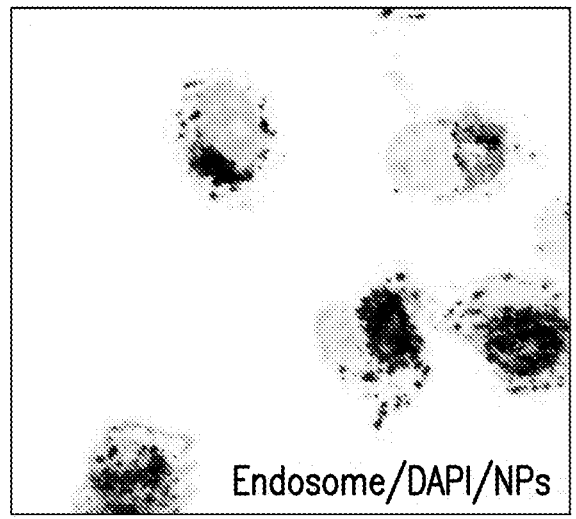
FIGS. 14A-B are fluorescent images of Luc-HeLa cells incubated with the DY-547 siRNA loaded PDSA8-1 NPs for 1 (FIG. 14A) and 4 h (FIG. 14B).
Figure 14B:
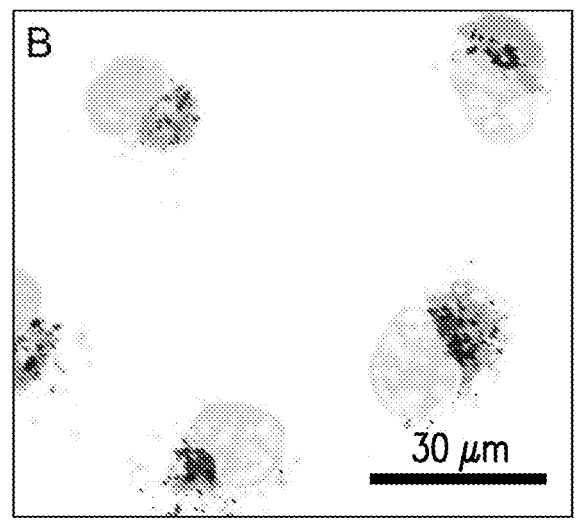
Figure 15:
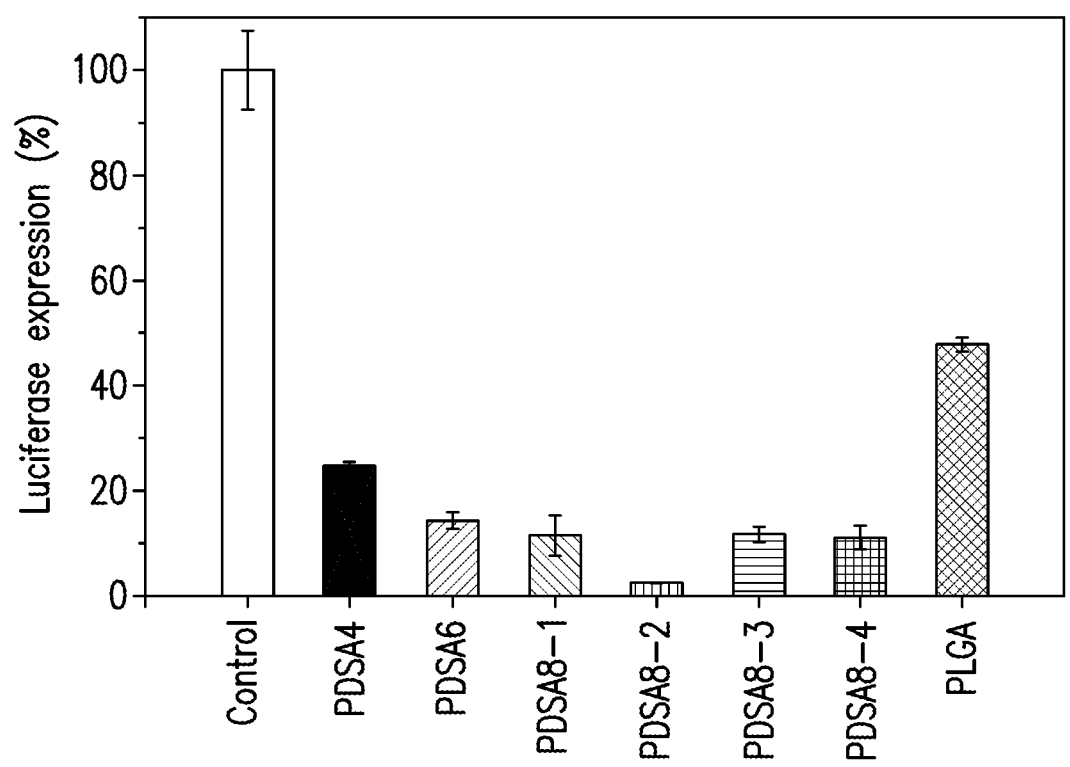
FIG. 15 is a graph showing Luc expression in Luc-HeLa cells treated with the Luc siRNA loaded PDSA or PLGA NPs at 10 nM siRNA dose.

Feed compositions and molecular weight of the PDSA polymers are summarized in Table 6. Taking PDSA8-1, for example, the NMR spectrum in FIG. 10A demonstrates the success in the synthesis of this polymer. With the presence of multiple disulfide bonds, there is a significant decrease in the molecule weight of PDSA8-1 incubated in 10 mM glutathione (GSH) solution (FIG. 10B), demonstrating the redox response of the PDSA8-1 polymer. When mixing this redox-responsive polymer with DSPE-PEG3000, siRNA and cationic lipid (Xiaoyang Xu et al. *Proc Nati Acad Sci USA*, 2013, 110, 18638-18643) in water miscible solvent such as DMF, DMSO, etc., spherical NPs with an average size of ~100 nm (FIG. 11) can be formed via nanoprecipitation method, in which hydrophilic PEG chains are on the outer shell and siRNA is encapsulated in the hydrophobic core. The physiochemical properties of the siRNA loaded NPs made with other PDSA polymers are summarized in Table 7. When incubating these siRNA loaded NPs (e.g., PDSA8-1 NPs, FIG. 12) with 10 mM GSH, the breakage of the disulfide bonds in the polymer backbone induces aggregation and increase in the particle size, which thereby leads to fast siRNA release (FIG. 13). In vitro experimental results show that the PDSA8-1 NPs have efficient endosomal escape ability as seen in fluorescent images of Luc-HeLa cells incubated with the siRNA loaded NPs for 1 and 4 h (FIG. 14). Moreover, with the highly concentrated GSH in cytoplasm to induce the breakage of the NPs, the siRNA loaded PDSA8-1 NPs show high efficacy in silencing Luc expression in HeLa cells (>90% knockdown at 10 nM siRNA dose, FIG. 15), which is much higher than that of cells treated with Luc siRNA loaded PLGA NPs (non-redox-responsive), demonstrating that the redox response predominately contributes to the efficient gene silencing of the PDSA8-1 NPs.

Figure 16:
FIG. 16 is a blot showing TAZ expression in AML12 cells treated with the TAZ siRNA loaded PDSA8-1 NPs at different siRNA doses.
Figure 17:
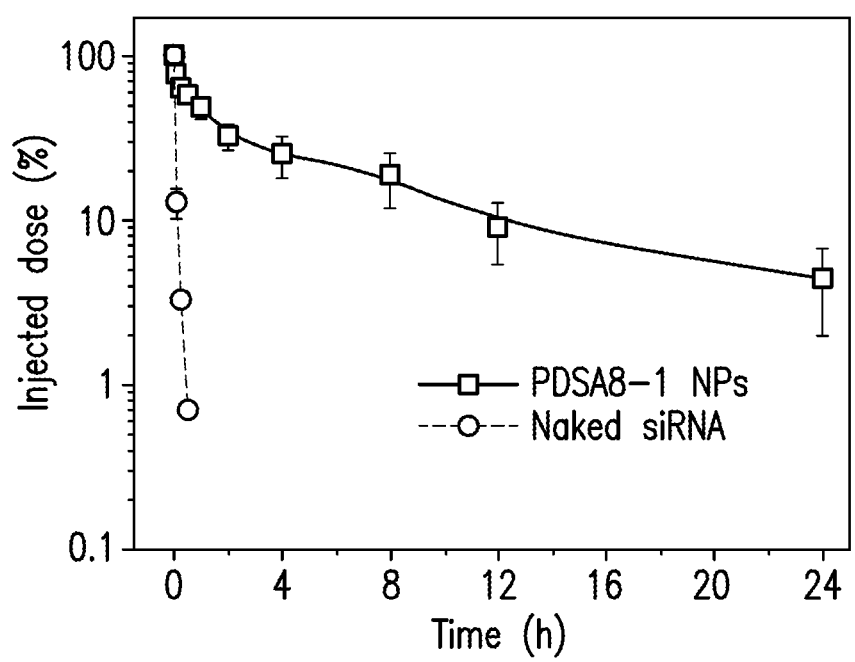
FIG. 17 is a graph showing the pharmacokinetics of naked DY-647 siRNA and DY647-siRNA loaded PDSA8-1 NPs.
Figure 18A:
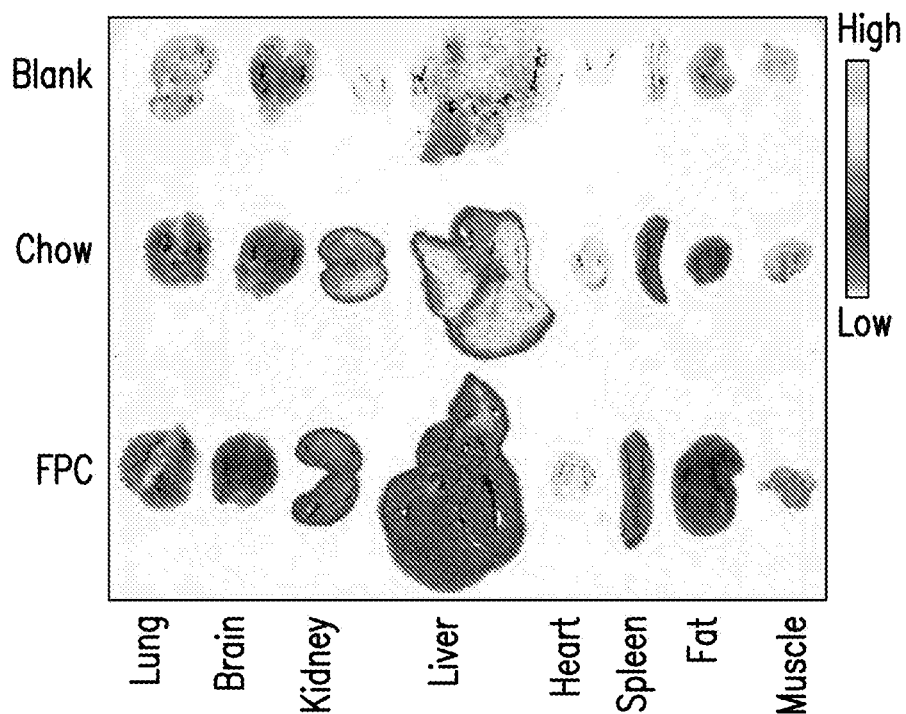
FIGS. 18A-B are a fluorescent image and a graph showing the biodistribution of the DY677-siRNA loaded PDSA8-1 NPs in main organs of the normal (Chow) and NASH model (FPC) mice sacrificed 24 h post injection of the NPs.
Figure 18B:
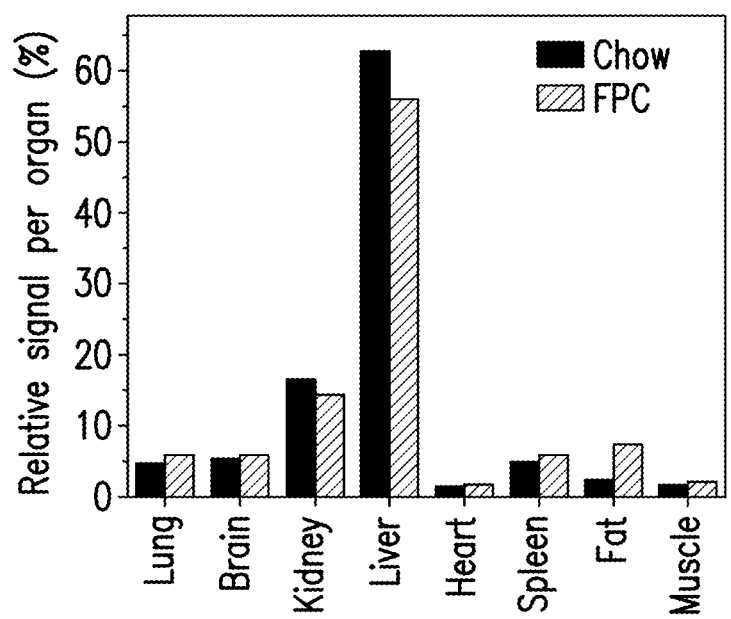
Figure 19:
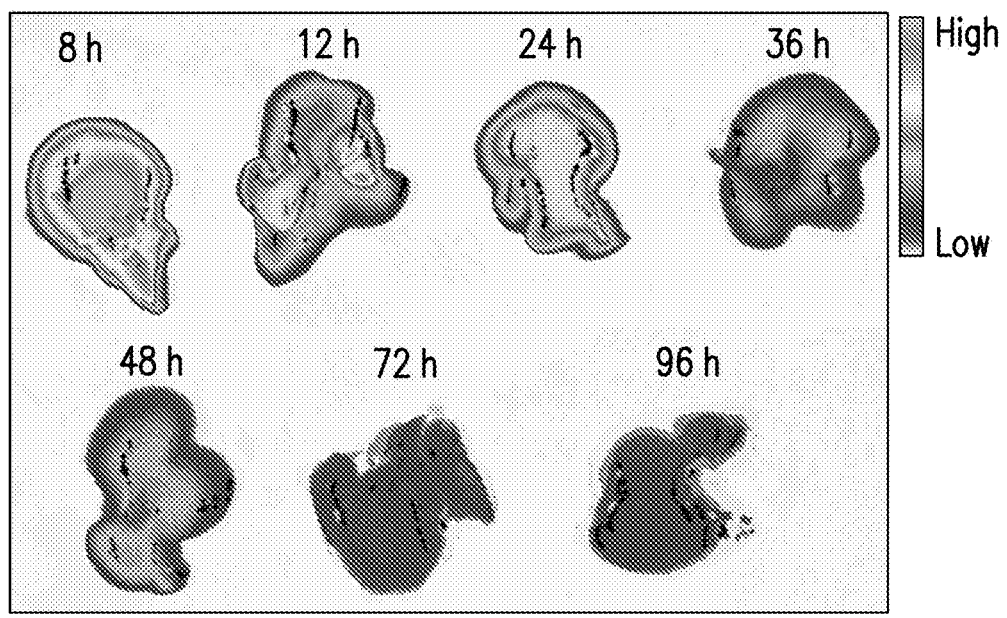
FIG. 19 are images showing the accumulation of the DY677-siRNA loaded PDSA8-1 NPs in liver of the normal mice sacrificed 8, 12, 24, 36, 48, 72 and 96 h post injection of the NPs. The highest amount is shown in the center of the liver tissue section for the 8 hour time period, while the least amount is shown for the tissue section at the 96 hour period.

These redox-responsive NPs can be used as a robust nanoplatform to deliver therapeutic siRNA to target liver genes involved in NASH. After treatment with the NPs loaded TAZ siRNA, there is a significant decrease in the TAZ expression in hepatocytes, as demonstrated by the western blot result shown in FIG. 16. In vivo experimental results demonstrated that these NPs have a long/desirable blood circulation (FIG. 17) and show high targeted accumulation in liver tissue (FIGS. 18 and 19).

TABLE 6

Feed compositions and molecular weight of the PDSA polymers.

|  | Poly(disulfide amide) | $M_n^a$ | $M_w$ | Polydispersity |
|---|---|---|---|---|
| m = 4 | Cys-PDSA4 | 2900 | 4300 | 1.48 |
| m = 6 | Cys-PDSA6 | 3900 | 5700 | 1.46 |
| m = 8 | Cys-PDSA8-1 | 4700 | 7800 | 1.66 |
| m = 8 | Cys-PDSA8-2 | 5700 | 7300 | 1.43 |
| m = 8 | Cys-PDSA8-3 | 9300 | 15200 | 1.63 |
| m = 8 | Cys-PDSA8-4 | 11700 | 16600 | 1.42 |

*Determined by GPC using DMF as the eluent

TABLE 7

Size, siRNA encapsulation efficiency (EE%) and zeta potential of the NPs of PDSA polymers.

|  | Cys-PDSA4 | Cys-PDSA6 | Cys-PDSA8-1 | Cys-PDSA8-2 | Cys-PDSA8-3 | Cys-PDSA8-4 |
|---|---|---|---|---|---|---|
| Size (nm)$^a$ | 155.7 | 134.5 | 118.9 | 102.9 | 99.4 | 93.4 |
| EE%$^b$ | 29.7 | 35.1 | 46.3 | 55.9 | 79.4 | 88.2 |
| ξ (mV) | −6.79 | −8.08 | −9.79 | −11.21 | −12.05 | −20.01 |

$^a$N/P ratio is 20:1.
$^b$siRNA encapsulation efficiency.

Additional methods relating to nanoparticle siRNA formulations can be found in U.S. Patent Publication No. 20160022835. Desirable features of nanoparticle delivery of the TAZ siRNA and related inhibitors described herein include increased stability and the ability to avoid immune degradation. It is noted that the TAZ siRNA NPs have two main components: 1) a hydrophobic inner core that is made with redox-responsive polymers to encapsulate TAZ siRNA, and 2) a hydrophilic outer shell that can allow the TAZ NPs to evade recognition by immune system components and increase blood circulation half-life. The NPs may also include a third component: 3) a targeting ligand that can specifically bind to its receptor on hepatocytes. As demonstrated in the data described herein, the TAZ siRNA NPs exhibited the ability to knock down TAZ expression to a high degree.

A number of additional techniques will be suitable for liver-specific targeting of the present compositions including pharmaceutical compositions described herein. Such methods can be found in U.S. Patent Publication No. 20160017335 and Fitzgerald et al. (N. Engl. J. Med. 2017; 376:41-51; Jan. 5, 2017 DOI: 10.1056/NEJMoa1609243). These methods for producing modified siRNA have been applied to the proprotein convertase subtilisin-kexin type 9 (PCSK9) target and have produced stable siRNA's that have excellent, very low toxicity profiles and are undergoing clinical trials, as described for the product Inclisiran (ALN-PCSsc), a long-acting RNA interference (RNAi) therapeutic agent that inhibits the synthesis of PCSK9, a target for the lowering of low-density lipoprotein (LDL) cholesterol.

Such methods for producing a stable and modified siRNA of the TAZ and related inhibitors described herein would be expected to exhibit similarly desirable profiles.

REFERENCES

Abdelmalek, M. F., Suzuki, A., Guy, C., Unalp-Arida, A., Colvin, R., Johnson, R. J., Diehl, A. M., and Nonalcoholic Steatohepatitis Clinical Research, N. (2010). Increased fructose consumption is associated with fibrosis severity in patients with nonalcoholic fatty liver disease. Hepatology 51, 1961-1971.

Angulo, P., Kleiner, D. E., Dam-Larsen, S., Adams, L. A., Bjornsson, E. S., Charatcharoenwitthaya, P., Mills, P. R., Keach, J. C., Lafferty, H. D., Stahler, A., et al. (2015). Liver Fibrosis, but No Other Histologic Features, Is Associated With Long-term Outcomes of Patients With Nonalcoholic Fatty Liver Disease. Gastroenterology 149, 389-397 e310.

Bataller, R., Schwabe, R. F., Choi, Y. H., Yang, L., Paik, Lindquist, J., Qian, T., Schoonhoven, R., Hagedorn, C. H., Lemasters, J. J., et al. (2003). NADPH oxidase signal transduces angiotensin II in hepatic stellate cells and is critical in hepatic fibrosis. J Clin Invest 112, 1383-1394.

Bertero, T., Cottrill, K. A., Annis, S., Bhat, B., Gochuico, B. R., Osorio, J. C., Rosas, I., Haley, K. J., Corey, K. E., Chung, R. T., et al. (2015). A YAP/TAZ-miR-130/301 molecular circuit exerts systems-level control of fibrosis in a network of human diseases and physiologic conditions. Sci Rep 5, 18277.

Bieghs, V., Hendrikx, T., van Gorp, P. J., Verheyen, F., Guichot, Y. D., Walenbergh, S. M., Jeurissen, M. L., Gijbels, M., Rensen, S. S., Bast, A., et al. (2013). The cholesterol derivative 27-hydroxycholesterol reduces steatohepatitis in mice. Gastroenterology 144, 167-178 e161.

Bohinc, B. N., and Diehl, A. M. (2012). Mechanisms of disease progression in NASH: new paradigms. Clin Liver Dis 16, 549-565.

Chan, F. K., Luz, N. F., and Moriwaki, K. (2015). Programmed necrosis in the cross talk of cell death and inflammation. Annu Rev Immunol 33, 79-106.

Charlton, M., Krishnan, A., Viker, K., Sanderson, S., Cazanave, S., McConico, A., Masuoko, H., and Gores, G. (2011). Fast food diet mouse: novel small animal model of NASH with ballooning, progressive fibrosis, and high physiological fidelity to the human condition. Am J Physiol Gastrointest Liver Physiol 301, G825-834.

Clapper, J. R., Hendricks, M. D., Gu, G., Wittmer, C., Dolman, C. S., Herich, J., Athanacio, J., Villescaz, C., Ghosh, S. S., Heilig, J. S., et al. (2013). Diet-induced mouse model of fatty liver disease and nonalcoholic steatohepatitis reflecting clinical disease progression and methods of assessment. Am J Physiol Gastrointest Liver Physiol 305, G483-495.

Day, C. P., and James, O. F. (1998). Steatohepatitis: a tale of two "hits"? Gastroenterology 114, 842-845.

Dixon, L. J., Berk, M., Thapaliya, S., Papouchado, B. G., and Feldstein, A. E. (2012). Caspase-1-mediated regulation of fibrogenesis in diet-induced steatohepatitis. Lab Invest 92, 713-723.

Dumenco, L., Oguey, D., Wu, J., Messier, N., and Fausto, N. (1995). Introduction of a murine p53 mutation corresponding to human codon 249 into a murine hepatocyte cell line results in growth advantage, but not in transformation. Hepatology 22, 1279-1288.

Ekstedt, M., Franzen, L. E., Mathiesen, U. L., Thorelius, L., Holmqvist, M., Bodemar, G., and Kechagias, S. (2006). Long-term follow-up of patients with NAFLD and elevated liver enzymes. Hepatology 44, 865-873.

Friedman, S. L. (2008). Mechanisms of hepatic fibrogenesis. Gastroenterology 134, 1655-1669.

Ganz, M., Bukong, T. N., Csak, T., Saha, B., Park, J. K., Ambade, A., Kodys, K., and Szabo, G. (2015). Progression of non-alcoholic steatosis to steatohepatitis and fibrosis parallels cumulative accumulation of danger signals that promote inflammation and liver tumors in a high fat-cholesterol-sugar diet model in mice. J Transl Med 13, 193.

Gautheron, J., Vucur, M., Reisinger, F., Cardenas, D. V., Roderburg, C., Koppe, C., Kreggenwinkel, K., Schneider, A. T., Bartneck, M., Neumann, U. P., et al. (2014). A positive feedback loop between RIP3 and JNK controls non-alcoholic steatohepatitis. EMBO Mol Med 6, 1062-1074.

Hebbard, L., and George, J. (2011). Animal models of nonalcoholic fatty liver disease. Nat Rev Gastroenterol Hepatol 8, 35-44.

Hwang, S. M., Jin, M., Shin, Y. H., Ki Choi, S., Namkoong, E, Kim, M., Park, M. Y., and Park, K. (2014). Role of LPA and the Hippo pathway on apoptosis in salivary gland epithelial cells. Exp Mol Med 46, e125.

Ioannou, G. N. (2016). The Role of Cholesterol in the Pathogenesis of NASH. Trends Endocrinol Metab 27, 84-95.

Ishimoto, T., Lanaspa, M. A., Rivard, C. J., Roncal-Jimenez, C. A., Orlicky, D. J., Cicerchi, C., McMahan, R. H., Abdelmalek, M. F., Rosen, H. R., Jackman, M. R., et al. (2013). High-fat and high-sucrose (western) diet induces steatohepatitis that is dependent on fructokinase. Hepatology 58, 1632-1643.

Jolley, C. D., Dietschy, J. M., and Turley, S. D. (1999). Genetic differences in cholesterol absorption in 129/Sv and C57BL/6 mice: effect on cholesterol responsiveness. Am J Physiol 276, G1117-1124.

Joshi-Barve, S., Barve, S. S., Amancherla, K., Gobejishvili, L., Hill, D., Cave, M., Hote, P., and McClain, C. J. (2007). Palmitic acid induces production of proinflammatory cytokine interleukin-8 from hepatocytes. Hepatology 46, 823-830.

Kleiner, D. E., Brunt, E. M., Van Natta, M., Behling, C., Contos, M. J., Cummings, O. W., Ferrell, L. D., Liu, Y. C., Torbenson, M. S., Unalp-Arida, A., et al. (2005). Design and validation of a histological scoring system for nonalcoholic fatty liver disease. Hepatology 41, 1313-1321.

Kohli, R., Kirby, M., Xanthakos, S. A., Softie, S., Feldstein, A. E., Saxena, V., Tang, P. H., Miles, L., Miles, M. V., Balistreri, W. F., et al. (2010). High-fructose, medium chain trans fat diet induces liver fibrosis and elevates plasma coenzyme Q9 in a novel murine model of obesity and nonalcoholic steatohepatitis. Hepatology 52, 934-944.

Liang, W., Menke, A. L., Driessen, A., Koek, G. H., Lindeman, J. H., Stoop, R., Havekes, L. M., Kleemann, R., and van den Hoek, A. M. (2014). Establishment of a General NAFLD Scoring System for Rodent Models and Comparison to Human Liver Pathology. PloS one 9, e115922.

Lisowski, L., Dane, A. P., Chu, K., Zhang, Y., Cunningham, S. C., Wilson, E. M., Nygaard, S., Grompe, M., Alexander, I. E., and Kay, M.A. (2014). Selection and evaluation of clinically relevant AAV variants in a xenograft liver model. Nature 506, 382-386.

Liu, C. Y., Lv, X., Li, T., Xu, Y., Zhou, X., Zhao, S., Xiong, Y., Lei, Q. Y., and Guan, K. L. (2011). PP1 cooperates with ASPP2 to dephosphorylate and activate TAZ. J Biol Chem 286, 5558-5566.

Liu, F., Lagares, D., Choi, K. M., Stopfer, L., Marinkovic, A., Vrbanac, V., Probst, C. K., Hiemer, S. E., Sisson, T. H., Horowitz, J. C., et al. (2015). Mechanosignaling through YAP and TAZ drives fibroblast activation and fibrosis. Am J Physiol Lung Cell Mol Physiol 308, L344-357.

Luedde, T., Kaplowitz, N., and Schwabe, R. F. (2014). Cell death and cell death responses in liver disease: mechanisms and clinical relevance. Gastroenterology 147, 765-783 e764.

Machado, M. V., Michelotti, G. A., Pereira, T. A., Xie, G., Premont, R., Cortez-Pinto, H., and Diehl, A. M. (2015a). Accumulation of duct cells with activated YAP parallels fibrosis progression in non-alcoholic fatty liver disease. J Hepatol.

Machado, M. V., Michelotti, G. A., Xie, G., Almeida Pereira, T., Boursier, J., Bohnic, B., Guy, C. D., and Diehl, A. M. (2015b). Mouse models of diet-induced nonalcoholic steatohepatitis reproduce the heterogeneity of the human disease. PLoS One 10, e0127991.

McCullough, A. J. (2004). The clinical features, diagnosis and natural history of nonalcoholic fatty liver disease. Clin Liver Dis 8, 521-533, viii.

Mederacke, I., Dapito, D. H., Affo, S., Uchinami, H., and Schwabe, R. F. (2015). High-yield and high-purity isolation of hepatic stellate cells from normal and fibrotic mouse livers. Nat Protoc 10, 305-315.

Mederacke, I., Hsu, C. C., Troeger, J. S., Huebener, P., Mu, X., Dapito, D. H., Pradere, J. P., and Schwabe, R. F. (2013). Fate tracing reveals hepatic stellate cells as dominant contributors to liver fibrosis independent of its aetiology. Nat Commun 4, 2823.

Mitani, A., Nagase, T., Fukuchi, K., Aburatani, H., Makita, R., and Kurihara, H. (2009). Transcriptional coactivator with PDZ-binding motif is essential for normal alveolarization in mice. Am J Respir Crit Care Med 180, 326-338.

Miura, K., Yang, L., van Rooijen, N., Brenner, D. A., Ohnishi, H., and Seki, E. (2013). Toll-like receptor 2 and palmitic acid cooperatively contribute to the development of nonalcoholic steatohepatitis through inflammasome activation in mice. Hepatology 57, 577-589.

Nishio, M., Sugimachi, K., Goto, H., Wang, J., Morikawa, T., Miyachi, Y., Takano, Y., Hikasa, H., Itoh, T., Suzuki, S. O., et al. (2016). Dysregulated YAP1/TAZ and TGF-beta signaling mediate hepatocarcinogenesis in Mob1a/1b-deficient mice. Proc Natl Acad Sci USA 113, E71-80.

Piersma, B., Bank, R. A., and Boersema, M. (2015). Signaling in Fibrosis: TGF-beta, WNT, and YAP/TAZ Converge. Front Med (Lausanne) 2, 59.

Rawson, R. B. (2006). An ARC light on lipid metabolism. Cell Metab 4, 181-183.

Razzaque, M. S., Soegiarto, D. W., Chang, D., Long, F., and Lanske, B. (2005). Conditional deletion of Indian hedgehog from collagen type 2alpha1-expressing cells results in abnormal endochondral bone formation. J Pathol 207, 453-461.

Rinella, M. E. (2015). Nonalcoholic fatty liver disease: a systematic review. JAMA 313, 2263-2273.

Saito, A., and Nagase, T. (2015). Hippo and TGF-beta interplay in the lung field. Am J Physiol Lung Cell Mol Physiol 309, L756-767.

Sanyal, A. J., Chalasani, N., Kowdley, K. V., McCullough, A., Diehl, A .M., Bass, N. M., Neuschwander-Tetri, B. A., Lavine, J. E., Tonascia, J., Unalp, A., et al. (2010). Pioglitazone, vitamin E, or placebo for nonalcoholic steatohepatitis. N Engl J Med 362, 1675-1685.

Sato, K., Gosho, M., Yamamoto, T., Kobayashi, Y., Ishii, N., Ohashi, T., Nakade, Y., Ito, K., Fukuzawa, Y., and Yoneda, M. (2015). Vitamin E has a beneficial effect on nonalcoholic fatty liver disease: a meta-analysis of randomized controlled trials. Nutrition 31, 923-930.

Schierwagen, R., Maybuchen, L., Zimmer, S., Hittatiya, K., Back, C., Klein, S., Uschner, F. E., Reul, W., Boor, P., Nickenig, G., et al. (2015). Seven weeks of Western diet in apolipoprotein-E-deficient mice induce metabolic syndrome and non-alcoholic steatohepatitis with liver fibrosis. Sci Rep 5, 12931.

Seki, E., De Minicis, S., Gwak, G. Y., Kluwe, J., Inokuchi, S., Bursill, C. A., Llovet, J. M., Brenner, D. A., and Schwabe, R. F. (2009). CCR1 and CCR5 promote hepatic fibrosis in mice. J Clin Invest 119, 1858-1870.

Shimamura, T., Fujisawa, T., Husain, S. R., Kioi, M., Nakajima, A., and Puri, R. K. (2008). Novel role of IL-13 in fibrosis induced by nonalcoholic steatohepatitis and its amelioration by IL-13R-directed cytotoxin in a rat model. J Immunol 181, 4656-4665.

Singh, S., Allen, A. M., Wang, Z., Prokop, L. J., Murad, M. H., and. Loomba, R. (2015). Fibrosis progression in nonalcoholic fatty liver vs nonalcoholic steatohepatitis: a systematic review and meta-analysis of paired-biopsy studies. Clin Gastroenterol Hepatol 13, 643-654 e641-649; quiz e639-640.

Subramanian, S., Goodspeed, L., Wang, S., Kim, J., Zeng, L., Ioannou, G. N., Haigh, W. G., Yeh, M. M., Kowdley, K. V., O'Brien, K. D., et al. (2011). Dietary cholesterol exacerbates hepatic steatosis and inflammation in obese LDL receptor-deficient mice. J Lipid Res 52, 1626-1635.

Syn, W. K., Choi, S. S., Liaskou, E., Karaca, G. F., Agboola, K. M., Oo, Y. H., Mi, Z., Pereira, T. A., Zdanowicz, M., Malladi, P., et al. (2011). Osteopontin is induced by hedgehog pathway activation and promotes fibrosis progression in nonalcoholic steatohepatitis. Hepatology 53, 106-115.

Syn, W. K., Oo, Y. H., Pereira, T. A., Karaca, G. F., Jung, Y., Omenetti, A., Witek, R. P., Choi, S. S., Guy, C. D., Fearing, C. M., et al. (2010). Accumulation of natural killer T cells in progressive nonalcoholic fatty liver disease. Hepatology 51, 1998-2007.

Teratani, T., Tomita, K., Suzuki, T., Oshikawa, T., Yokoyama, H., Shimamura, K., Tominaga, S., Hiroi, S., Irie, R., Okada, Y., et al. (2012). A high-cholesterol diet exacerbates liver fibrosis in mice via accumulation of free cholesterol in hepatic stellate cells. Gastroenterology 142, 152-164 e110.

Van Rooyen, D. M., Latter, C. Z., Haigh, W. G., Yeh, M. M., Ioannou, G., Kuver, R., Lee, S. P., Teoh, N. C., and Farrell, G. C. (2011). Hepatic free cholesterol accumulates in obese, diabetic mice and causes nonalcoholic steatohepatitis. Gastroenterology 141, 1393-1403, 1403 e1391-1395.

White, D. L., Kanwal, F., and El-Serag, H. B. (2012). Association between nonalcoholic fatty liver disease and risk for hepatocellular cancer, based on systematic review. Clin Gastroenterol Hepatol 10, 1342-1359 e1342.

Wouters, K., van Gorp, P. J., Bieghs, V., Gijbels, M. J., Duimel, H., Lutjohann, D., Kerksiek, A., van Kruchten, R., Maeda, N., Staels, B., et al. (2008). Dietary cholesterol, rather than liver steatosis, leads to hepatic inflammation in hyperlipidemic mouse models of non-alcoholic steatohepatitis. Hepatology 48, 474-486.

Yamada, K., Mizukoshi, E., Sunagozaka, H., Arai, K., Yamashita, T., Takeshita, Y., Misu, H., Takamura, T., Kitamura, S., Zen, Y., et al. (2015). Characteristics of hepatic fatty acid compositions in patients with nonalcoholic steatohepatitis. Liver Int 35, 582-590.

Younossi, Z. M., Page, S., Rafiq, N., Birerdinc, A., Stepanova, M., Hossain, N., Afendy, A., Younoszai, Z., Goodman, Z., and Baranova, A. (2011). A biomarker panel for non-alcoholic steatohepatitis (NASH) and NASH-related fibrosis. Obes Surg 21, 431-439.

Yu, F. X., Zhao, B., and Guan, K. L. (2015). Hippo Pathway in Organ Size Control, Tissue Homeostasis, and Cancer. Cell 163, 811-828.

Zanconato, F., Forcato, M., Battilana, G., Azzolin, L., Quaranta, E., Bodega, B., Rosato, A., Bicciato, S., Cordenonsi, M., and Piccolo, S. (2015). Genome-wide association between YAP/TAZ/TEAD and AP-1 at enhancers drives oncogenic growth. Nat Cell Biol 17, 1218-1227.

Zhang H, et al., 2009 TEAD transcription factors mediate the function of TAZ in cell growth and epithelial-mesenchymal transition. J Biol Chem. 284(20):13355-62.

Zhao, B., Li, L., Lei, Q., and Guan, K. L. (2010). The Hippo-YAP pathway in organ size control and tumorigenesis: an updated version. Genes Dev 24, 862-874.

Zhao, B., Ye, X., Yu, J., Li, L., Li, W., Li, S., Yu, J., Lin, J. D., Wang, C. Y., Chinnaiyan, A. M., et al. (2008). TEAD mediates YAP-dependent gene induction and growth control. Genes Dev 22, 1962-1971.

Zuckerman, J. E. and Davis, M. E. (2015). Clinical experiences with systemically administered siRNA-based therapeutics in cancer. Nature Reviews Drug Discovery, 14:843-856.

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. A method for treating or preventing progression of steatosis to non-alcoholic steatohepatitis (NASH) in a patient in need thereof, the method comprising administering to the patient in need thereof a therapeutically effective amount of an inhibitor of TAZ, where the inhibitor of TAZ is a nucleic acid comprising a sequence complementary to a sequence encoding human TAZ.

2. The method of claim 1, wherein the inhibitor of TAZ is administered to at least one hepatocyte of said patient.

3. The method of claim 1, further comprising administering a therapeutically effective amount of an inhibitor of Indian hedgehog (Ihh), an inhibitor of YAP, an inhibitor of TEAD1, and inhibitor of TEAD2, an inhibitor of TEAD3, an inhibitor of TEAD4, or any combination thereof.

4. The method of claim 1, wherein the nucleic acid is selected from the group consisting of antisense oligonucleotide, siRNA, shRNA, and combinations thereof.

5. The method of claim 1, wherein the sequence complementary to the sequence encoding human TAZ is set forth by SEQ ID NO: 1, SEQ ID NO: 2, SEQ ID NOs: 55-72, or SEQ ID NO: 81.

6. The method of claim 4, wherein the nucleic acid is formulated in a nanoparticle.

7. The method of claim 6, wherein the nanoparticle comprises: 1) a hydrophobic inner core, 2) a hydrophilic outer shell and 3) a hepatocyte targeting ligand.

* * * * *